(12) United States Patent
Drummond et al.

(10) Patent No.: US 11,053,504 B2
(45) Date of Patent: Jul. 6, 2021

(54) HEAT-INDUCIBLE SELF-ASSEMBLING PROTEIN DOMAINS

(71) Applicant: The University of Chicago, Chicago, IL (US)

(72) Inventors: D. Allan Drummond, Chicago, IL (US); Joshua Riback, Chicago, IL (US); Jamie Scott, Chicago, IL (US); Alexandra Rojek, Chicago, IL (US); Pawel Laskowski, Chicago, IL (US); Ronald Rock, Chicago, IL (US); Jagoda Rokicka, Chicago, IL (US); Jakub Kucharczyk, Chicago, IL (US)

(73) Assignee: The University of Chicago, Chicago, IL (US)

( * ) Notice: Subject to any disclaimer, the term of this patent is extended or adjusted under 35 U.S.C. 154(b) by 259 days.

(21) Appl. No.: 15/521,330

(22) PCT Filed: Oct. 23, 2015

(86) PCT No.: PCT/US2015/057139
§ 371 (c)(1),
(2) Date: Apr. 24, 2017

(87) PCT Pub. No.: WO2016/065273
PCT Pub. Date: Apr. 28, 2016

(65) Prior Publication Data
US 2018/0305699 A1    Oct. 25, 2018

Related U.S. Application Data

(60) Provisional application No. 62/068,390, filed on Oct. 24, 2014.

(51) Int. Cl.
*C12N 15/62* (2006.01)
*C07K 14/395* (2006.01)
*C07K 19/00* (2006.01)

(52) U.S. Cl.
CPC ............ *C12N 15/62* (2013.01); *C07K 14/395* (2013.01); *C07K 19/00* (2013.01); *C07K 2319/23* (2013.01); *C07K 2319/43* (2013.01); *C07K 2319/735* (2013.01)

(58) Field of Classification Search
CPC ...... C12N 15/62; C07K 19/00; C07K 14/395; C07K 2319/735
See application file for complete search history.

(56) References Cited

U.S. PATENT DOCUMENTS 9,556,258 B2 * 1/2017 Nti-Gyabaah ... C07K 14/70578
2014/0106399 A1 * 4/2014 Lin ........................ C07K 14/00
435/68.1

FOREIGN PATENT DOCUMENTS

EP          1258494 A1 * 11/2002 ............. C12N 15/62
WO    WO 2000/023600       4/2000

OTHER PUBLICATIONS

Ngo et al. in The Protein Folding Problem and Tertiary Structure Prediction, 1994, Merzetal. (ed.), Birkhauser, Boston, MA, pp. 433 and 492-495.*
Vandenbol et al. (Uniprot Accession No. S53934, glutamate-tRNA ligase, Jul. 2004).*
Rigaut et al., (Nature Biotechnology, vol. 17 (10), pp. 1030-1032, 1999).*
Grousl et al., "Heat shock-induced accumulation of translation elongation and termination factors precedes assembly of stress in S. cerevisiae," *PLOS One* 2013; 8(2): 1-17.
Grousl et al., "Robust heat chock induces eIF2alpha-phosphorylation independent assembly of stress granules containing alF3 and 40S ribosomal subunits in budding yeast, Saccharomyces cerevisiae," *Journal of Cell Science*, 2009; 122: 2078-2088.
Huang et al., Structural Basis for Exquisite Specificity of Affinity Clamps, Synthetic Binding Proteins Generated through Directed Domain-interface Evolution, *J. Mol. Boil*. 2009; 392: 1221-21.
International Search Report and Written Opinion issued in PCT Application No. PCT/US15/57139, dated Jan. 22, 2016.
Marchler-Bauer et al., "CDD: conserved domains and protein three-dimensional structure," *Nucleic Acids Res*. 2013; 41(D1): D348-52.
Simander et al., "Structural basis of yeast aminoacyl-tRNA synthetase complex formation revealed by crystal structures of two binary sub-complexes," *Nucleic Acid Res*. 2006; 34(14): 3968-79.
Wallace et al., "Reversible, specific, active aggregates of endogenous proteins assemble upon heat stress," *Cell*, 2015; 162(6): 1286-1298.
Yao et al., "PAB1 self-association precludes its binding to poly(A), thereby accelerating CCR4 deadenylation in vivo," *Molecular and Cellular Biology*, 2007; 27(17): 6243-6253.

* cited by examiner

*Primary Examiner* — Richard G Hutson
(74) *Attorney, Agent, or Firm* — Norton Rose Fulbright US LLP

(57) ABSTRACT

A heat-inducible self-assembling fusion protein that includes a self-assembly domain and a target protein, wherein the self-assembly domain remains folded during assembly. The aggregate forming fusion protein can be induced to form protein aggregates conjugated to a target protein. The aggregates can be used similarly to beads in many laboratory protocols and other applications. Also disclosed are methods of making and using the protein aggregates.

9 Claims, 21 Drawing Sheets
Specification includes a Sequence Listing.

SEQUENCE LISTING

```
<160> NUMBER OF SEQ ID NOS: 19

<210> SEQ ID NO 1
<211> LENGTH: 376
<212> TYPE: PRT
<213> ORGANISM: Saccharomyces cerevisiae

<400> SEQUENCE: 1

Met Ser Asp Leu Val Thr Lys Phe Glu Ser Leu Ile Ile Ser Lys Tyr
1               5                   10                  15

Pro Val Ser Phe Thr Lys Glu Gln Ser Ala Gln Ala Gln Trp Glu
            20                  25                  30

Ser Val Leu Lys Ser Gly Gln Ile Gln Pro His Leu Asp Gln Leu Asn
        35                  40                  45

Leu Val Leu Arg Asp Asn Thr Phe Ile Val Ser Thr Leu Tyr Pro Thr
    50                  55                  60

Ser Thr Asp Val His Val Phe Glu Val Ala Leu Pro Leu Ile Lys Asp
65                  70                  75                  80
```

Leu Val Ala Ser Ser Lys Asp Val Lys Ser Thr Tyr Thr Tyr Arg
                85                  90                  95

His Ile Leu Arg Trp Ile Asp Tyr Met Gln Asn Leu Leu Glu Val Ser
                100                 105                 110

Ser Thr Asp Lys Leu Glu Ile Asn His Asp Leu Asp Leu Pro His Glu
                115                 120                 125

Val Ile Glu Lys Lys Lys Ala Pro Ala Gly Gly Ala Ala Asp Ala
130                 135                 140

Ala Ala Lys Ala Asp Glu Asp Val Ser Lys Lys Ala Lys Lys Gln Asp
145                 150                 155                 160

His Pro Arg Gly Lys Pro Asp Glu Glu Thr Leu Lys Lys Leu Arg Glu
                165                 170                 175

Glu Ala Lys Ala Lys Lys Ala Ala Lys Lys Ala Ala Asn Ala Lys Gln
                180                 185                 190

Gln Gln Glu Gln Gln Asn Lys Ala Pro Glu Lys Pro Lys Pro Ser Ala
                195                 200                 205

Ile Asp Phe Arg Val Gly Phe Ile Gln Lys Ala Ile Lys His Pro Asp
210                 215                 220

Ala Asp Ser Leu Tyr Val Ser Thr Ile Asp Val Gly Asp Glu Glu Gly
225                 230                 235                 240

Pro Arg Thr Val Cys Ser Gly Leu Val Lys His Phe Pro Leu Asp Ala
                245                 250                 255

Met Gln Glu Arg Tyr Val Val Val Cys Asn Leu Lys Pro Val Asn
                260                 265                 270

Met Arg Gly Ile Lys Ser Thr Ala Met Val Leu Cys Gly Ser Asn Asp
                275                 280                 285

Asp Lys Val Glu Phe Val Glu Pro Pro Lys Asp Ser Lys Ala Gly Asp
290                 295                 300

Lys Val Phe Phe Glu Gly Phe Gly Asp Glu Ala Pro Met Lys Gln Leu
305                 310                 315                 320

Asn Pro Lys Lys Lys Ile Trp Glu His Leu Gln Pro His Phe Thr Thr
                325                 330                 335

Asn Asp Gly Leu Glu Val Ile Phe Lys Asp Glu Glu Lys Asp His
                340                 345                 350

Pro Val Arg Lys Leu Thr Asn Ala Lys Gly Glu Ser Phe Lys Val Ala
                355                 360                 365

Ser Ile Ala Asn Ala Gln Val Arg
                370                 375

<210> SEQ ID NO 2
<211> LENGTH: 751
<212> TYPE: PRT
<213> ORGANISM: Saccharomyces cerevisiae

<400> SEQUENCE: 2

Met Ser Phe Leu Ile Ser Phe Asp Lys Ser Lys His Pro Ala His
1               5                   10                  15

Leu Gln Leu Ala Asn Asn Leu Lys Ile Ala Leu Ala Leu Glu Tyr Ala
                20                  25                  30

Ser Lys Asn Leu Lys Pro Glu Val Asp Asn Asp Asn Ala Ala Met Glu
                35                  40                  45

Leu Arg Asn Thr Lys Glu Pro Phe Leu Leu Phe Asp Ala Asn Ala Ile
                50                  55                  60

Leu Arg Tyr Val Met Asp Asp Phe Glu Gly Gln Thr Ser Asp Lys Tyr

```
             65                  70                  75                  80
        Gln Phe Ala Leu Ala Ser Leu Gln Asn Leu Tyr His Lys Glu Leu
                         85                  90                  95

Pro Gln Gln His Val Glu Val Leu Thr Asn Lys Ala Ile Glu Asn Tyr
                    100                 105                 110

Leu Val Glu Leu Lys Glu Pro Leu Thr Thr Thr Asp Leu Ile Leu Phe
                    115                 120                 125

Ala Asn Val Tyr Ala Leu Asn Ser Ser Leu Val His Ser Lys Phe Pro
                    130                 135                 140

Glu Leu Pro Ser Lys Val His Asn Ala Val Ala Leu Ala Lys Lys His
        145                 150                 155                 160

Val Pro Arg Asp Ser Ser Phe Lys Asn Ile Gly Ala Val Lys Ile
                         165                 170                 175

Gln Ala Asp Leu Thr Val Lys Pro Lys Asp Ser Glu Ile Leu Pro Lys
                    180                 185                 190

Pro Asn Glu Arg Asn Ile Leu Ile Thr Ser Ala Leu Pro Tyr Val Asn
                    195                 200                 205

Asn Val Pro His Leu Gly Asn Ile Ile Gly Ser Val Leu Ser Ala Asp
                    210                 215                 220

Ile Phe Ala Arg Tyr Cys Lys Gly Arg Asn Tyr Asn Ala Leu Phe Ile
        225                 230                 235                 240

Cys Gly Thr Asp Glu Tyr Gly Thr Ala Thr Glu Thr Lys Ala Leu Glu
                         245                 250                 255

Glu Gly Val Thr Pro Arg Gln Leu Cys Asp Lys Tyr His Lys Ile His
                    260                 265                 270

Ser Asp Val Tyr Lys Trp Phe Gln Ile Gly Phe Asp Tyr Phe Gly Arg
                    275                 280                 285

Thr Thr Thr Asp Lys Gln Thr Glu Ile Ala Gln His Ile Phe Thr Lys
                    290                 295                 300

Leu Asn Ser Asn Gly Tyr Leu Glu Glu Gln Ser Met Lys Gln Leu Tyr
        305                 310                 315                 320

Cys Pro Val His Asn Ser Tyr Leu Ala Asp Arg Tyr Val Glu Gly Glu
                         325                 330                 335

Cys Pro Lys Cys His Tyr Asp Asp Ala Arg Gly Asp Gln Cys Asp Lys
                    340                 345                 350

Cys Gly Ala Leu Leu Asp Pro Phe Glu Leu Ile Asn Pro Arg Cys Lys
                    355                 360                 365

Leu Asp Asp Ala Ser Pro Glu Pro Lys Tyr Ser Asp His Ile Phe Leu
                    370                 375                 380

Ser Leu Asp Lys Leu Glu Ser Gln Ile Ser Glu Trp Val Glu Lys Ala
        385                 390                 395                 400

Ser Glu Glu Gly Asn Trp Ser Lys Asn Ser Lys Thr Ile Thr Gln Ser
                         405                 410                 415

Trp Leu Lys Asp Gly Leu Lys Pro Arg Cys Ile Thr Arg Asp Leu Val
                    420                 425                 430

Trp Gly Thr Pro Val Pro Leu Glu Lys Tyr Lys Asp Lys Val Leu Tyr
                    435                 440                 445

Val Trp Phe Asp Ala Thr Ile Gly Tyr Val Ser Ile Thr Ser Asn Tyr
                    450                 455                 460

Thr Lys Glu Trp Lys Gln Trp Trp Asn Asn Pro Glu His Val Ser Leu
        465                 470                 475                 480

Tyr Gln Phe Met Gly Lys Asp Asn Val Pro Phe His Thr Val Val Phe
                         485                 490                 495
```

```
Pro Gly Ser Gln Leu Gly Thr Glu Glu Asn Trp Thr Met Leu His His
            500                 505                 510

Leu Asn Thr Thr Glu Tyr Leu Gln Tyr Glu Asn Gly Lys Phe Ser Lys
            515                 520                 525

Ser Arg Gly Val Gly Val Phe Gly Asn Ala Gln Asp Ser Gly Ile
            530                 535                 540

Ser Pro Ser Val Trp Arg Tyr Tyr Leu Ala Ser Val Arg Pro Glu Ser
545                 550                 555                 560

Ser Asp Ser His Phe Ser Trp Asp Asp Phe Val Ala Arg Asn Asn Ser
                565                 570                 575

Glu Leu Leu Ala Asn Leu Gly Asn Phe Val Asn Arg Leu Ile Lys Phe
            580                 585                 590

Val Asn Ala Lys Tyr Asn Gly Val Val Pro Lys Phe Asp Pro Lys Lys
            595                 600                 605

Val Ser Asn Tyr Asp Gly Leu Val Lys Asp Ile Asn Glu Ile Leu Ser
            610                 615                 620

Asn Tyr Val Lys Glu Met Glu Leu Gly His Glu Arg Arg Gly Leu Glu
625                 630                 635                 640

Ile Ala Met Ser Leu Ser Ala Arg Gly Asn Gln Phe Leu Gln Glu Asn
                645                 650                 655

Lys Leu Asp Asn Thr Leu Phe Ser Gln Ser Pro Glu Lys Ser Asp Ala
            660                 665                 670

Val Val Ala Val Gly Leu Asn Ile Ile Tyr Ala Val Ser Ser Ile Ile
            675                 680                 685

Thr Pro Tyr Met Pro Glu Ile Gly Glu Lys Ile Asn Lys Met Leu Asn
            690                 695                 700

Ala Pro Ala Leu Lys Ile Asp Asp Arg Phe His Leu Ala Ile Leu Glu
705                 710                 715                 720

Gly His Asn Ile Asn Lys Ala Glu Tyr Leu Phe Gln Arg Ile Asp Glu
                725                 730                 735

Lys Lys Ile Asp Glu Trp Arg Ala Lys Tyr Gly Gly Gln Gln Val
            740                 745                 750
```

<210> SEQ ID NO 3
<211> LENGTH: 708
<212> TYPE: PRT
<213> ORGANISM: Saccharomyces cerevisiae

<400> SEQUENCE: 3

```
Met Pro Ser Thr Leu Thr Ile Asn Gly Lys Ala Pro Ile Val Ala Tyr
1               5                   10                  15

Ala Glu Leu Ile Ala Ala Arg Ile Val Asn Ala Leu Ala Pro Asn Ser
            20                  25                  30

Ile Ala Ile Lys Leu Val Asp Asp Lys Lys Ala Pro Ala Ala Lys Leu
        35                  40                  45

Asp Asp Ala Thr Glu Asp Val Phe Asn Lys Ile Thr Ser Lys Phe Ala
50                  55                  60

Ala Ile Phe Asp Asn Gly Asp Lys Glu Gln Val Ala Lys Trp Val Asn
65                  70                  75                  80

Leu Ala Gln Lys Glu Leu Val Ile Lys Asn Phe Ala Lys Leu Ser Gln
                85                  90                  95

Ser Leu Glu Thr Leu Asp Ser Gln Leu Asn Leu Arg Thr Phe Ile Leu
            100                 105                 110

Gly Gly Leu Lys Tyr Ser Ala Ala Asp Val Ala Cys Trp Gly Ala Leu
```

```
            115                 120                 125
Arg Ser Asn Gly Met Cys Gly Ser Ile Ile Lys Asn Lys Val Asp Val
    130                 135                 140

Asn Val Ser Arg Trp Tyr Thr Leu Leu Glu Met Asp Pro Ile Phe Gly
145                 150                 155                 160

Glu Ala His Asp Phe Leu Ser Lys Ser Leu Glu Leu Lys Lys Ser
                165                 170                 175

Ala Asn Val Gly Lys Lys Glu Thr His Lys Ala Asn Phe Glu Ile
            180                 185                 190

Asp Leu Pro Asp Ala Lys Met Gly Glu Val Val Thr Arg Phe Pro Pro
        195                 200                 205

Glu Pro Ser Gly Tyr Leu His Ile Gly His Ala Lys Ala Ala Leu Leu
    210                 215                 220

Asn Gln Tyr Phe Ala Gln Ala Tyr Lys Gly Lys Leu Ile Ile Arg Phe
225                 230                 235                 240

Asp Asp Thr Asn Pro Ser Lys Glu Lys Glu Phe Gln Asp Ser Ile
                245                 250                 255

Leu Glu Asp Leu Asp Leu Leu Gly Ile Lys Gly Asp Arg Ile Thr Tyr
            260                 265                 270

Ser Ser Asp Tyr Phe Gln Glu Met Tyr Asp Tyr Cys Val Gln Met Ile
        275                 280                 285

Lys Asp Gly Lys Ala Tyr Cys Asp Asp Thr Pro Thr Glu Lys Met Arg
    290                 295                 300

Glu Glu Arg Met Asp Gly Val Ala Ser Ala Arg Arg Asp Arg Ser Val
305                 310                 315                 320

Glu Glu Asn Leu Arg Ile Phe Thr Glu Glu Met Lys Asn Gly Thr Glu
                325                 330                 335

Glu Gly Leu Lys Asn Cys Val Arg Ala Lys Ile Asp Tyr Lys Ala Leu
            340                 345                 350

Asn Lys Thr Leu Arg Asp Pro Val Ile Tyr Arg Cys Asn Leu Thr Pro
        355                 360                 365

His His Arg Thr Gly Ser Thr Trp Lys Ile Tyr Pro Thr Tyr Asp Phe
    370                 375                 380

Cys Val Pro Ile Val Asp Ala Ile Glu Gly Val Thr His Ala Leu Arg
385                 390                 395                 400

Thr Ile Glu Tyr Arg Asp Arg Asn Ala Gln Tyr Asp Trp Met Leu Gln
                405                 410                 415

Ala Leu Arg Leu Arg Lys Val His Ile Trp Asp Phe Ala Arg Ile Asn
            420                 425                 430

Phe Val Arg Thr Leu Leu Ser Lys Arg Lys Leu Gln Trp Met Val Asp
        435                 440                 445

Lys Asp Leu Val Gly Asn Trp Asp Asp Pro Arg Phe Pro Thr Val Arg
    450                 455                 460

Gly Val Arg Arg Arg Gly Met Thr Val Glu Gly Leu Arg Asn Phe Val
465                 470                 475                 480

Leu Ser Gln Gly Pro Ser Arg Asn Val Ile Asn Leu Glu Trp Asn Leu
                485                 490                 495

Ile Trp Ala Phe Asn Lys Lys Val Ile Asp Pro Ile Ala Pro Arg His
            500                 505                 510

Thr Ala Ile Val Asn Pro Val Lys Ile His Leu Glu Gly Ser Glu Ala
        515                 520                 525

Pro Gln Glu Pro Lys Ile Glu Met Lys Pro Lys His Lys Lys Asn Pro
    530                 535                 540
```

```
Ala Val Gly Glu Lys Lys Val Ile Tyr Tyr Lys Asp Ile Val Asp
545                 550                 555                 560

Lys Asp Asp Ala Asp Val Ile Asn Val Asp Glu Glu Val Thr Leu Met
                565                 570                 575

Asp Trp Gly Asn Val Ile Ile Thr Lys Lys Asn Asp Asp Gly Ser Met
            580                 585                 590

Val Ala Lys Leu Asn Leu Glu Gly Asp Phe Lys Lys Thr Lys His Lys
            595                 600                 605

Leu Thr Trp Leu Ala Asp Thr Lys Asp Val Val Pro Val Asp Leu Val
610                 615                 620

Asp Phe Asp His Leu Ile Thr Lys Asp Arg Leu Glu Glu Asp Glu Ser
625                 630                 635                 640

Phe Glu Asp Phe Leu Thr Pro Gln Thr Glu Phe His Thr Asp Ala Ile
                645                 650                 655

Ala Asp Leu Asn Val Lys Asp Met Lys Ile Gly Asp Ile Ile Gln Phe
            660                 665                 670

Glu Arg Lys Gly Tyr Tyr Arg Leu Asp Ala Leu Pro Lys Asp Gly Lys
            675                 680                 685

Pro Tyr Val Phe Phe Thr Ile Pro Asp Gly Lys Ser Val Asn Lys Tyr
            690                 695                 700

Gly Ala Lys Lys
705

<210> SEQ ID NO 4
<211> LENGTH: 415
<212> TYPE: PRT
<213> ORGANISM: Saccharomyces cerevisiae

<400> SEQUENCE: 4

Met Ser Gln Gly Thr Leu Tyr Ala Asn Phe Arg Ile Arg Thr Trp Val
1               5                   10                  15

Pro Arg Gly Leu Val Lys Ala Leu Lys Leu Asp Val Lys Val Val Thr
                20                  25                  30

Pro Asp Ala Ala Glu Gln Phe Ala Arg Asp Phe Pro Leu Lys Lys
            35                  40                  45

Val Pro Ala Phe Val Gly Pro Lys Gly Tyr Lys Leu Thr Glu Ala Met
50                  55                  60

Ala Ile Asn Tyr Tyr Leu Val Lys Leu Ser Gln Asp Asp Lys Met Lys
65                  70                  75                  80

Thr Gln Leu Leu Gly Ala Asp Asp Leu Asn Ala Gln Ala Gln Ile
                85                  90                  95

Ile Arg Trp Gln Ser Leu Ala Asn Ser Asp Leu Cys Ile Gln Ile Ala
            100                 105                 110

Asn Thr Ile Val Pro Leu Lys Gly Gly Ala Pro Tyr Asn Lys Lys Ser
            115                 120                 125

Val Asp Ser Ala Met Asp Ala Val Asp Lys Ile Val Asp Ile Phe Glu
130                 135                 140

Asn Arg Leu Lys Asn Tyr Thr Tyr Leu Ala Thr Glu Asn Ile Ser Leu
145                 150                 155                 160

Ala Asp Leu Val Ala Ala Ser Ile Phe Thr Arg Tyr Phe Glu Ser Leu
                165                 170                 175

Phe Gly Thr Glu Trp Arg Ala Gln His Pro Ala Ile Val Arg Trp Phe
            180                 185                 190

Asn Thr Val Arg Ala Ser Pro Phe Leu Lys Asp Glu Tyr Lys Asp Phe
```

```
            195                 200                 205
Lys Phe Ala Asp Lys Pro Leu Ser Pro Gln Lys Lys Glu Lys
    210                 215                 220

Lys Ala Pro Ala Ala Pro Ala Ala Ser Lys Lys Glu Glu Ala
225                 230                 235                 240

Lys Pro Ala Ala Thr Glu Thr Glu Thr Ser Lys Lys Pro Lys His
                245                 250                 255

Pro Leu Glu Leu Leu Gly Lys Ser Thr Phe Val Leu Asp Asp Trp Lys
                260                 265                 270

Arg Lys Tyr Ser Asn Glu Asp Thr Arg Pro Val Ala Leu Pro Trp Phe
            275                 280                 285

Trp Glu His Tyr Asn Pro Glu Glu Tyr Ser Leu Trp Lys Val Thr Tyr
    290                 295                 300

Lys Tyr Asn Asp Glu Leu Thr Leu Thr Phe Met Ser Asn Asn Leu Val
305                 310                 315                 320

Gly Gly Phe Phe Asn Arg Leu Ser Ala Ser Thr Lys Tyr Met Phe Gly
                325                 330                 335

Cys Leu Val Val Tyr Gly Glu Asn Asn Asn Gly Ile Val Gly Ala
                340                 345                 350

Val Met Val Arg Gly Gln Asp Tyr Val Pro Ala Phe Asp Val Ala Pro
            355                 360                 365

Asp Trp Glu Ser Tyr Asp Tyr Ala Lys Leu Asp Pro Thr Asn Asp Asp
    370                 375                 380

Asp Lys Glu Phe Ile Asn Asn Met Trp Ala Trp Asp Lys Pro Val Ser
385                 390                 395                 400

Val Asn Gly Glu Pro Lys Glu Ile Val Asp Gly Lys Val Leu Lys
                405                 410                 415

<210> SEQ ID NO 5
<211> LENGTH: 412
<212> TYPE: PRT
<213> ORGANISM: Saccharomyces cerevisiae

<400> SEQUENCE: 5

Met Ser Gln Gly Thr Leu Tyr Ile Asn Arg Ser Pro Arg Asn Tyr Ala
1               5                   10                  15

Ser Glu Ala Leu Ile Ser Tyr Phe Lys Leu Asp Val Lys Ile Val Asp
                20                  25                  30

Leu Glu Gln Ser Ser Glu Phe Ala Ser Leu Phe Pro Leu Lys Gln Ala
            35                  40                  45

Pro Ala Phe Leu Gly Pro Lys Gly Leu Lys Leu Thr Glu Ala Leu Ala
        50                  55                  60

Ile Gln Phe Tyr Leu Ala Asn Gln Val Ala Asp Glu Lys Glu Arg Ala
65                  70                  75                  80

Arg Leu Leu Gly Ser Asp Val Ile Glu Lys Ser Gln Ile Leu Arg Trp
                85                  90                  95

Ala Ser Leu Ala Asn Ser Asp Val Met Ser Asn Ile Ala Arg Pro Phe
                100                 105                 110

Leu Ser Phe Lys Gly Leu Ile Pro Tyr Asn Lys Lys Asp Val Asp Ala
            115                 120                 125

Cys Phe Val Lys Ile Asp Asn Leu Ala Ala Val Phe Asp Ala Arg Leu
        130                 135                 140

Arg Asp Tyr Thr Phe Val Ala Thr Glu Asn Ile Ser Leu Gly Asp Leu
145                 150                 155                 160
```

His Ala Gly Ser Trp Ala Phe Gly Leu Ala Thr Ile Leu Gly Pro
            165                 170                 175

Glu Trp Arg Ala Lys His Pro His Leu Met Arg Trp Phe Asn Thr Val
        180                 185                 190

Ala Ala Ser Pro Ile Val Lys Thr Pro Phe Ala Glu Val Lys Leu Ala
    195                 200                 205

Glu Lys Ala Leu Thr Tyr Thr Pro Pro Lys Lys Gln Lys Ala Glu Lys
210                 215                 220

Pro Lys Ala Glu Lys Ser Lys Ala Glu Lys Lys Asp Glu Ala Lys
225                 230                 235                 240

Pro Ala Asp Asp Ala Ala Pro Ala Lys Lys Pro Lys His Pro Leu Glu
                245                 250                 255

Ala Leu Gly Lys Ser Thr Phe Val Leu Asp Asp Trp Lys Arg Lys Tyr
            260                 265                 270

Ser Asn Asp Asp Thr Arg Pro Val Ala Leu Pro Trp Phe Trp Glu His
        275                 280                 285

Tyr Asn Pro Glu Glu Tyr Ser Ile Trp Lys Val Gly Tyr Lys Tyr Asn
    290                 295                 300

Asp Glu Leu Thr Leu Thr Phe Met Ser Asn Asn Leu Val Gly Gly Phe
305                 310                 315                 320

Phe Asn Arg Leu Ser Ala Ser Thr Lys Tyr Met Phe Gly Cys Leu Val
                325                 330                 335

Val Tyr Gly Glu Asn Asn Asn Asn Gly Ile Val Gly Ala Val Met Val
            340                 345                 350

Arg Gly Gln Asp Phe Ala Pro Ala Phe Asp Val Ala Pro Asp Trp Glu
        355                 360                 365

Ser Tyr Glu Tyr Thr Lys Leu Asp Pro Thr Lys Glu Glu Asp Lys Glu
    370                 375                 380

Phe Val Asn Asn Met Trp Ala Trp Asp Lys Pro Val Val Asn Gly
385                 390                 395                 400

Glu Asp Lys Glu Ile Val Asp Gly Lys Val Leu Lys
                405                 410

<210> SEQ ID NO 6
<211> LENGTH: 206
<212> TYPE: PRT
<213> ORGANISM: Saccharomyces cerevisiae

<400> SEQUENCE: 6

Met Ala Ser Thr Asp Phe Ser Lys Ile Glu Thr Leu Lys Gln Leu Asn
1               5                   10                  15

Ala Ser Leu Ala Asp Lys Ser Tyr Ile Glu Gly Thr Ala Val Ser Gln
            20                  25                  30

Ala Asp Val Thr Val Phe Lys Ala Phe Gln Ser Ala Tyr Pro Glu Phe
        35                  40                  45

Ser Arg Trp Phe Asn His Ile Ala Ser Lys Ala Asp Glu Phe Asp Ser
    50                  55                  60

Phe Pro Ala Ala Ser Ala Ala Ala Glu Glu Glu Asp Asp
65                  70                  75                  80

Val Asp Leu Phe Gly Ser Asp Glu Glu Ala Asp Ala Glu Ala Glu
                85                  90                  95

Lys Leu Lys Ala Glu Arg Ile Ala Ala Tyr Asn Ala Lys Lys Ala Ala
            100                 105                 110

Lys Pro Ala Lys Pro Ala Ala Lys Ser Ile Val Thr Leu Asp Val Lys
        115                 120                 125

```
Pro Trp Asp Asp Glu Thr Asn Leu Glu Glu Met Val Ala Asn Val Lys
    130                 135                 140
Ala Ile Glu Met Glu Gly Leu Thr Trp Gly Ala His Gln Phe Ile Pro
145                 150                 155                 160
Ile Gly Phe Gly Ile Lys Lys Leu Gln Ile Asn Cys Val Val Glu Asp
                165                 170                 175
Asp Lys Val Ser Leu Asp Asp Leu Gln Gln Ser Ile Glu Glu Asp Glu
            180                 185                 190
Asp His Val Gln Ser Thr Asp Ile Ala Ala Met Gln Lys Leu
        195                 200                 205

<210> SEQ ID NO 7
<211> LENGTH: 1044
<212> TYPE: PRT
<213> ORGANISM: Saccharomyces cerevisiae

<400> SEQUENCE: 7

Met Ser Asp Ser Gln Gln Ser Ile Lys Val Leu Glu Glu Leu Phe Gln
1               5                   10                  15
Lys Leu Ser Val Ala Thr Ala Asp Asn Arg His Glu Ile Ala Ser Glu
            20                  25                  30
Val Ala Ser Phe Leu Asn Gly Asn Ile Ile Glu His Asp Val Pro Glu
        35                  40                  45
His Phe Phe Gly Glu Leu Ala Lys Gly Ile Lys Asp Lys Lys Thr Ala
    50                  55                  60
Ala Asn Ala Met Gln Ala Val Ala His Ile Ala Asn Gln Ser Asn Leu
65                  70                  75                  80
Ser Pro Ser Val Glu Pro Tyr Ile Val Gln Leu Val Pro Ala Ile Cys
                85                  90                  95
Thr Asn Ala Gly Asn Lys Asp Lys Glu Ile Gln Ser Val Ala Ser Glu
            100                 105                 110
Thr Leu Ile Ser Ile Val Asn Ala Val Asn Pro Val Ala Ile Lys Ala
        115                 120                 125
Leu Leu Pro His Leu Thr Asn Ala Ile Val Glu Thr Asn Lys Trp Gln
    130                 135                 140
Glu Lys Ile Ala Ile Leu Ala Ala Ile Ser Ala Met Val Asp Ala Ala
145                 150                 155                 160
Lys Asp Gln Val Ala Leu Arg Met Pro Glu Leu Ile Pro Val Leu Ser
                165                 170                 175
Glu Thr Met Trp Asp Thr Lys Lys Glu Val Lys Ala Ala Ala Thr Ala
            180                 185                 190
Ala Met Thr Lys Ala Thr Glu Thr Val Asp Asn Lys Asp Ile Glu Arg
        195                 200                 205
Phe Ile Pro Ser Leu Ile Gln Cys Ile Ala Asp Pro Thr Glu Val Pro
    210                 215                 220
Glu Thr Val His Leu Leu Gly Ala Thr Thr Phe Val Ala Glu Val Thr
225                 230                 235                 240
Pro Ala Thr Leu Ser Ile Met Val Pro Leu Leu Ser Arg Gly Leu Asn
                245                 250                 255
Glu Arg Glu Thr Gly Ile Lys Arg Lys Ser Ala Val Ile Ile Asp Asn
            260                 265                 270
Met Cys Lys Leu Val Glu Asp Pro Gln Val Ile Ala Pro Phe Leu Gly
        275                 280                 285
Lys Leu Leu Pro Gly Leu Lys Ser Asn Phe Ala Thr Ile Ala Asp Pro
```

```
              290                 295                 300
Glu Ala Arg Glu Val Thr Leu Arg Ala Leu Lys Thr Leu Arg Arg Val
305                 310                 315                 320

Gly Asn Val Gly Glu Asp Ala Ile Pro Glu Val Ser His Ala Gly
            325                 330                 335

Asp Val Ser Thr Thr Leu Gln Val Val Asn Glu Leu Leu Lys Asp Glu
            340                 345                 350

Thr Val Ala Pro Arg Phe Lys Ile Val Glu Tyr Ile Ala Ala Ile
            355                 360                 365

Gly Ala Asp Leu Ile Asp Glu Arg Ile Ile Asp Gln Gln Ala Trp Phe
370                 375                 380

Thr His Ile Thr Pro Tyr Met Thr Ile Phe Leu His Glu Lys Lys Ala
385                 390                 395                 400

Lys Asp Ile Leu Asp Glu Phe Arg Lys Arg Ala Val Asp Asn Ile Pro
            405                 410                 415

Val Gly Pro Asn Phe Asp Asp Glu Glu Asp Glu Gly Glu Asp Leu Cys
            420                 425                 430

Asn Cys Glu Phe Ser Leu Ala Tyr Gly Ala Lys Ile Leu Leu Asn Lys
            435                 440                 445

Thr Gln Leu Arg Leu Lys Arg Ala Arg Arg Tyr Gly Ile Cys Gly Pro
            450                 455                 460

Asn Gly Cys Gly Lys Ser Thr Leu Met Arg Ala Ile Ala Asn Gly Gln
465                 470                 475                 480

Val Asp Gly Phe Pro Thr Gln Glu Glu Cys Arg Thr Val Tyr Val Glu
            485                 490                 495

His Asp Ile Asp Gly Thr His Ser Asp Thr Ser Val Leu Asp Phe Val
            500                 505                 510

Phe Glu Ser Gly Val Gly Thr Lys Glu Ala Ile Lys Asp Lys Leu Ile
            515                 520                 525

Glu Phe Gly Phe Thr Asp Glu Met Ile Ala Met Pro Ile Ser Ala Leu
            530                 535                 540

Ser Gly Gly Trp Lys Met Lys Leu Ala Leu Ala Arg Ala Val Leu Arg
545                 550                 555                 560

Asn Ala Asp Ile Leu Leu Leu Asp Glu Pro Thr Asn His Leu Asp Thr
            565                 570                 575

Val Asn Val Ala Trp Leu Val Asn Tyr Leu Asn Thr Cys Gly Ile Thr
            580                 585                 590

Ser Ile Thr Ile Ser His Asp Ser Val Phe Leu Asp Asn Val Cys Glu
            595                 600                 605

Tyr Ile Ile Asn Tyr Glu Gly Leu Lys Leu Arg Lys Tyr Lys Gly Asn
            610                 615                 620

Phe Thr Glu Phe Val Lys Lys Cys Pro Ala Ala Lys Ala Tyr Glu Glu
625                 630                 635                 640

Leu Ser Asn Thr Asp Leu Glu Phe Lys Phe Pro Glu Pro Gly Tyr Leu
            645                 650                 655

Glu Gly Val Lys Thr Lys Gln Lys Ala Ile Val Lys Val Thr Asn Met
            660                 665                 670

Glu Phe Gln Tyr Pro Gly Thr Ser Lys Pro Gln Ile Thr Asp Ile Asn
            675                 680                 685

Phe Gln Cys Ser Leu Ser Ser Arg Ile Ala Val Ile Gly Pro Asn Gly
            690                 695                 700

Ala Gly Lys Ser Thr Leu Ile Asn Val Leu Thr Gly Glu Leu Leu Pro
705                 710                 715                 720
```

```
Thr Ser Gly Glu Val Tyr Thr His Glu Asn Cys Arg Ile Ala Tyr Ile
            725                 730                 735

Lys Gln His Ala Phe Ala His Ile Glu Ser His Leu Asp Lys Thr Pro
            740                 745                 750

Ser Glu Tyr Ile Gln Trp Arg Phe Gln Thr Gly Glu Asp Arg Glu Thr
            755                 760                 765

Met Asp Arg Ala Asn Arg Gln Ile Asn Glu Asn Asp Ala Glu Ala Met
        770                 775                 780

Asn Lys Ile Phe Lys Ile Glu Gly Thr Pro Arg Arg Ile Ala Gly Ile
785                 790                 795                 800

His Ser Arg Arg Lys Phe Lys Asn Thr Tyr Glu Tyr Glu Cys Ser Phe
            805                 810                 815

Leu Leu Gly Glu Asn Ile Gly Met Lys Ser Glu Arg Trp Val Pro Met
            820                 825                 830

Met Ser Val Asp Asn Ala Trp Ile Pro Arg Gly Glu Leu Val Glu Ser
            835                 840                 845

His Ser Lys Met Val Ala Glu Val Asp Met Lys Glu Ala Leu Ala Ser
            850                 855                 860

Gly Gln Phe Arg Pro Leu Thr Arg Lys Glu Ile Glu Glu His Cys Ser
865                 870                 875                 880

Met Leu Gly Leu Asp Pro Glu Ile Val Ser His Ser Arg Ile Arg Gly
            885                 890                 895

Leu Ser Gly Gly Gln Lys Val Lys Leu Val Leu Ala Ala Gly Thr Trp
            900                 905                 910

Gln Arg Pro His Leu Ile Val Leu Asp Glu Pro Thr Asn Tyr Leu Asp
            915                 920                 925

Arg Asp Ser Leu Gly Ala Leu Ser Lys Ala Leu Lys Glu Phe Glu Gly
            930                 935                 940

Gly Val Ile Ile Thr His Ser Ala Glu Phe Thr Lys Asn Leu Thr
945                 950                 955                 960

Glu Glu Val Trp Ala Val Lys Asp Gly Arg Met Thr Pro Ser Gly His
            965                 970                 975

Asn Trp Val Ser Gly Gln Gly Ala Gly Pro Arg Ile Glu Lys Lys Glu
            980                 985                 990

Asp Glu Glu Asp Lys Phe Asp Ala Met Gly Asn Lys Ile Ala Gly Gly
            995                 1000                1005

Lys Lys  Lys Lys Lys Leu Ser  Ser Ala Glu Leu Arg  Lys Lys Lys
            1010                1015                1020

Lys Glu  Arg Met Lys Lys Lys  Lys Glu Leu Gly Asp  Ala Tyr Val
            1025                1030                1035

Ser Ser  Asp Glu Glu Phe
            1040

<210> SEQ ID NO 8
<211> LENGTH: 579
<212> TYPE: PRT
<213> ORGANISM: Saccharomyces cerevisiae

<400> SEQUENCE: 8

Met Lys Tyr Val Val Ser Gly Gly Val Ile Ser Gly Ile Gly Lys
1               5                   10                  15

Gly Val Leu Ala Ser Ser Thr Gly Met Leu Met Lys Thr Leu Gly Leu
            20                  25                  30

Lys Val Thr Ser Ile Lys Ile Asp Pro Tyr Met Asn Ile Asp Ala Gly
```

```
                35                  40                  45
Thr Met Ser Pro Leu Glu His Gly Glu Cys Phe Val Leu Asp Asp Gly
 50                  55                  60

Gly Glu Thr Asp Leu Asp Leu Gly Asn Tyr Glu Arg Tyr Leu Gly Val
 65                  70                  75                  80

Thr Leu Thr Lys Asp His Asn Ile Thr Thr Gly Lys Ile Tyr Ser His
                 85                  90                  95

Val Ile Ala Lys Glu Arg Lys Gly Asp Tyr Leu Gly Lys Thr Val Gln
                100                 105                 110

Ile Val Pro His Leu Thr Asn Ala Ile Gln Asp Trp Ile Glu Arg Val
                115                 120                 125

Ala Lys Ile Pro Val Asp Asp Thr Gly Met Glu Pro Asp Val Cys Ile
130                 135                 140

Ile Glu Leu Gly Gly Thr Val Gly Asp Ile Glu Ser Ala Pro Phe Val
145                 150                 155                 160

Glu Ala Leu Arg Gln Phe Gln Phe Lys Val Gly Lys Glu Asn Phe Ala
                165                 170                 175

Leu Ile His Val Ser Leu Val Pro Val Ile His Gly Glu Gln Lys Thr
                180                 185                 190

Lys Pro Thr Gln Ala Ala Ile Lys Gly Leu Arg Ser Leu Gly Leu Val
                195                 200                 205

Pro Asp Met Ile Ala Cys Arg Cys Ser Glu Thr Leu Asp Lys Pro Thr
210                 215                 220

Ile Asp Lys Ile Ala Met Phe Cys His Val Gly Pro Glu Gln Val Val
225                 230                 235                 240

Asn Val His Asp Val Asn Ser Thr Tyr His Val Pro Leu Leu Leu Leu
                245                 250                 255

Glu Gln Lys Met Ile Asp Tyr Leu His Ala Arg Leu Lys Leu Asp Glu
                260                 265                 270

Ile Ser Leu Thr Glu Glu Lys Gln Arg Gly Leu Glu Leu Leu Ser
                275                 280                 285

Lys Trp Lys Ala Thr Thr Gly Asn Phe Asp Glu Ser Met Glu Thr Val
290                 295                 300

Lys Ile Ala Leu Val Gly Lys Tyr Thr Asn Leu Lys Asp Ser Tyr Leu
305                 310                 315                 320

Ser Val Ile Lys Ala Leu Glu His Ser Ser Met Lys Cys Arg Arg Lys
                325                 330                 335

Leu Asp Ile Lys Trp Val Glu Ala Thr Asp Leu Glu Pro Glu Ala Gln
                340                 345                 350

Glu Ser Asn Lys Thr Lys Phe His Glu Ala Trp Asn Met Val Ser Thr
                355                 360                 365

Ala Asp Gly Ile Leu Ile Pro Gly Gly Phe Gly Val Arg Gly Thr Glu
370                 375                 380

Gly Met Val Leu Ala Ala Arg Trp Ala Arg Glu Asn His Ile Pro Phe
385                 390                 395                 400

Leu Gly Val Cys Leu Gly Leu Gln Ile Ala Thr Ile Glu Phe Thr Arg
                405                 410                 415

Ser Val Leu Gly Arg Lys Asp Ser His Ser Ala Glu Phe Tyr Pro Asp
                420                 425                 430

Ile Asp Glu Lys Asn His Val Val Phe Met Pro Glu Ile Asp Lys
                435                 440                 445

Glu Thr Met Gly Gly Ser Met Arg Leu Gly Leu Arg Pro Thr Phe Phe
450                 455                 460
```

```
Gln Asn Glu Thr Glu Trp Ser Gln Ile Lys Lys Leu Tyr Gly Asp Val
465                 470                 475                 480

Ser Glu Val His Glu Arg His Arg His Arg Tyr Glu Ile Asn Pro Lys
                485                 490                 495

Met Val Asp Glu Leu Glu Asn Asn Gly Leu Ile Phe Val Gly Lys Asp
            500                 505                 510

Asp Thr Gly Lys Arg Cys Glu Ile Leu Glu Leu Lys Asn His Pro Tyr
        515                 520                 525

Tyr Ile Ala Thr Gln Tyr His Pro Glu Tyr Thr Ser Lys Val Leu Asp
    530                 535                 540

Pro Ser Lys Pro Phe Leu Gly Leu Val Ala Ala Ser Ala Gly Ile Leu
545                 550                 555                 560

Gln Asp Val Ile Glu Gly Lys Tyr Asp Leu Glu Ala Gly Glu Asn Lys
                565                 570                 575

Phe Asn Phe
```

<210> SEQ ID NO 9
<211> LENGTH: 191
<212> TYPE: PRT
<213> ORGANISM: Saccharomyces cerevisiae

<400> SEQUENCE: 9

```
Met Pro Ser Thr Leu Thr Ile Asn Gly Lys Ala Pro Ile Val Ala Tyr
1               5                   10                  15

Ala Glu Leu Ile Ala Ala Arg Ile Val Asn Ala Leu Ala Pro Asn Ser
            20                  25                  30

Ile Ala Ile Lys Leu Val Asp Asp Lys Lys Ala Pro Ala Ala Lys Leu
        35                  40                  45

Asp Asp Ala Thr Glu Asp Val Phe Asn Lys Ile Thr Ser Lys Phe Ala
    50                  55                  60

Ala Ile Phe Asp Asn Gly Asp Lys Glu Gln Val Ala Lys Trp Val Asn
65                  70                  75                  80

Leu Ala Gln Lys Glu Leu Val Ile Lys Asn Phe Ala Lys Leu Ser Gln
                85                  90                  95

Ser Leu Glu Thr Leu Asp Ser Gln Leu Asn Leu Arg Thr Phe Ile Leu
            100                 105                 110

Gly Gly Leu Lys Tyr Ser Ala Ala Asp Val Ala Cys Trp Gly Ala Leu
        115                 120                 125

Arg Ser Asn Gly Met Cys Gly Ser Ile Ile Lys Asn Lys Val Asp Val
    130                 135                 140

Asn Val Ser Arg Trp Tyr Thr Leu Leu Glu Met Asp Pro Ile Phe Gly
145                 150                 155                 160

Glu Ala His Asp Phe Leu Ser Lys Ser Leu Leu Glu Leu Lys Lys Ser
                165                 170                 175

Ala Asn Val Gly Lys Lys Lys Glu Thr His Lys Ala Asn Phe Glu
            180                 185                 190
```

<210> SEQ ID NO 10
<211> LENGTH: 207
<212> TYPE: PRT
<213> ORGANISM: Saccharomyces cerevisiae

<400> SEQUENCE: 10

```
Met Ser Phe Leu Ile Ser Phe Asp Lys Ser Lys Lys His Pro Ala His
1               5                   10                  15
```

```
Leu Gln Leu Ala Asn Asn Leu Lys Ile Ala Leu Ala Leu Glu Tyr Ala
             20                  25                  30

Ser Lys Asn Leu Lys Pro Glu Val Asp Asn Asp Asn Ala Ala Met Glu
         35                  40                  45

Leu Arg Asn Thr Lys Glu Pro Phe Leu Leu Phe Asp Ala Asn Ala Ile
 50                  55                  60

Leu Arg Tyr Val Met Asp Asp Phe Glu Gly Gln Thr Ser Asp Lys Tyr
 65                  70                  75                  80

Gln Phe Ala Leu Ala Ser Leu Gln Asn Leu Tyr His Lys Glu Leu
                 85                  90                  95

Pro Gln Gln His Val Glu Val Leu Thr Asn Lys Ala Ile Glu Asn Tyr
             100                 105                 110

Leu Val Glu Leu Lys Glu Pro Leu Thr Thr Thr Asp Leu Ile Leu Phe
             115                 120                 125

Ala Asn Val Tyr Ala Leu Asn Ser Ser Leu Val His Ser Lys Phe Pro
             130                 135                 140

Glu Leu Pro Ser Lys Val His Asn Ala Val Ala Leu Ala Lys Lys His
145                 150                 155                 160

Val Pro Arg Asp Ser Ser Ser Phe Lys Asn Ile Gly Ala Val Lys Ile
                 165                 170                 175

Gln Ala Asp Leu Thr Val Lys Pro Lys Asp Ser Glu Ile Leu Pro Lys
             180                 185                 190

Pro Asn Glu Arg Asn Ile Leu Ile Thr Ser Ala Leu Pro Tyr Val
             195                 200                 205

<210> SEQ ID NO 11
<211> LENGTH: 156
<212> TYPE: PRT
<213> ORGANISM: Saccharomyces cerevisiae

<400> SEQUENCE: 11

Met Ser Gln Gly Thr Leu Tyr Ile Asn Arg Ser Pro Arg Asn Tyr Ala
1               5                   10                  15

Ser Glu Ala Leu Ile Ser Tyr Phe Lys Leu Asp Val Lys Ile Val Asp
             20                  25                  30

Leu Glu Gln Ser Ser Glu Phe Ala Ser Leu Phe Pro Leu Lys Gln Ala
             35                  40                  45

Pro Ala Phe Leu Gly Pro Lys Gly Leu Lys Leu Thr Glu Ala Leu Ala
         50                  55                  60

Ile Gln Phe Tyr Leu Ala Asn Gln Val Ala Asp Glu Lys Glu Arg Ala
65                  70                  75                  80

Arg Leu Leu Gly Ser Asp Val Ile Glu Lys Ser Gln Ile Leu Arg Trp
                 85                  90                  95

Ala Ser Leu Ala Asn Ser Asp Val Met Ser Asn Ile Ala Arg Pro Phe
             100                 105                 110

Leu Ser Phe Lys Gly Leu Ile Pro Tyr Asn Lys Lys Asp Val Asp Ala
             115                 120                 125

Cys Phe Val Lys Ile Asp Asn Leu Ala Ala Val Phe Asp Ala Arg Leu
             130                 135                 140

Arg Asp Tyr Thr Phe Val Ala Thr Glu Asn Ile Ser
145                 150                 155

<210> SEQ ID NO 12
<211> LENGTH: 159
<212> TYPE: PRT
<213> ORGANISM: Saccharomyces cerevisiae
```

<400> SEQUENCE: 12

Met Ser Gln Gly Thr Leu Tyr Ala Asn Phe Arg Ile Arg Thr Trp Val
1               5                   10                  15

Pro Arg Gly Leu Val Lys Ala Leu Lys Leu Asp Val Lys Val Val Thr
            20                  25                  30

Pro Asp Ala Ala Ala Glu Gln Phe Ala Arg Asp Phe Pro Leu Lys Lys
        35                  40                  45

Val Pro Ala Phe Val Gly Pro Lys Gly Tyr Lys Leu Thr Glu Ala Met
    50                  55                  60

Ala Ile Asn Tyr Tyr Leu Val Lys Leu Ser Gln Asp Asp Lys Met Lys
65                  70                  75                  80

Thr Gln Leu Leu Gly Ala Asp Asp Leu Asn Ala Gln Ala Gln Ile
                85                  90                  95

Ile Arg Trp Gln Ser Leu Ala Asn Ser Asp Leu Cys Ile Gln Ile Ala
                100                 105                 110

Asn Thr Ile Val Pro Leu Lys Gly Gly Ala Pro Tyr Asn Lys Lys Ser
            115                 120                 125

Val Asp Ser Ala Met Asp Ala Val Asp Lys Ile Val Asp Ile Phe Glu
    130                 135                 140

Asn Arg Leu Lys Asn Tyr Thr Tyr Leu Ala Thr Glu Asn Ile Ser
145                 150                 155

<210> SEQ ID NO 13
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 13

Arg Gly Ser Ile Asp Thr Trp Val
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Glu Glu Trp Glu Thr Trp Val
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 15

Tyr Pro Tyr Asp Val Pro Asp Tyr Ala
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic Peptide

```
<400> SEQUENCE: 16

Glu Gln Lys Leu Ile Ser Glu Glu Asp Leu
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 17

Asp Tyr Lys Asp Asp Asp Asp Lys
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 18

Asp Asp Asp Asp Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

Glu Asn Leu Tyr Phe Gln Ser
1               5
```

HEAT-INDUCIBLE SELF-ASSEMBLING PROTEIN DOMAINS

CROSS-REFERENCE TO RELATED APPLICATIONS

This application is a national phase application under 35 U.S.C. § 371 of International Application No. PCT/US2015/057139 filed Oct. 23, 2015, which claims the benefit of priority of U.S. Provisional Patent Application No. 62/068,390, filed Oct. 24, 2014. The entire contents of each of the above-referenced disclosures are specifically incorporated herein by reference without disclaimer.

BACKGROUND OF THE INVENTION

A. Field of the Invention

The invention generally concerns molecular biology and protein engineering. In particular, it involves proteins that are able to self-assemble in a heat-inducible fashion.

B. Description of Related Art

In many scientific applications, conjugation of molecules to larger albeit still microscopic particles (e.g., spheres, beads, rods, nanoparticles) is used to immobilize, control, partition, or otherwise manipulate other molecules. Sigma-Aldrich, Thermo Fisher Scientific, and many other companies sell particles made of sepharose, agarose, or other polymers which either come pre-conjugated with molecules (for example, antibodies, peptides, protein A, streptavidin, biotin) or can be conjugated by the customer using cross-linking chemistry. These particles can also be magnetic, allowing their rapid removal with a magnet.

Genetically encodable, heat-inducible, particle-forming protein domain would be valuable, as it would allow genetic engineering techniques that are now commonplace to be used to construct conjugated particles.

SUMMARY OF THE INVENTION

The present application provides heat-inducible, self-assembling protein domains and fusion proteins including such domains that can be used in many different applications described herein. For example, fusion proteins incorporating a self-assembly domain and a target protein provide improved, rapid purification methods. Such fusion proteins can be genetically encoded, expressed, and purified using conventional laboratory techniques. The fusion proteins can form protein aggregates upon heat induction, and can be used in the place of beads or other conjugated particles in many laboratory protocols.

Proteins containing a self-assembly domain form insoluble aggregates rapidly upon heat treatment, but are essentially absent and soluble at temperatures at or below 30° C., including room temperature. A self-assembly domain, fused to other proteins, confers self-assembling ability on these proteins. Folded proteins retain function within the assembled protein aggregates, and RNA, DNA, and small molecules can be stably bound within the assembled protein aggregates.

Disclosed herein is a self-assembling fusion protein comprising: (a) a heat-inducible self-assembly domain; and (b) a target protein; wherein the self-assembly domain remains folded (at least partially or mostly) during assembly. In some embodiments, the fusion protein is capable of self-assembling into protein aggregates by being heated to a temperature of between about 35 and 50° C. or any range derivable therein. In some embodiments, the heat induction is at a temperature greater than, less than, or between any two of about 35, 36, 37, 38, 39, 40, 41, 42, 43, 44, 45, 46, 47, 48, 49, 50, 51, 52, 53, 54, and 55° C.

In some embodiments of the disclosure, the fusion protein forms aggregates in less than or exactly 1200, 1100, 1000, 900, 800, 700, 600, 500, 400, 300, 275, 250, 225, 200, 175, 150, 125, 100, 75, 60, or 30 seconds upon heat induction, or any derivable range therein.

In some embodiments, the self-assembly domain is a GST-like domain or a polypeptide with at least 90% identity to a GST-like domain. A GST-like domain refers to a conserved protein domain known in the art as a Glutathione S-transferase C-terminal-like domain. This conserved domain is described in the NCBI database of conserved domains (See also Marchler-Bauer A. et al. (2013), "CDD: conserved domains and protein three-dimensional structure." Nucleic Acids Res. 41(D1):D384-52), which is hereby incorporated by reference. Furthermore, a protein can be determined to have this conserved domain by inputting the protein sequence into the NCBI conserved domain database, which can be found on the world wide web at ncbi.nlm.nih.gov/Structure/cdd/wrpsb.cgi. The domain is capable of making stable protein-protein interactions between itself and another GST-like domain, in one of two orientations, as shown in Simader H et al. (2006), "Structural basis of yeast aminoacyl-tRNA synthetase complex formation revealed by crystal structures of two binary sub-complexes," Nucleic Acids Res. 34(14):3968-79.

The term "identity," "homology" or "similarity" refers to sequence similarity between two peptides or between two nucleic acid molecules. A degree of identity can be determined by comparing a position in each sequence which may be aligned for purposes of comparison. When a position in the compared sequence is occupied by the same base or amino acid, then the molecules are homologous at that position. A degree of identity between sequences is a function of the number of matching positions shared by the sequences. An "unrelated" or "non-homologous" sequence shares less than 40% identity, though preferably less than 25% identity, with one of the sequences of the present invention. The percent identity can be calculated by the formula: (Matches×100)/Length of aligned region (with gaps). Note that only internal gaps are included in the length, and not gaps at the sequence ends.

A polynucleotide or polynucleotide region (or a polypeptide or polypeptide region) having a certain percentage (for example, 60%, 65%, 70%, 75%, 80%, 85%, 90%, 95%, 98% or 99%, or any range derivable therein) of "sequence identity" or "homology" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology.

In some embodiments, a polypeptide may have at least 65, 70, 75, 80, 85, 90, 95, 96, 97, 98, 99, or 100% identity (or any range derivable thereof) with another polypeptide.

In some embodiments, the self-assembly domain comprises a polypeptide from Arc1, Mes1, Gus1, or a polypeptide with at least 90% identity to Arc1, Mes1, or Gus1. Arc1, Mes1, and Gust are proteins with GST-like domains. In some embodiments, the self-assembly domain comprises a polypeptide that is at least 20 amino acids in length and has at least 90% identity to the first 250 amino acids to Arc1, Mes1, or Gus1. In this case, the percent identity is calculated specifically as described above, wherein the sequence is aligned, and internal gaps are used to calculate sequence identity, but gaps at the end of the alignment are not used in calculating sequence identity. In some embodiments, the self-assembly domain comprises a polypeptide that is at least 20, 30, 40, 50, 60, 70, 80, 90, 100, 110, 120, 130, 140, 150, 160, 170, 180, 190, or 200 amino acids in length and has at least 90% identity to a polypeptide of similar or the same length from the first 250 amino acids to Arc1, Mes1, or Gus1. In some embodiments, the self-assembly domain comprises a polypeptide that is at least 10, 20, 30, 40, 50, 60, 70, 80, 90, 100, 110, 120, 130, 140, 150, 160, 170, 180, 190, or 200 amino acids in length, or any derivable range thereof. The polypeptide may have a certain degree of identity to the first (N-terminus) 50, 75, 100, 125, 150, 175, 191, 200, 225, 250, 300, or 300 amino acids (or any derivable range thereof) of Arc1, Mes1, or Gus1. In some embodiments, the self-assembly domain comprises a polypeptide from Gus1 or a polypeptide with at least 90, 95, 97, or 99% identity (or any range derivable thereof) to Gus1.

In some embodiments, the self-assembly domain comprises a polypeptide from Tef3, Tef4, Efb1, or a polypeptide with at least 90% identity to Tef3, Tef4, or Efb1. Tef3, Tef4, and Efb1 are proteins with GST-like domains. In some embodiments, the self-assembly domain comprises a polypeptide that is at least 20 amino acids in length and has at least 90% identity to 20 amino acids of the first 250 amino acids from Tef3, Tef4, or Efb1. In this case, the percent identity is calculated specifically as described above, wherein the sequence is aligned, and internal gaps are used to calculate sequence identity, but gaps at the end of the alignment are not used in calculating sequence identity. In some embodiments, the self-assembly domain comprises a polypeptide that is at least 20, 30, 40, 50, 60, 70, 80, 90, 100, 110, 120, 130, 140, 150, 160, 170, 180, 190, or 200 amino acids in length (or any range derivable therein) and has at least 90% identity to a polypeptide of similar or the same length from the first 250 amino acids of Tef3, Tef4, or Efb1. In some embodiments, the self-assembly domain comprises a polypeptide that is at least 10, 20, 30, 40, 50, 60, 70, 80, 90, 100, 110, 120, 130, 140, 150, 160, 170, 180, 190, or 200 amino acids in length, or any derivable range thereof. The polypeptide may have a certain degree of identity to the first (N-terminus) 50, 75, 100, 125, 150, 175, 191, 200, 225, 250, 300, or 300 amino acids (or any derivable range thereof) of Tef3, Tef4, or Efb1.

In some embodiments, the self-assembly domain comprises a polypeptide from Yef3, Ura7, or a polypeptide with at least 90% identity to Yef3 or Ura7.

In some embodiments, the polypeptide is from a *Saccharomyces cerevisiae* protein. In some embodiments, the polypeptide of the assembly domain is from a homolog of Arc1, Mes1, Gus1, Tef3, Tef4, Efb1, Yef3, or Ura7 from another organism. For example, the polypeptide may be a homolog of Arc1, Mes1, Gus1, Tef3, Tef4, Efb1, Yef3, or Ura7 from *B. dendrobatidis, U. hordei, U. maydis, S. reilianum, P. triticina, P. graminis, W. sebi, M. globosa, M. larici-populi, F. radiculosa, P. indica, S. lacrymans, C. cinerea, P. carnosa, A. bisporus, Allavus, C. neoformans, C. gattii, A. oligospora, Lelongisporus, N. tetrasperma, C. parapsilosis, C. albicans, D. hansenii, C. dubliniensis, C. lusitaniae, P. sorbitophila, R. delemar, T. melanosporum, P. pastoris, S. stipitis, S. japonicus, C. tenuis, W. ciferrii, P. angusta, T. stipitatus, S. pombe, A. terreus, N. fumigata, P. marneffei, N. fischeri, A. clavatus, A. oryzae, P. digitatum, P. chrysogenum, A. niger, A. kawachii, T. verrucosum, N. dairenensis, P. brasiliensis, A. benhamiae, A. capsulata, A. gypseum, K. lactis, N. castellii, A. dermatitidis, T. rubrum, T. equinum, S. arboricola, S. cerevisiae, T. blattae, K. naganishii, C. posadasii, A. gossypii, V. polyspora, T. phaffii, A. otae, Z. rouxii, T. delbrueckii, K. africana, C. glabrata, L. thermotoleran, Y. lipolytica, E. aedis, C. militaris, U. reesii, P. firoveci, E. nidulans, T. tonsurans, T. asahii, S. commune, L. maculans, P. teres, N. sp., N. parisii, E. hellem, E. cuniculi, E. romaleae, E. intestinalis, P. tritici-repen, C. globosum, T. terrestris, G. clavigera, T. heterothallic, B. bassiana, M. phaseolina, V. corneae, C. thermophilum, N. crassa, M. oryzae, G. graminis, H. atroviridis, H. vixens, Hjecorina, V. culicis, T. hominis, S. sclerotiorum, B. fuckeliana, N. haematococca, M. robertsii, E. bieneusi, M. acridum, F. oxysporum, C. graminicola, C. gloeosporioid, G. destructans, G. lozoyensis, C. higginsianum, M. brunnea, V. dahliae, F. pseudogramine, S. macrospora, N. ceranae, V. albo-atrum, S. passalidarum, C. tropicalis, M. guilliermond,* or *E. dermatitidis.*

The systematic name and common name of proteins that are useful for the self-assembly domain are:

| Systematic Name | Common Name |
| --- | --- |
| YGL105W | Arc1 |
| YGR264C | Mes1 |
| YGL245W | Gus1 |
| YPL048W | Tef3 |
| YKL081W | Tef4 |
| YAL003W | Efb1 |
| YLR249W | Yef3 |
| YBL039C | Ura7 |

In some embodiments, the self-assembly domain comprises a polypeptide of SEQ ID NO:9, 10, 11, or 12, a fragment thereof, or a polypeptide with at least 90% identity to SEQ ID NO:9, 10, 11, or 12, or a fragment thereof. SEQ ID NOs:9-12 represents the N-terminal GST-like domains of Gus1, Mes1, Tef4, and Tef3.

In some embodiments, the majority of the fusion protein molecules aggregate to form direct protein-protein interactions with other fusion protein molecules upon heat-induction. "Direct" protein-protein interactions are not mediated by solvent or any other molecule, but involve the direct non-covalent interaction of amino acids with other amino acids. Theses direct interactions may be aromatic-aromatic, cation-aromatic, electrostatic, van der Walls, or hydrophobic interactions. The fusion protein is capable of forming the protein aggregates under relatively "mild" conditions, which is one way that the protein aggregates described herein are more useful than other types of protein aggregates for laboratory applications such as forming aggregates conjugated to target proteins, which aggregates can be used in the place of beads or solid substrates in many laboratory protocols. The term "aggregate" in the prior art may refer to mis-folded proteins under denaturing conditions (e.g., elevated temperatures, pH, high salt content). However, the term "protein aggregates," as used herein, is not meant to refer to mis-folded protein, but instead refers to protein that substantially retains a tertiary structure, but associates with the self-assembly domain of any other proteins in the composition. The self-assembly domain, while aggregated, substantially retains function and a tertiary structure. While the self-assembly domain does undergo a conformational change after a temperature shift, the self-assembly domain is not mis-folded at the temperature shift and substantially retains a tertiary structure. Therefore, in some embodiments, the self-assembly domain remains folded at a temperature below, above, or any range derivable thereof, of 60, 55, 50, 45, 40, 35, 30, 25, or 20° C. In some embodiments, the self-assembly domain remains folded at a temperature range of 20–50° C.

In some embodiments, the self-assembly domain is not an elastin-like polymer (ELP), does not have a significant degree of homology to an ELP, and/or does not comprise an ELP polypeptide or fragment.

In some embodiments, the fusion proteins do not self-assemble at temperatures below about 35° C. In some embodiments, the fusion proteins do not self-assemble at temperatures below about 40, 35, 30, 25, 20, or 15° C. (or any range derivable therein).

In some embodiments, the self-assembly domain is at least, at most, or exactly 15, 25, 50, 75, 100, 125, 150, 175, 200, 225, 250, 300, 350, 400, 500, 600, 700, 800, 900, and 1000 amino acids in length, or any range derivable therein.

In some embodiments, the target protein or polypeptide is at least, at most, or exactly 5, 10, 15, 25, 50, 75, 100, 125, 150, 175, 200, 225, 250, 300, 350, 400, 500, 600, 700, 800, 900, and 1000 amino acids in length, or any range derivable therein.

The target protein may be a protein in which purification is desired or may be a component of an assay, such as an antibody or protease. In some embodiments, the target protein is ferritin, a fluorescent protein, an antibody, an antibody fragment, protein A, streptavidin, protein G, protein A/G, protein L, a protease, or StrepTactin. In some embodiments, the target protein is a protease. In some embodiments, the target protein is a wild-type or mutant protein from a eukaryote or a prokaryote. In some embodiments, the target protein is not a naturally occurring protein.

In some embodiments, the fusion protein further comprises a protease cleavage site. In some embodiments, the protease cleavage site is between the target protein and the self-assembly domain.

Further aspects of the disclosure relate to a protein aggregate comprising the fusion protein described herein. In some embodiments, the protein aggregate further comprises a nucleic acid or protein that is specifically bound to the target protein. In some embodiments, a small molecule is specifically bound to the target protein. Further aspects relate to an aqueous composition comprising the fusion protein or the protein aggregate described herein.

In some embodiments, the protein aggregate is in an aqueous composition, wherein the aqueous composition comprises between about 0 and 500 mM KCl or NaCl, or is about or is less than any one of or between any two of about 50, 100, 150, 200, 250, 300, 350, 400, 450, and 500 mM KCl or NaCl. In some embodiments, the aqueous composition does not include alcohol. In some embodiments the fusion protein is present in the aqueous composition at a concentration of between about 5 and 50 µM, or at a concentration of less than any one of or between any two of about 5, 10, 15, 20, 25, 30, 35, 40, 45, and 50 µM. In some embodiments, the fusion protein is at least 55% pure, or is at least between any two of about 55, 60, 65, 70, 75, 80, 85, 90, 95, 98, 99, and 99.9% pure in the aqueous solution. In some embodiments, the pH of the aqueous composition is between about 6.0 and 8.0, or is about or is greater than, less than, or between any two of about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0.

In some embodiments, the target protein in the fusion proteins described above is a restriction enzyme, DNA polymerase, protease, ligase, RNA polymerase, methylase, polyadenylate polymerase, topoisomerase, guanylyl transferase, ribonuclease, deoxyribonuclease, alkaline phosphatase, polynucleotide kinase or reverse transcriptase. In some embodiments, the target protein is a therapeutic protein.

Further aspects of the disclosure relate to a polynucleotide coding for the fusion protein described herein. Other embodiments of the disclosure relate to a host cell comprising the fusion protein or the polynucleotide described herein. Yet further aspects relate to cell lysate comprising the fusion protein as described herein.

Also disclosed is a method for aggregating a target protein comprising: formulating an aqueous composition comprising the fusion protein as described herein; and heating the composition to a temperature between about 35 and 50° C. or any range derivable therein. In some embodiments, the temperature is above, below, or a derivable range of about 20, 25, 30, 35, 40, 45, 50, 55, or 60° C.

Further method aspects of the disclosure relate to a method of selectively depleting a molecule from an aqueous composition comprising: formulating an aqueous composition comprising the molecule and the fusion protein as described herein, wherein the target protein is a protein that specifically binds to the molecule; heating the aqueous composition to a temperature between about 35 and 50° C. to form protein aggregates comprising the fusion protein and the molecule; and removing the protein aggregates from the aqueous composition. In some embodiments, the temperature is above, below, or a derivable range of about 20, 25, 30, 35, 40, 45, 50, 55, or 60° C. In some embodiments, the molecule is a nucleic acid. The molecule may be, for example, a DNA or a RNA. In some embodiments, removing the protein aggregates from the aqueous composition is performed by centrifuging or filtering the aqueous composition.

Further method aspects of the disclosure relate to a method of selectively depleting a molecule from an aqueous composition comprising: heating the aqueous composition comprising the fusion protein to a temperature between about 35 and 50° C. to form protein aggregates comprising the fusion protein; adding the molecule to the aqueous composition comprising the aggregated fusion protein, wherein the target protein is a protein that specifically binds to the molecule; and removing the protein aggregates from the aqueous composition. In some embodiments, the temperature is above, below, or a derivable range of about 20, 25, 30, 35, 40, 45, 50, 55, or 60° C. In some embodiments, the molecule is a nucleic acid. The molecule may be, for example, a DNA or a RNA. In some embodiments, removing the protein aggregates from the aqueous composition is performed by centrifuging or filtering the aqueous composition.

The removal or separation of the protein aggregates may be done by methods known in the art for separating soluble and insoluble (protein aggregates) fractions. These include, for example, centrifugation, filtration, and size exclusion chromatography.

Other aspects relate to a method of immunoprecipitating a molecule comprising: formulating an aqueous composition comprising the molecule and the fusion protein of any one of claims 1-20; wherein the target protein is an antibody or antigen binding fragment that specifically binds to the molecule; and heating the aqueous composition to a temperature between about 35 and 50° C. to form protein aggregates comprising the fusion protein and the molecule. In some embodiments, the temperature is above, below, or a derivable range of 20, 25, 30, 35, 40, 45, 50, 55, or 60° C.

In some embodiments, the method further comprises detecting the molecule bound in the protein aggregate. In some embodiments, the method further comprises quantifying the molecule bound in the protein aggregate. In some embodiments, the method further comprises separating the protein aggregates from the soluble composition.

Further method aspects relate to a method for purifying a protein comprising: formulating an aqueous composition comprising a fusion protein as described herein; heating the aqueous composition to a temperature between about 35 and 50° C. to form protein aggregates comprising the fusion protein; and separating the protein aggregates from the aqueous composition. In some embodiments, the temperature is above, below, or a derivable range of 20, 25, 30, 35, 40, 45, 50, 55, or 60° C. In some embodiments, the fusion protein is a first fusion protein comprising a protein cleavage site between the self-assembly domain and the target protein. In some embodiments, the method further comprises: cleaving the first fusion protein by formulating an aqueous composition comprising a second fusion protein and the first fusion protein in the separated aggregate; wherein the target protein of the second fusion protein is a protease that cleaves the first fusion protein at the protein cleavage site between the self-assembly domain and the target protein of the first fusion protein; heating the aqueous composition to a temperature between about 35 and 50° C. to form protein aggregates comprising the second fusion protein and the self-assembly domain of the cleaved first fusion protein; wherein the target protein of the first fusion protein remains soluble; and separating the protein aggregates from the soluble target protein of the first fusion protein. This purification method is further described in the figures and examples.

Further aspects relate to a method of immunoprecipitating or purifying a molecule comprising the steps of: formulating a first composition comprising the fusion protein as described herein; wherein the target protein is a first target protein that specifically binds to the molecule; heating the first composition to a temperature between about 35 and 50° C. to form protein aggregates comprising the fusion protein; and contacting the first composition with a second composition comprising the molecule. In some embodiments, the first target protein that specifically binds to the molecule is an antibody, an antigen binding fragment, or an affinity tag (e.g., PDZ domain). In some embodiments, the composition is heated to at least, at most, or exactly about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, or 70° C., or any derivable range therein. In some embodiments, the heating of the composition is done prior to contacting of the first composition with the second composition. In some embodiments, the heating of the first composition is done after contacting the first composition with the second composition. In some embodiments, the second composition maintains a temperature of less than 40° C. throughout the method. In some embodiments, the second composition and/or second target protein maintains a temperature of less than 45, 44, 43, 42, 41, 40, 39, 38, 37, 36, 35, 34, 33, 32, 31, 30, 29, 28, 27, 26, 25, 24, 23, 22, 21, or 20° C. throughout the method. In some embodiments, contacting the first composition with the second composition comprises mixing the compositions. The mixing may be done by mechanical means such as, for example, vortexing, pipetting, etc. In some embodiments, the molecule is a fusion protein between a second target protein and a tag that binds to the first target protein. In some embodiments, the first target protein is a PDZ domain. In some embodiments, the tag is a Ctag. In some embodiments, the molecule comprises a protease cleavage site between the second target protein and the tag. In some embodiments, the protease cleavage site is one known in the art or described herein. In some embodiments, the method further comprises purifying the molecule by separating the aggregated protein from the first and second composition. The separating may be done by methods known in the art such as pelleting the aggregated proteins (i.e. centrifugation) or other separation techniques based on size and charge, for example. In some embodiments, the method further comprises eluting the second target protein. In some embodiments the elution is done by adding an eluting peptide or peptide that competes for the binding to the first target protein. In some embodiments, the eluting peptide is a peptide of SEQ ID NO:14 or a peptide having at least 90% sequence identity to SEQ ID NO:14. In some embodiments, the method further comprises contacting the molecule with a protease that cleaves between the second target protein and the tag.

In some embodiments, the fusion protein is capable of forming the protein aggregates in aqueous buffer with salt concentrations between about 0 and 500 mM KCl or NaCl, or with salt concentrations less than any one of or between any two of about 50, 100, 150, 200, 250, 300, 350, 400, 450, and 500 mM KCl or NaCl. In some embodiments, the fusion protein is capable of forming the protein aggregates when the fusion protein is present in an aqueous solution at a concentration of less than about 5 µM or at a concentration of less than any one of or between any two of about 5, 10, 15, 20, 25, 30, 35, 40, 45, and 50 µM. In some embodiments, the fusion protein is also capable of forming the protein aggregates when the fusion protein is present in an aqueous solution at a concentration of greater than 50 µM.

In some embodiments, the target protein (or first target protein) in a fusion protein described above is ferritin or a ferritin subunit, a fluorescent protein, an antibody, an antibody fragment, protein A, streptavidin, protein G, protein A/G, protein L, StrepTactin, anti-HA antibody (IgG1 against YPYDVPDYA (SEQ ID NO:15)), anti-cMYC antibody (IgG1 against EQKLISEEDL (SEQ ID NO:16)), anti-Glutathione S-transferase antibody (GSTs), anti-FLAG antibody (e.g., anti-DYKDDDDK (SEQ ID NO:17) or anti-DDDDK (SEQ ID NO:18) antibody), a monobody, or an affinity clamp. In some embodiments, the target protein is an antibody fragment (e.g., Fab or scFv), monobody, or affinity clamp that specifically binds to cMYC, GST, FLAG, or other protein "tags" known to those of skill in the art.

In some embodiments, the target protein is ferritin. Ferritin is a protein expressed in many living organisms that stores iron and releases it in a controlled fashion. In some embodiments, the ferritin causes the protein aggregates to be paramagnetic, which allows them to be pelleted, manipulated, or removed using magnets. The ferritin in the protein aggregates described herein can be from any species. It is within the capability of a person of ordinary skill in the art to select a ferritin protein to include in the protein aggregates and to select a suitable nucleic acid encoding a ferritin protein or subunit. In some embodiments, the fusion protein comprised in the protein aggregate further comprises the ferritin. That is, the fusion protein can include the self-assembly domain, a target protein, and ferritin or a ferritin subunit. The fusion protein can also comprise only the self-assembly domain and ferritin. In some embodiments, the ferritin is comprised in a second fusion protein comprising a self-assembly domain. In some embodiments, the protein aggregate further comprises a fluorescent protein. In some embodiments, the fusion protein further comprises the fluorescent protein. In some embodiments, the fluorescent protein is comprised in a second fusion protein comprising a self-assembly domain. In some embodiments, the fluorescent protein is Clover or mRuby2. In some embodiments, the protein aggregate further comprises self-assembly domain proteins fused to other protein components. The self-assembly domain proteins can be naturally occurring proteins that contain a self-assembly domain or isolated self-assembly domain sequences. It is contemplated that in some embodiments, the protein aggregate does not contain any naturally-occurring proteins. In some embodiments, the majority of the fusion protein molecules that comprise the aggregate form direct noncovalent protein-protein interactions with other fusion protein molecules. In some embodiments, the protein-protein interactions are aromatic-aromatic, cation-aromatic, or hydrophobic interactions.

In some embodiments, a fusion protein as described above is comprised in an aqueous composition comprising an aggregate nucleating agent. In some embodiments, the aggregate nucleating agent is a thermally unstable protein that unfolds or misfolds at temperatures at or below about 40, 42, 45, or 50° C. In some embodiments, the aggregate nucleating agent is firefly luciferase.

Also disclosed is a self-assembly domain covalently conjugated to one or more other polypeptides through a non-peptide bond. The self-assembly domain and the other polypeptide can be separately expressed and then conjugated together through chemical cross-linking means, which are known to persons of skill in the art. The resulting molecule can be used to form protein aggregates according to the methods described herein.

In some embodiments, any of the fusion proteins described above can comprise a second, third, fourth, or fifth target protein or more.

In some embodiments, it is contemplated that a fusion protein consists entirely of a contiguous string of amino acids. In some embodiments, the fusion protein does not have any additional chemical entity joined to the amino acid string. It is also contemplated that the fusion protein can consist of only a self-assembly domain and a target protein as a single, contiguous amino acid string.

In some embodiments, a fusion protein described above can be conjugated to another polypeptide or other molecule through peptide or non-peptide covalent bonds. The self-assembly domain itself can also be conjugated to other polypeptides or other types of molecules through peptide or non-peptide covalent bonds. For example, in some embodiments, the self-assembly domain can be conjugated to biotin. In some embodiments, the self-assembly domain is not part of a fusion protein with a target protein, but is covalently conjugated to another molecule. The other molecule can include other polypeptides, small molecules, nucleic acids, or other types of molecules.

In some embodiments, the invention comprises a method of delivering a substance to a specific body site, comprising, (a) providing a fusion protein comprising a target protein capable of binding the substance fused to a heat-inducible self-assembly domain, (b) adding the substance to the fusion protein, (c) administering the fusion protein and substance to a patient, and (d) locally heating the body site. In specific embodiments, the substance is a nucleic acid, a protein or peptide-based therapeutic.

In some embodiments, the invention comprises a method of assessing modulators of aggregation in vitro by (a) providing a heat-inducible self-assembly domain in an aqueous solution, (b) adding a substance, (c) administering heat to the sample, and (d) measuring the degree of aggregation of the domain.

In some embodiments, the invention comprises a method of assessing modulators of aggregation in vitro by (a) providing a heat-inducible self-assembly domain fused to a protein in an aqueous solution, (b) adding a substance, (c) administering heat to the sample (d) measuring the degree of aggregation of the fusion protein. In specific embodiments, the protein is a fluorescent protein. In other specific embodiments, a mixture of fusion proteins is used where each protein has a heat-inducible self-assembly domain and a fluorescent protein that can interact with other fusion proteins in the mixture to provide FRET mediated fluorescence upon assembly.

In some embodiments, the invention comprises a method of assessing modulators of aggregation in vivo by (a) expressing a heat-inducible self-assembly domain fused to a protein in a cell, (b) administering a substance to the cell, (c) administering heat to the sample, (d) measuring the degree of aggregation of the fusion protein. In specific embodiments, the domain is a fluorescent protein. In other specific embodiments a mixture of fusion proteins is expressed where each protein has a heat-inducible self-assembly domain and a fluorescent protein that can interact with other fusion proteins in the mixture to provide FRET mediated fluorescence upon assembly.

It is contemplated that any embodiment described herein can be combined with any other described embodiment. For example, the features described for protein aggregates or fusion proteins in one embodiment can be applied to the protein aggregate or fusion proteins of any other embodiment. Likewise, any method steps described in a given method can be included in any other described method, and any method can incorporate or use any fusion protein or protein aggregate described herein.

As used herein, a "self-assembly domain" is a polypeptide sequence that imparts to a polypeptide, of which it is a part of, the ability to form protein aggregates under certain conditions. In some embodiments, the self-assembly domain is heat-inducible; that is, a protein that includes a heat-inducible self-assembly domain is soluble in aqueous solution at relatively low temperatures (e.g., below about 35° C.) but assembles into aggregates with other proteins that include a heat-inducible self-assembly domain upon heating to a higher temperature (e.g., at least about 35° C.).

As used herein, "target protein" means a polypeptide that is distinct from a self-assembly domain. The term "target protein" excludes the amino acids that make up the self-assembly domain itself. The term "target protein" also excludes polypeptides that naturally possess a self-assembly domain, such as some GST-like proteins from *Saccharomyces cerevisiae* or *Ogataea parapolymorpha*.

As used herein, a "fusion protein" is a single, contiguous polypeptide molecule that comprises two or more distinct amino acid sequences derived from at least two distinct sources. In some embodiments, a distinct source can be a naturally-occurring gene product sequence, a man-made polypeptide sequence, or fragments of either. In some embodiments, each distinct amino acid sequence included in a fusion protein has at least or at most 3, 4, 5, 6, 7, 8, 9, 10, 11, 12, 13, 14, 15, 16, 17, 18, 19, 20, 25, 30, 35, 40, 45, 50, 60, 70, 80, 90, or 100 amino acids or any derivable range therein. In some embodiments, each distinct amino acid sequence has a distinct function that is associated with its source and includes enough of the amino acid sequence from the source to impart that functionality to the fusion protein.

For example, in some embodiments, a fusion protein includes an amino acid sequence derived from a self-assembly domain and an amino acid sequence derived from a green fluorescent protein. In such a fusion protein, the self-assembly domain amino acid sequence has self-assembly functionality and the green fluorescent protein amino acid sequence has fluorescence functionality. The functionality imparted to the fusion protein by the distinct amino acid sequence may also be, for example, binding to a specific protein, small molecule, or ligand; performing a structural role; undergoing a conformation change under certain conditions; performing an enzymatic function such as catalyzing a chemical reaction; fluorescing under certain conditions; and so forth. In some embodiments described herein, the fusion proteins comprise distinct amino acid sequences from more than two distinct sources. A fusion protein can include at least, at most, or exactly 2, 3, 4, 5, 6, 7, or more distinct proteins or polypeptides (or any derivable range therein). The self-assembly domain in the fusion proteins described herein may be derived from a naturally-occurring protein sequence or may be artificial. As used herein, "fusion protein" does not include a polypeptide that is wholly derived from a single, naturally occurring gene product. As used herein, "fusion proteins" are not naturally-occurring.

The terms "a" and "an" are defined as one or more unless this disclosure explicitly requires otherwise.

The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

Throughout this application, the term "about" is used to indicate that a value includes the standard deviation of error for the device or method being employed to determine the value.

Furthermore, a structure that is capable performing a function or that is configured in a certain way is capable or configured in at least that way, but may also be capable or configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any method or system of the present invention can consist of or consist essentially of rather than comprise/include/contain/have any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

FIG. 4A shows the purification of the fluorescent protein, Clover. FIG. 4B compares purification of six different proteins (Clover, mRuby2, hGH, Suil, β-Gal, Pab1) using the current method with purification using the traditional His-tag method. The top bar graph of FIG. 4B shows the purity achieved for each protein using the FENEX purification method described herein (left bar in each pair) and the His-tag purification method (right bar in each pair). The bottom bar graph of FIG. 4B shows the yield (in mg of protein per liter of culture) achieved for each protein using the FENEX purification method (left bar in each pair) and the His-tag purification method (right bar in each pair). The purification method described herein is twice as fast as His-tag purification, allows for simultaneous purification of many proteins (high-throughput screens) and is inexpensive.

DETAILED DESCRIPTION OF THE INVENTION

Figure 1:
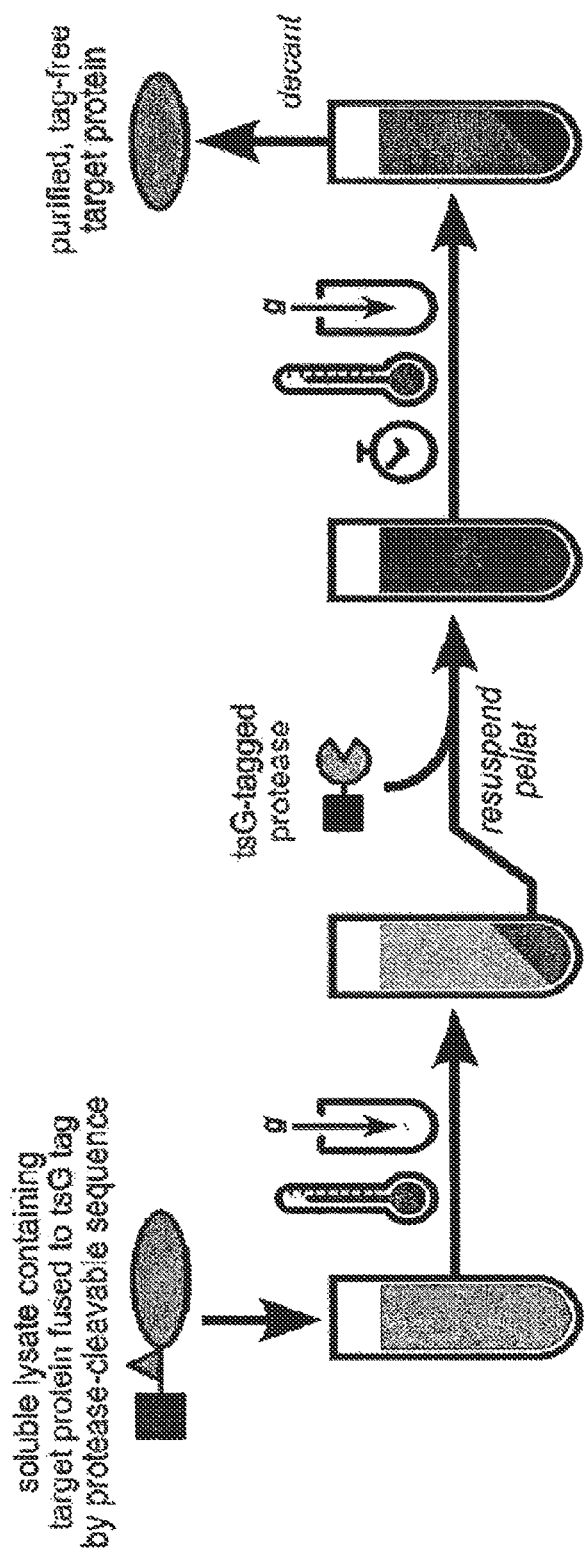
FIG. 1. Overview of purification method. Recombinant target protein (oval) linked to a temperature-sensitive glutathione-S-transferase (GST)-like polypeptide tag (tsG tag) (square) by a protease-cleavable linker (triangle) is expressed in host cells, which are lysed to release the protein and many contaminants. Soluble lysate is incubated for 10 minutes at 50° C. and centrifuged at 20,000 g. The pellet is resuspended and incubated with a tsG-tagged protease, which cleaves the linker and liberates the target protein. After another 10 minutes 50° C. incubation and centrifugation, the purified, tag-free protein is recovered from the supernatant.

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth.

A. PROTEINS AND PROTEIN EXPRESSION

1. Protein Sequences

In some embodiments, fusion proteins and/or protein aggregates described herein include self-assembly domain sequences from a GST-like domain, as described herein or from the proteins set forth in the table below:

| Systematic Name | Common Name |
| --- | --- |
| YGL105W | Arc1 |
| YGR264C | Mes1 |
| YGL245W | Gus1 |
| YPL048W | Tef3 |
| YKL081W | Tef4 |
| YAL003W | Efb1, |
| YLR249W | Yef3 |
| YBL039C | Ura7 |

The table above gives the systematic name from *S. cerevisiae*, but it is contemplated that the homolog from other species may be used.

In some embodiments, the fusion proteins and/or protein aggregates described herein include fluorescent proteins. One fluorescent protein that can be used is Clover, a sequence for which is set forth in GenBank accession number AFR60231, which is hereby incorporated by reference. Further fluorescent proteins are described in Lee et al. (*PLoS One* 8:367902 (2013)), which is hereby incorporated by reference.

2. Polypeptide Production

In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979). Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, can be performed by routine techniques known to those of skill in the art.

In some embodiments, fusion proteins can be expressed from a nucleotide construct that encodes the entire fusion protein. Alternatively, fusion proteins can be formed by covalently joining different proteins after they have already been produced.

3. Protein Purification or Isolation

In certain embodiments a protein or peptide or a composition comprising such a protein or peptide may be isolated or purified. Protein purification techniques are well known to those of skill in the art. These techniques involve, at one level, the homogenization and crude fractionation of the cells, tissue or organ in to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur.

Generally, "purified" will refer to a protein or peptide composition that has been subjected to fractionation to remove various other components, and which the composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

A peptide, polypeptide or protein that is "purified to homogeneity," as applied to the present invention, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A particular method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

To purify a desired protein, polypeptide, or peptide a natural or recombinant composition comprising at least some specific proteins, polypeptides, or peptides may be subjected to fractionation to remove various other components from the composition. Various techniques suitable for use in protein purification are well known to those of skill in the art. These include, for example, precipitation with ammonium sulfate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Another example is the purification of a specific fusion protein using a specific binding partner. Such purification methods are routine in the art. Certain aspects of the present invention provide DNA sequences for the specific proteins, and any fusion protein purification method may be practiced. However, given many DNA and proteins are known, or may be identified and amplified using the methods described herein, any purification method can now be employed.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

B. SEQUENCE LISTING

| Systematic Name | Common Name |
| --- | --- |
| YGL105W | Arc1 |
| YGR264C | Mes1 |
| YGL245W | Gus1 |
| YPL048W | Tef3 |
| YKL081W | Tef4 |
| YAL003W | Efb1, |
| YLR249W | Yef3 |
| YBL039C | Ura7 |

*S. cerevisiae* YGL105W/Arc1:

(SEQ ID NO: 1)
MSDLVTKFESLIISKYPVSFTKEQSAQAAQWESVLKSGQIQPHLDQLNL

VLRDNTFIVSTLYPTSTDVHVFEVALPLIKDLVASSKDVKSTYTTYRHI

LRWIDYMQNLLEVSSTDKLEINHDLDLPHEVIEKKKKAPAGGAADAAAK

ADEDVSKKAKKQDHPRGKPDEETLKKLREEAKAKKAAKKAANAKQQQEQ

QNKAPEKPKPSAIDFRVGFIQKAIKHPDADSLYVSTIDVGDEEGPRTVC

SGLVKHFPLDAMQERYVVVVCNLKPVNMRGIKSTAMVLCGSNDDKVEFV

EPPKDSKAGDKVFFEGFGDEAPMKQLNPKKKIWEHLQPHFTTNDGLEVI

FKDEEEKDHPVRKLTNA KGESFKVASI ANAQVR*

*S. cerevisiae* YGR264C/Mes1:

(SEQ ID NO: 2)
MSFLISFDKSKKHPAHLQLANNLKIALALEYASKNLKPEVDNDNAAMELR

NTKEPFLLFDANAILRYVMDDFEGQTSDKYQFALASLQNLLYHKELPQQH

VEVLTNKAIENYLVELKEPLTTTDLILFANVYALNSSLVHSKFPELPSKV

HNAVALAKKHVPRDSSSFKNIGAVKIQADLTVKPKDSEILPKPNERNILI

TSALPYVNNVPHLGNIIGSVLSADIFARYCKGRNYNALFICGTDEYGTAT

ETKALEEGVTPRQLCDKYHKIHSDVYKWFQIGFDYFGRTTTDKQTEIAQH

IFTKLNSNGYLEEQSMKQLYCPVHNSYLADRYVEGECPKCHYDDARGDQC

-continued

```
DKCGALLDPFELINPRCKLDDASPEPKYSDHIFLSLDKLESQISEWVEKA

SEEGNWSKNSKTITQSWLKDGLKPRCITRDLVWGTPVPLEKYKDKVLYVW

FDATIGYVSITSNYTKEWKQWWNNPEHVSLYQFMGKDNVPFHTVVFPGSQ

LGTEENWTMLHHLNTTEYLQYENGKFSKSRGVGVFGNNAQDSGISPSVWR

YYLASVRPESSDSHFSWDDFVARNNSELLANLGNFVNRLIKFVNAKYNGV

VPKFDPKKVSNYDGLVKDINEILSNYVKEMELGHERRGLEIAMSLSARGN

QFLQENKLDNTLFSQSPEKSDAVVAVGLNIIYAVSSIITPYMPEIGEKIN

KMLNAPALKIDDRFHLAILEGHNINKAEYLFQRIDEKKIDEWRAKYGGQQ

V*
```

*S. cerevisiae* YGL245W/Gus1:

(SEQ ID NO: 3)
```
MPSTLTINGKAPIVAYAELIAARIVNALAPNSIAIKLVDDKKAPAAKLDD

ATEDVFNKITSKFAATFDNGDKEQVAKWVNLAQKELVIKNFAKLSQSLET

LDSQLNLRTFTLGGLKYSAADVACWGALRSNGMCGSIIKNKVDVNVSRWY

TLLEMDPIFGEAHDFLSKSLLELKKSANVGKKKETHKANFEIDLPDAKMG

EVVTRFPPEPSGYLHIGHAKAALLNQYFAQAYKGKLIIRFDDTNPSKEKE

EFQDSILEDLDLLGIKGDRITYSSDYFQEMYDYCVQMIKDGKAYCDDTPT

EKMREERMDGVASARRDRSVEENLRIFTEEMKNGTEEGLKNCVRAKIDYK

ALNKTLRDPVIYRCNLTPHHRTGSTWKIYPTYDFCVPIVDAIEGVTHALR

TIEYRDRNAQYDWMLQALRLRKVHIWDFARINFVRTLLSKRKLQWMVDKD

LVGNWDDPRFPTVRGVRRRGMTVEGLRNFVLSQGPSRNVINLEWNLIWAF

NKKVIDPIAPRHTAIVNPVKIHLEGSEAPQEPKIEMKPKHKKNPAVGEKK

VIYYKDIVVDKDDADVINVDEEVTLMDWGNVIITKKNDDGSMVAKLNLEG

DFKKTKHKLTWLADTKDVVPVDLVFDHLITKDRLEEDESFEDFLTPQTE

FHTDAIADLNVKDMKIGDIIQFERKGYYRLDALPKDGKPYVFFTIPDGKS

VNKYGAKK*
```

*S. cerevisiae* YPL048W/Tef3:

(SEQ ID NO: 4)
```
MSQGTLYANFRIRTWVPRGLVKALKLDVKVVTPDAAAEQFARDFPLKKVP

AFVGPKGYKLTEAMAINYYLVKLSQDDKMKTQLLGADDDLNAQAQIIRWQ

SLANSDLCIQIANTIVPLKGGAPYNKKSVDSAMDAVDKIVDIFENRLKNY

TYLATENISLADLVAASIFTRYFESLFGTEWRAQHPAIVRWFNTVRASPF

LKDEYKDFKFADKPLSPPQKKKEKKAPAAAPAASKKKEEAKPAATETETS

SKKPKHPLELLGKSTFVLDDWKRKYSNEDTRPVALPWFWEHYNPEEYSLW

KVTYKYNDELTLTFMSNNLVGGFFNRLSASTKYMFGCLVVYGENNNNGIV

GAVMVRGQDYVPAFDVAPDWESYDYAKLDPTNDDDKEFINNMWAWDKPVS

VNGEPKEIVDGKVLK*
```

*S. cerevisiae* YKL081W/Tef4:

(SEQ ID NO: 5)
```
MSQGTLYINRSPRNYASEALISYFKLDVKIVDLEQSSEFASLFPLKQAPA

FLGPKGLKLTEALAIQFYLANQVADEKERARLLGSDVIEKSQILRWASLA

NSDVMSNIARPFLSFKGLIPYNKKDVDACFVKIDNLAAVFDARLRDYTFV

ATENISLGDLHAAGSWAFGLATILGPEWRAKHPHLMRWFNTVAASPIVKT

PFAEVKLAEKALTYTPPKKQKAEKPKAEKSKAEKKKDEAKPADDAAPAKK

PKHPLEALGKSTFVLDDWKRKYSNDDTRPVALPWFWEHYNPEEYSIWKVG

YKYNDELTLTFMSNNLVGGFFNRLSASTKYMFGCLVVYGENNNNGIVGAV

MVRGQDFAPAFDVAPDWESYEYTKLDPTKEEDKEFVNNMWAWDKPVVVNG

EDKEIVDGKVLK*
```

*S. cerevisiae* YAL003W/Efb1:

(SEQ ID NO: 6)
```
MASTDFSKIETLKQLNASLADKSYIEGTAVSQADVTVFKAFQSAYPEFSR

WFNHIASKADEFDSFPAASAAAAEEEEDDDVDLFGSDDEEADAEAEKLKA

ERIAAYNAKKAAKPAKPAAKSIVTLDVKPWDDETNLEEMVANVKAIEMEG

LTWGAHQFIPIGFGIKKLQINCVVEDDKVSLDDLQQSIEEDEDHVQSTDI

AAMQKL*
```

*S. cerevisiae* YLR249W/Yef3:

(SEQ ID NO: 7)
```
MSDSQQSIKVLEELFQKLSVATADNRHEIASEVASFLNGNIIEHDVPEHF

FGELAKGIKDKKTAANAMQAVAHIANQSNLSPSVEPYIVQLVPAICTNAG

NKDKEIQSVASETLISIVNAVNPVAIKALLPHLTNAIVETNKWQEKIAIL

AAISAMVDAAKDQVALRMPELIPVLSETMWDTKKEVKAAATAAMTKATET

VDNKDIERFIPSLIQCIADPTEVPETVHLLGATTFVAEVTPATLSIMVPL

LSRGLNERETGIKRKSAVIIDNMCKLVEDPQVIAPFLGKLLPGLKSNFAT

IADPEAREVTLRALKTLRRVGNVGEDDAIPEVSHAGDVSTTLQVVNELLK

DETVAPRFKIVVEYIAAIGADLIDERIIDQQAWFTHITPYMTIFLHEKKA

KDILDEFRKRAVDNIPVGPNFDDEEDEGEDLCNCEFSLAYGAKILLNKTQ

LRLKRARRYGICGPNGCGKSTLMRAIANGQVDGFPTQEECRTVYVEHDID

GTHSDTSVLDFVFESGVGTKEAIKDKLIEFGFTDEMIAMPISALSGGWKM

KLALARAVLRNADILLLDEPTNHLDTVNVAWLVNYLNTCGITSITISHDS

VFLDNVCEYIINYEGLKLRKYKGNFTEFVKKCPAAKAYEELSNTDLEFKF

PEPGYLEGVKTKQKAIVKVTNMEFQYPGTSKPQITDINFQCSLSSRIAVI

GPNGAGKSTLINVLTGELLPTSGEVYTHENCRIAYIKQHAFAHIESHLDK

TPSEYIQWRFQTGEDRETMDRANRQINENDAEAMNKIFKIEGTPRRIAGI

HSRRKFKNTYEYECSFLLGENIGMKSERWVPMMSVDNAWIPRGELVESHS

KMVAEVDMKEALASGQFRPLTRKEIEEHCSMLGLDPEIVSHSRIRGLSGG

QKVKLVLAAGTWQRPHLIVLDEPTNYLDRDSLGALSKALKEFEGGVIIIT
```

HSAEFTKNLTEEVWAVKDGRMTPSGHNWVSGQGAGPRIEKKEDEEDKFDA

MGNKIAGGKKKKKLSSAELRKKKKERMKKKKELGDAYVSSDEEF*

S. cerevisiae YBL039C/Ura7:

(SEQ ID NO: 8)
MKYVVVSGGVISGIGKGVLASSTGMLMKTLGLKVTSIKIDPYMNIDAGTM

SPLEHGECFVLDDGGETDLDLGNYERYLGVTLTKDHNITTGKIYSHVIAK

ERKGDYLGKTVQIVPHLTNAIQDWIERVAKIPVDDTGMEPDVCIIELGGT

VGDIESAPFVEALRQFQFKVGKENFALIHVSLVPVIHGEQKTKPTQAAIK

GLRSLGLVPDMIACRCSETLDKPTIDKIAMFCHVGPEQVVNVHDVNSTYH

VPLLLLEQKMIDYLHARLKLDEISLTEEEKQRGLELLSKWKATTGNFDES

METVKIALVGKYTNLKDSYLSVIKALEHSSMKCRRKLDIKWVEATDLEPE

AQESNKTKFHEAWNMVSTADGILIPGGFGVRGTEGMVLAARWARENHIPF

LGVCLGLQIATIEFTRSVLGRKDSHSAEFYPDIDEKNHVVVFMPEIDKET

MGGSMRLGLRPTFFQNETEWSQIKKLYGDVSEVHERHRHRYEINPKMVDE

LENNGLIFVGKDDTGKRCEILELKNHPYYIATQYHPEYTSKVLDPSKPFL

GLVAASAGILQDVIEGKYDLEAGENKFNF*

S. cerevisiae YGL245W/Gus1; 191Aa N-Terminal Polypeptide with GST-Like Domain:

(SEQ ID NO: 9)
MPSTLTINGKAPIVAYAELIAARIVNALAPNSIAIKLVDDKKAPAAKLDD

ATEDVFNKITSKFAAIFDNGDKEQVAKWVNLAQKELVIKNFAKLSQSLET

LDSQLNLRTFILGGLKYSAADVACWGALRSNGMCGSIIKNKVDVNVSRWY

TLLEMDPIFGEAHDFLSKSLLELKKSANVGKKKETHKANFE

S. cerevisiae YGR264C/Mes1; 207Aa N-Terminal Polypeptide with GST-Like Domain:

(SEQ ID NO: 10)
MSFLISFDKSKKHPAHLQLANNLKIALALEYASKNLKPEVDNDNAAMELR

NTKEPFLLFDANAILRYVMDDFEGQTSDKYQFALASLQNLLYHKELPQQH

VEVLTNKAIENYLVELKEPLTTTDLILFANVYALNSSLVHSKFPELPSKV

HNAVALAKKHVPRDSSSFKNIGAVKIQADLTVKPKDSEILPKPNERNILI

TSALPYV

S. cerevisiae YKL081W/Tef4; 156Aa N-Terminal Polypeptide with GST-Like Domain:

(SEQ ID NO: 11)
MSQGTLYINRSPRNYASEALISYFKLDVKIVDLEQSSEFASLFPLKQAPA

FLGPKGLKLTEALAIQFYLANQVADEKERARLLGSDVIEKSQILRWASLA

NSDVMSNIARPFLSFKGLIPYNKKDVDACFVKIDNLAAVFDARLRDYTFV

ATENIS

S. cerevisiae YPL048W/Tef3; 159Aa N-Terminal Polypeptide with GST-Like Domain:

(SEQ ID NO: 12)
MSQGTLYANFRIRTWVPRGLVKALKLDVKVVTPDAAAEQFARDFPLKKVP

AFVGPKGYKLTEAMAINYYLVKLSQDDKMKTQLLGADDDLNAQAQIIRWQ

SLANSDLCIQIANTIVPLKGGAPYNKKSVDSAMDAVDKIVDIFENRLKNY

TYLATENIS (SEQ ID NO: 13)
RGSIDTWV.

C-Tag:

(SEQ ID NO: 14)
EEWETWV.

Elution Peptide:
Exemplary tags:

(SEQ ID NO: 15)
YPYDVPDYA;

(SEQ ID NO: 16)
EQKLISEEDL;

(SEQ ID NO: 17)
DYKDDDDK
and (SEQ ID NO: 18)
DDDDK.

TEV Cleavage Site:

(SEQ ID NO: 19)
ENLYFQS

C. EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Following a sudden increase in temperature, cells attenuate protein synthesis and mount the heat-shock transcriptional program, and eukaryotic cells additionally sequester proteins and RNA in stress granules. How cells sense temperature remains unclear. Here, using a novel mass spectrometric method to identify protein aggregation at the proteome scale in budding yeast, Applicants show that within two minutes of a rise in temperature, a limited set of soluble proteins assemble in vivo into large particles which are molecularly distinct from stress granules. Remarkably, Applicants find that assembly is protein-autonomous: recombinant, purified proteins self-assemble in vitro with comparable kinetics in response to an equivalent thermal shift. For glutamyl-tRNA synthetase, autonomous thermal self-assembly occurs between stably folded proteins and reflects temperature-dependent conformational changes in specific protein-protein interaction domains. Applicants propose that a distributed system of sensor domains transduce temperature into autonomous protein assembly to effect rapid adjustment of diffusible protein levels without transcription, translation, or protein modifications.

Example 1

Self-Assembly Domains Induced by Heat to Form Protein Aggregates

Figure 7:
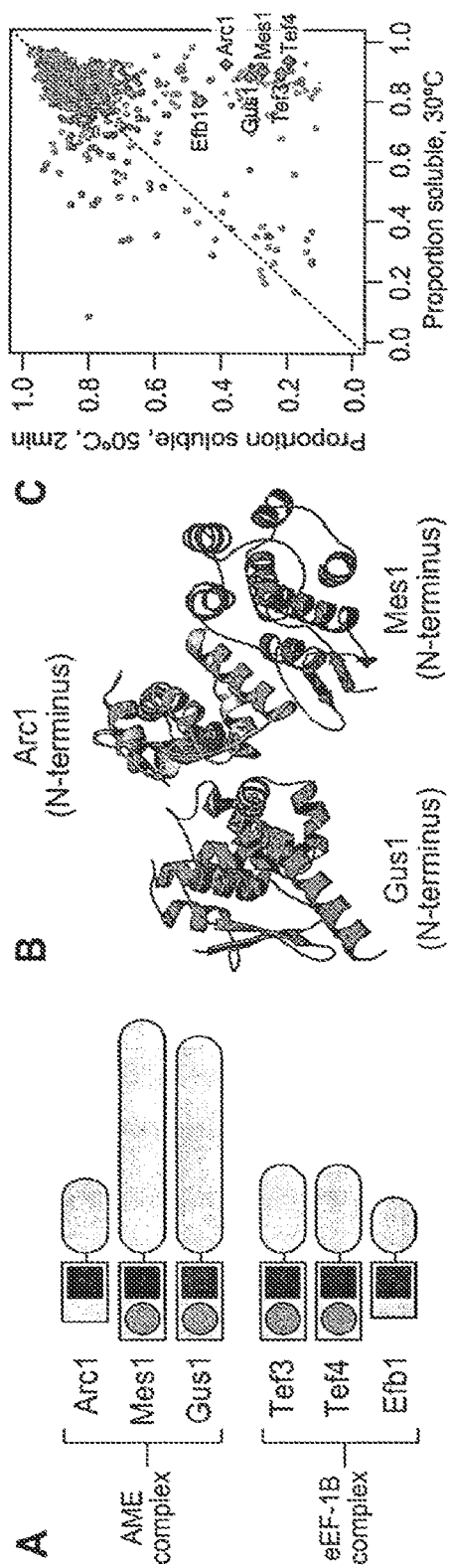
FIG. 7. GST-like domains likely mediate thermal assembly in the AME complex and in the eEF-1B complex. A, Domain architecture. Rectangles show GST-like domains, circles show GST-N (thioredoxin-like) subdomains, and squares show GST-C subdomains. B, Ternary complex of AME GST-like interaction domains. C, Rapid response of proteins in A to thermal shift monitored by mass-spectrometric analysis.

Thermally-induced protein misfolding and aggregation have long been thought to trigger the heat-shock response, but the sensitivity of individual proteins to thermal aggregation has remained unclear. To examine changes in protein aggregation in response to heat stress, Applicants used a proteome-scale mass spectrometric (MS) assay to monitor the ratio of proteins found in the supernatant (aqueous-soluble) and pellet (aqueous-insoluble, detergent-soluble) fractions. To maximize effect sizes, Applicants targeted brief treatments after which only a fraction of cells survive, shifting exponentially growing cells from 30° C. to 50° C. for two, four, and eight minutes. Applicants immediately harvested supernatant and 100,000 g pellet fractions from each, combined the supernatant fraction with the pellet fraction from cells grown on stable-isotope-labeled arginine and lysine, then analyzed the mixed samples by liquid chromatography coupled to tandem mass spectrometry (LC-MS/MS). The data reveal that after two minutes, while the vast majority of proteins showed no significant aggregation, a small set of highly soluble proteins form pelletable aggregates (FIG. 7C), with 31 of 597 protein (5%) increasing at least four-fold in the insoluble fraction. Little change was observed at later times, with Pearson correlations ≥0.85 between supernatant/pellet ratios at 2, 4, and 8 minutes.

These observations suggested a functional connection between the aggregating proteins, consistent with a thermally triggered assembly process. Heat-induced stress granules were originally identified by a similar centrifugation procedure. Indeed, most components of stress granules induced by robust heat shock, previously studied by fluorescent imaging, are found in these rapidly assembling particles, with the exception of one protein, Dhh1, primarily associated with mRNA processing bodies (P bodies), and one small-subunit ribosomal protein. Stress granules are thought to coalesce around stalled 48S preinitiation complexes, in which the 40S small ribosomal subunit is a core component. Small-subunit proteins are universal markers for stress granules and the yeast ribosomal protein S30, but not large-subunit L25, accumulates in heat-induced granules. However, all of the 131 detected ribosomal gene products, including 56 from the small subunit, remained strongly enriched in the supernatant and were entirely separable from the aggregating proteins at 2 min. Additional initiation-complex components eIF-1A, eIF-2 (a, f3, and y subunits), and eIF-1 also remained soluble. These and further results reported below indicate that these rapidly forming particles do not co-assemble with preinitiation complexes or small ribosomal subunits, distinguishing them from stress granules. The processing-body (P-body) markers Dcp2p also remained in the supernatant, distinguishing these particles from P-bodies. Applicants therefore designated them thermosensitive rapidly assembling particles (TRAPs).

The rapid formation of TRAPs, and their independence from preinitiation complexes led Applicants to wonder whether the constituent proteins themselves possessed the intrinsic ability to transduce a thermal shift into self-assembly. To test this possibility, Applicants purified several TRAP-forming proteins in recombinant form from bacteria (Yef3, Gus1, and CTP synthase/Ura7), along with two control proteins (Sui1/eIF-1 and Hyp2/eIF-5A). Applicants suspended them in aqueous buffer at concentrations approximating their physiological levels, and monitored formation of large particles by visible-light absorbance at 550 nm. When Applicants subjected each protein to the same 30° C. to 50° C. thermal shift in vitro, all TRAP-forming proteins rapidly self-assembled into large particles, and the control proteins did not. Particles grew exponentially until exhaustion of unassembled material (FIG. 6B).

Figure 6:
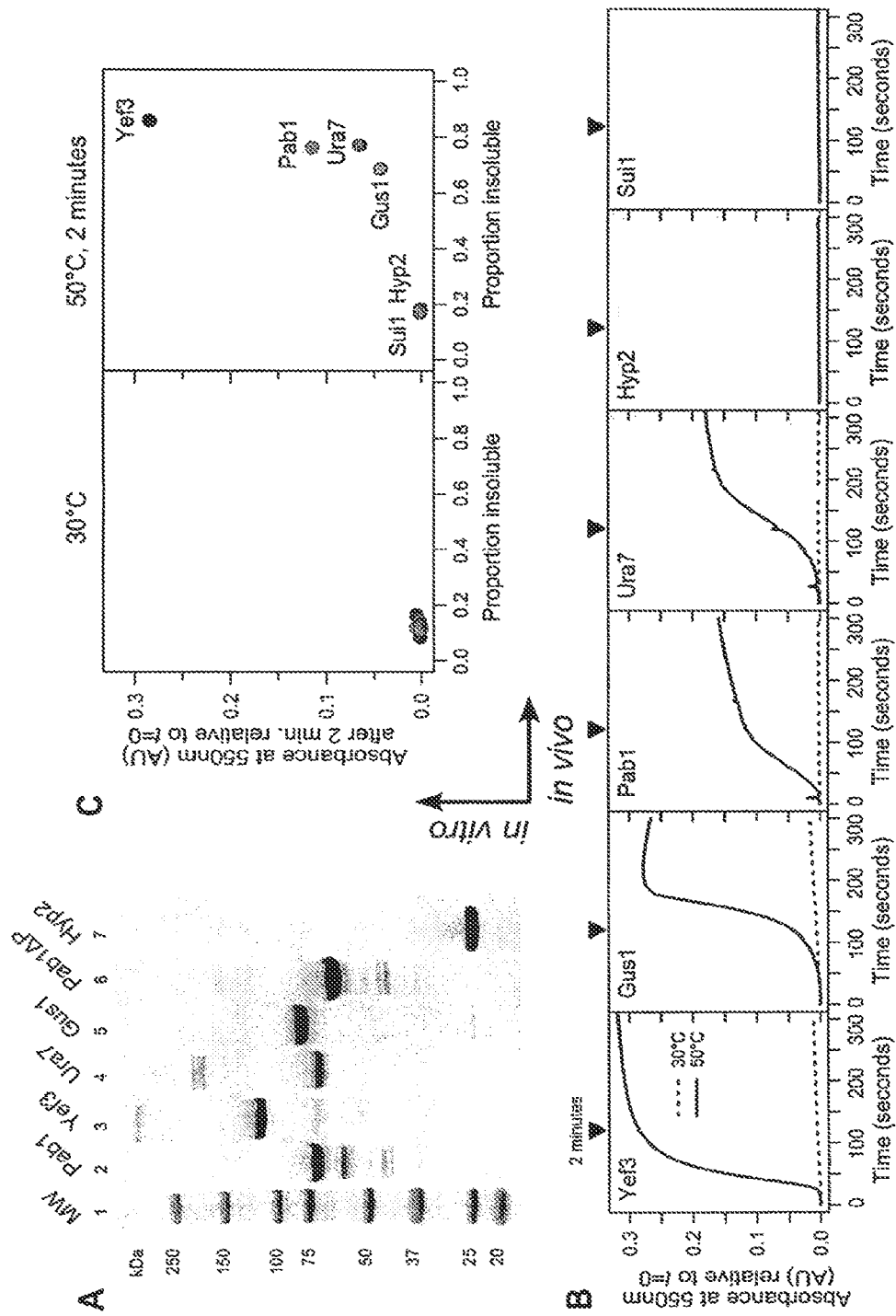
FIG. 6. Recombinant yeast proteins rapidly and autonomously self-assemble into large particles in vitro, recapitulating in vivo TRAP formation. A, Sizing gel of purified proteins. B, Thermally-triggered self-assembly of purified proteins monitored by absorbance; temperature change at t=0. C, Comparison of in vivo and in vitro results after two minutes at the indicated temperature.
Figure 13:
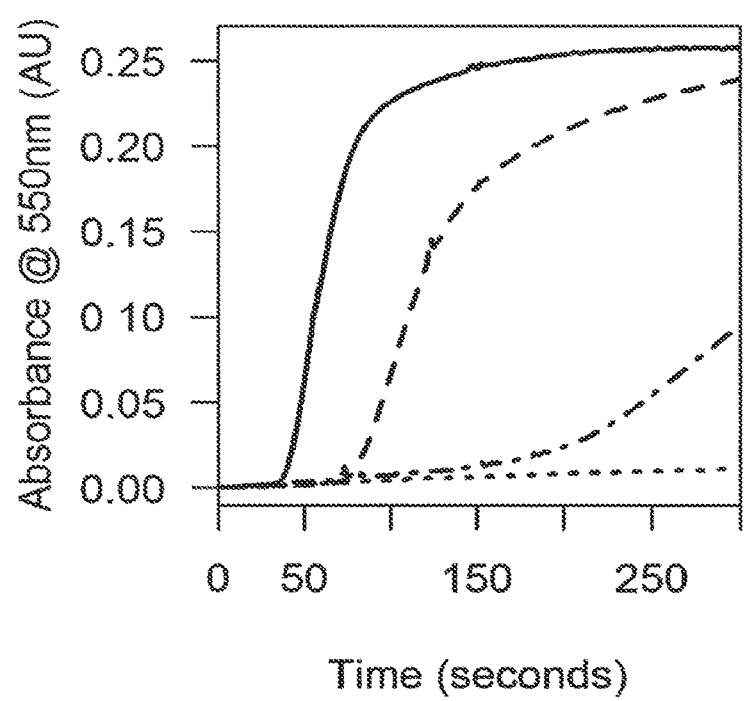
FIG. 13 shows that Yef3 rapidly forms large particles in response to a temperature shift from room temperature to 50° C. (solid line), 46° C. (dashed), and 42° C. (dot-dash), but remains unassembled at 30° C. (dotted).
Figure 14:
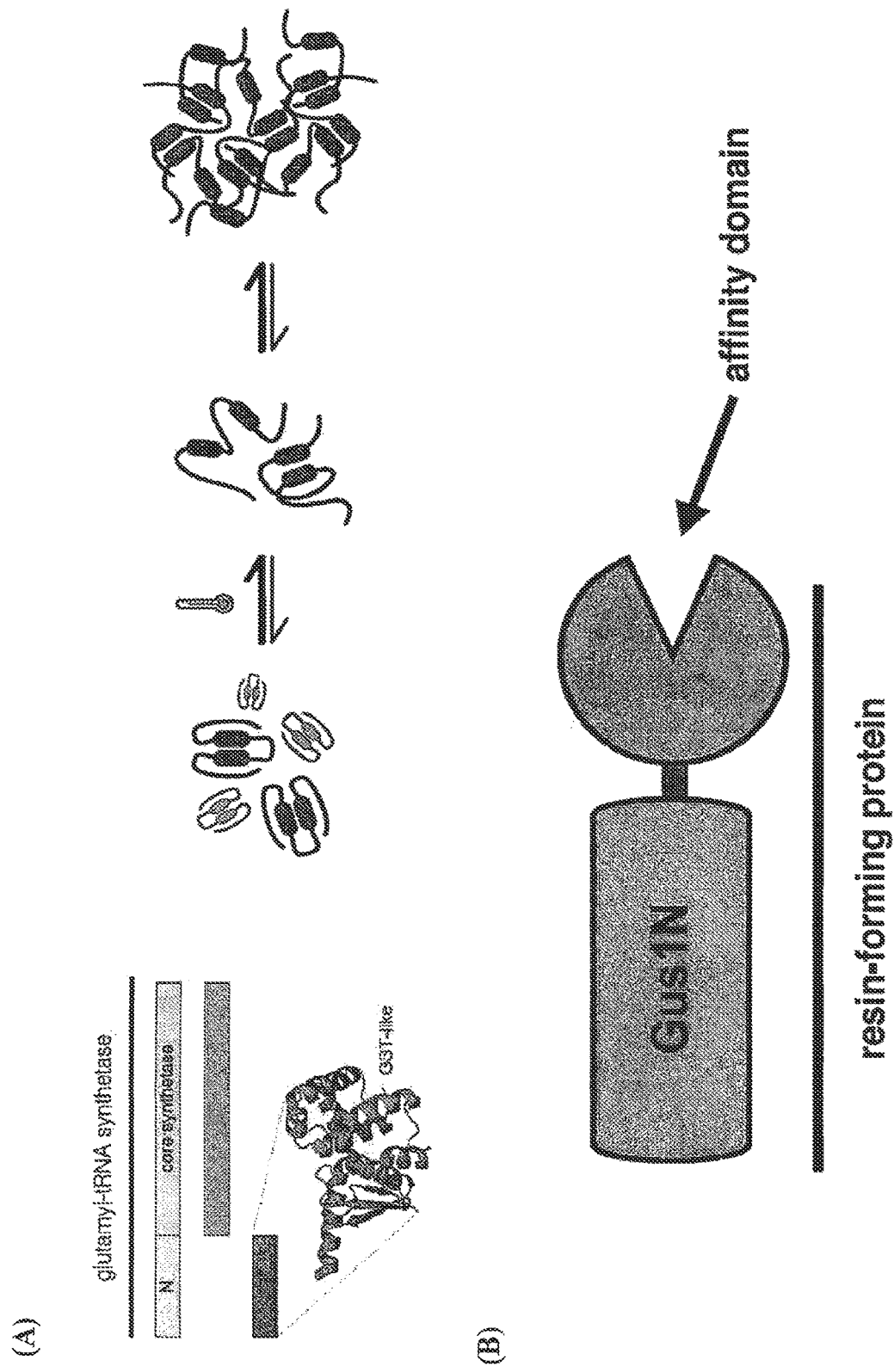
FIG. 14A-B shows the Gus1N self-assembling domain. Shown in A is a scheme which depicts the self-assembly of the Gus1N domains. Shown in B is the Gus1N-affinity domain fusion protein.

Self-assembly in vitro approached saturation in two minutes, consistent with in vivo behavior (FIG. 6C). Applicants then asked whether lower temperatures triggered assembly. Yef3 forms granules at 42° C. in vivo which seed subsequent formation of genuine stress granules. Correspondingly, Yef3 self-assembled rapidly at 46° C. and 42° C. in vitro with temperature-dependent kinetics (FIG. 13).

Figure 8:
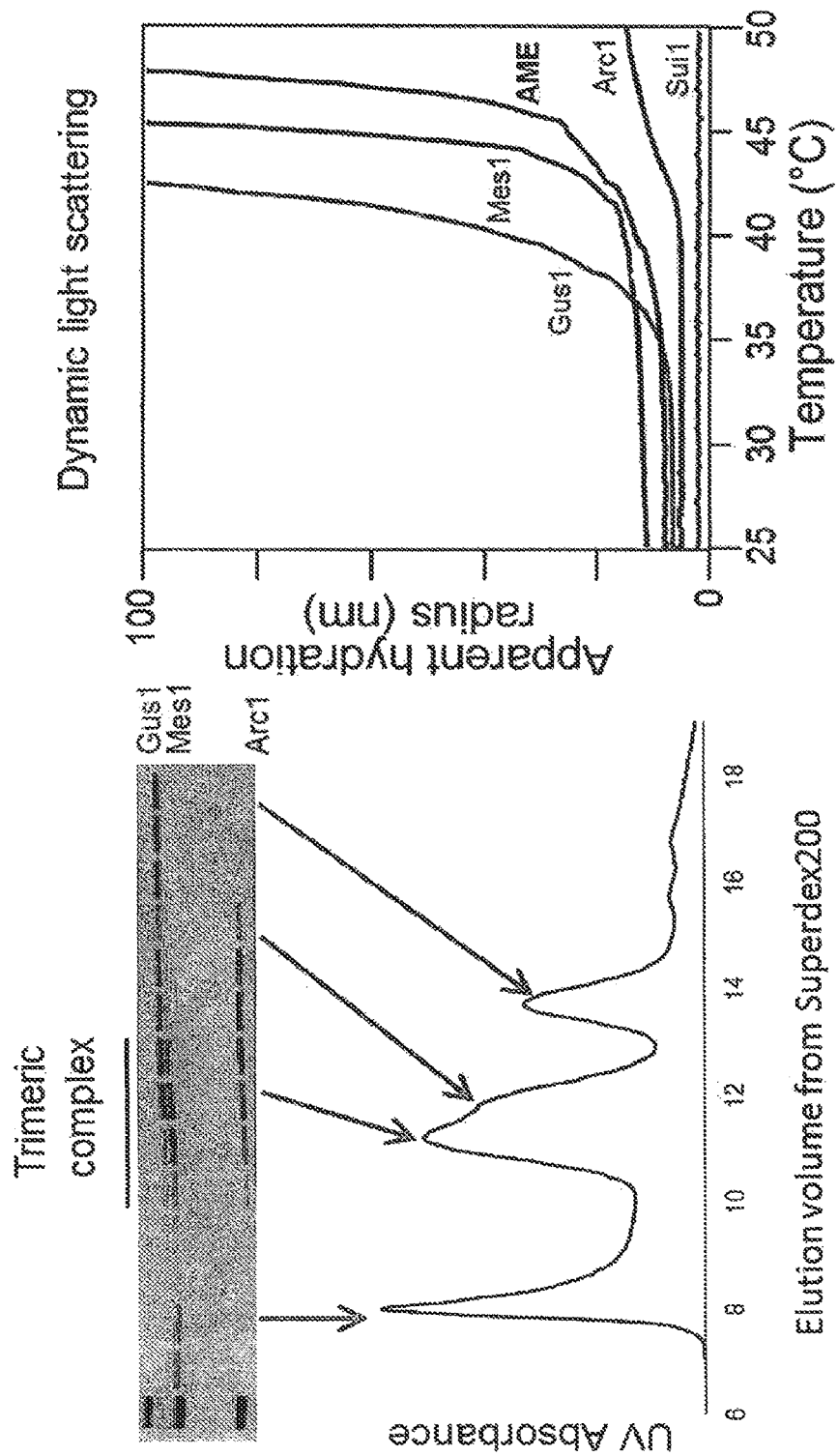
FIG. 8 shows that purified AME complex (complex of three proteins: aminoacylation cofactor (Arc1), methionyl-tRNA synthetase (Mes1), and glutamyl-tRNA synthetase (Gus1)) forms large aggregates upon heat shock. Shown on the left panel is the elution profile from Superdex200 gel filtration column. Above the elution profile is a western blot demonstrating the trimeric complex eluted in fraction 12. This demonstrates reconstitution of a stoichiometric three-protein complex. Shown on the right panel is a dynamic light scattering plot which demonstrates the size distribution profile of the individual proteins in solution and of the AME complex at the indicated temperatures. Gus1, and Mes1 rapidly form large assemblies when heated (dynamic light scattering data), whereas Arc1 shows only modest assembly. Suil, another yeast protein, shows no assembly, as a negative control.
Figure 9:
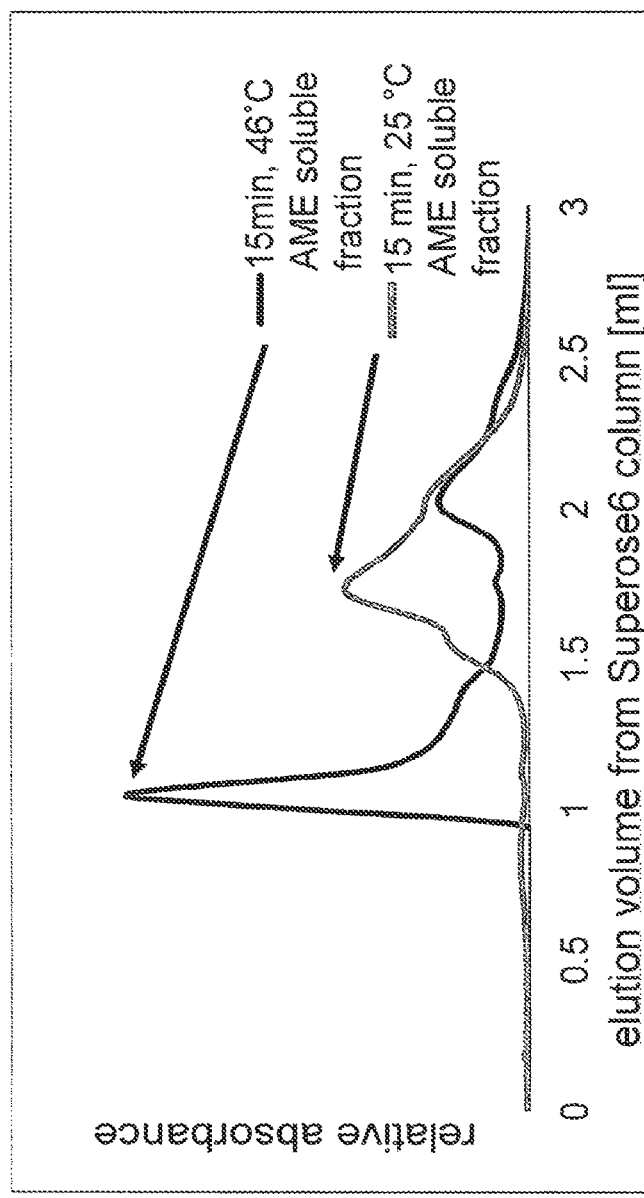
FIG. 9 shows that virtually all of the AME complex is assembled after incubation for 15 minutes at 46° C. Shown is the elution profile from Superose 6 size exclusion chromatography of soluble (non-pelletable) material. At 15 minutes, 46° C., the majority of the protein elutes in 1 mL volume, indicating assembly of large AME complexes. The tallest peak (the left-most peak) is soluble assembly. The second tallest peak shows AME incubated at room temperature (25° C.) for comparison.
Figure 10:
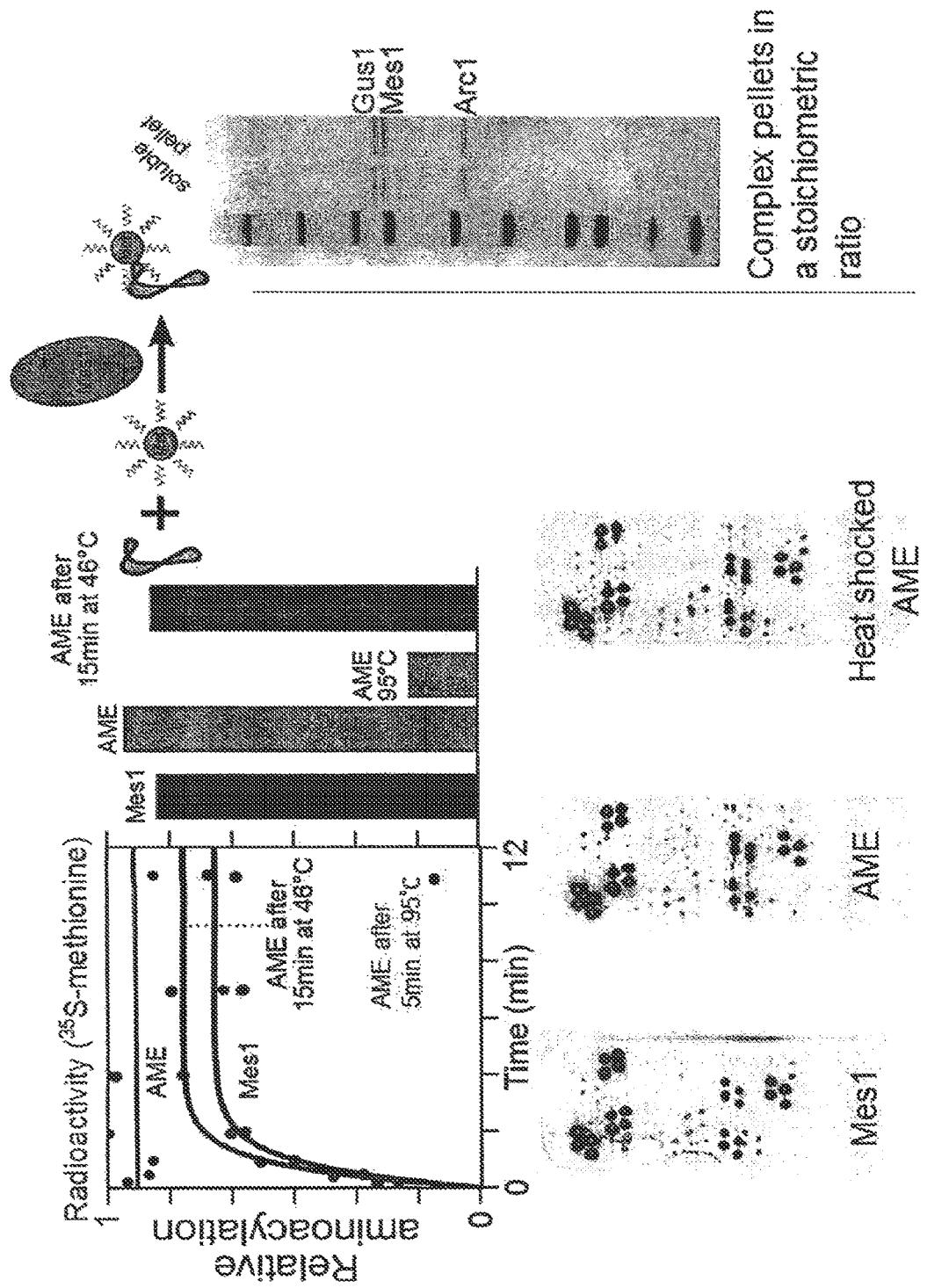
FIG. 10 shows that AME remains functional and possesses normal fidelity after heat shock at 46° C. for 15 min. Aminoacylation of tRNA$^{Met}$ with $^{35}$S methionine is used as a functional readout of AME activity. Top left, kinetic assay comparing equimolar amounts of unheated AME (top, straight line), heated AME (middle line), and unheated Mes1 alone (lower line) reveals that heated AME has slower kinetics relative to unheated AME, yet retains higher activity than unheated Mes1 alone. Bars show results of endpoint activity assay. Right, heated AME forms large complexes which pellet after centrifugation, and silver staining reveals that the three AME components retain 1:1:1 stoichiometry in the pellet, suggesting the complex remains intact. Bottom, tRNA microarray-based misacylation assay (cf. Netzger et al. (2009), "Innate immune and chemically triggered oxidative stress modifies translational fidelity," Nature 462:522-526). The differences between Mes1, AME, and heat-shocked AME methionine acylation patterns are minimal, indicating minimal perturbation of fidelity and again demonstrating activity of heat-shocked AME.

FIG. 8 shows that purified AME complex (complex of three proteins: aminoacylation cofactor (Arc1), methionyl-tRNA synthetase (Mes1), and glutamyl-tRNA synthetase (Gus1)) forms large aggregates upon heat shock. FIG. 9 shows that virtually all of the AME complex is assembled after incubation for 15 minutes at 46° C. FIG. 10 shows AME complexes under electron microscopy. The AME assemblies increase in abundance after 15 min, 46° C., but are absent at 15 minutes, 30° C. FIG. 10 shows that AME remains functional and possesses normal fidelity after heat shock at 46° C. for 15 min.

Applicant's data and previous work indicate that thermal self-assembly in vitro recapitulates assembly in vivo with similar temperature-dependent kinetics.

Figure 12:
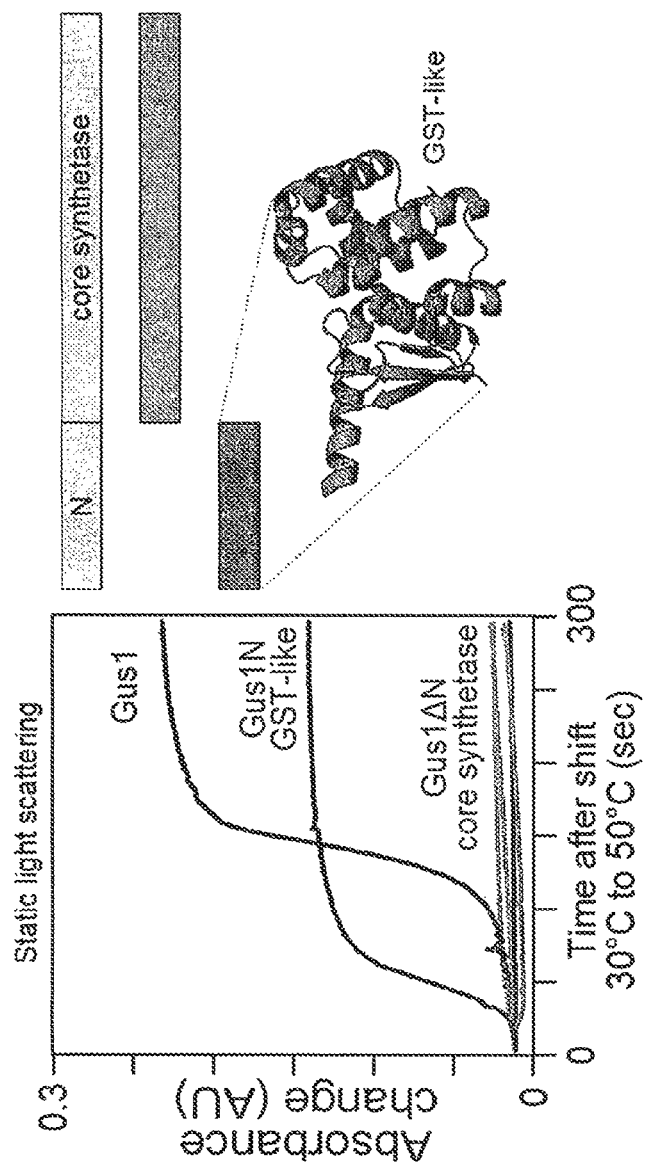
FIG. 12 shows that assembly of Gus1 is domain-specific. Shown on the left is a static light scattering plot showing that Gus1ΔN mutant, which lacks the N terminal GST-like domain, does not assemble into large complexes after a temperature shift from 30 to 50° C. In contrast, Gus1N (a polypeptide consisting only of the the N-terminal GST-like domain) assembles into large aggregates rapidly (about 30-60 seconds) after a 30 to 50° C. temperature shift.

Gus1 possesses a eukaryote-specific N-terminal domain, which has been previously crystallized in isolation and shown to adopt a glutathione-S-transferase-like (GST-like) fold (FIG. 12). Applicants purified this domain (Gus1N) and the remaining core synthetase domain (Gus1ΔN). Gus1ΔN did not form large particles at any tested temperature up to 50° C. (FIG. 12), and showed a largely unperturbed structure (FIG. 12). In contrast, Gus1N readily assembled in vitro (FIG. 12). Gus1N is therefore necessary and sufficient for thermal assembly in vitro.

Gus1N behaves like a thermometer, transducing a change in temperature into self-assembly. To determine the sensitivity of this phenomenon, Applicants turned to dynamic light scattering (DLS), which unlike absorbance is capable of resolving particles at the nanometer scale. DLS revealed that this GST-like domain purified Gus1N adopts a GST-like fold and mediates binding of Gus1 to the cofactor Arc1, accelerating the aminoacylation rate of Gus1. In isolation, Gus1N rapidly assembled into large particles upon temperature shift (FIG. 12). Gus1N is thus necessary and sufficient for full-length Gus1's temperature-dependent self-assembly in vitro.

H1,N15-HSQC NMR of Gus1N at 20° C. and 43° C. indicate that the environment of the amide groups in Gus1N are similar at the two temperatures suggesting that self-assembly is mediated through a small conformational change and that most of the structure remains folded during assembly.

Figure 11:
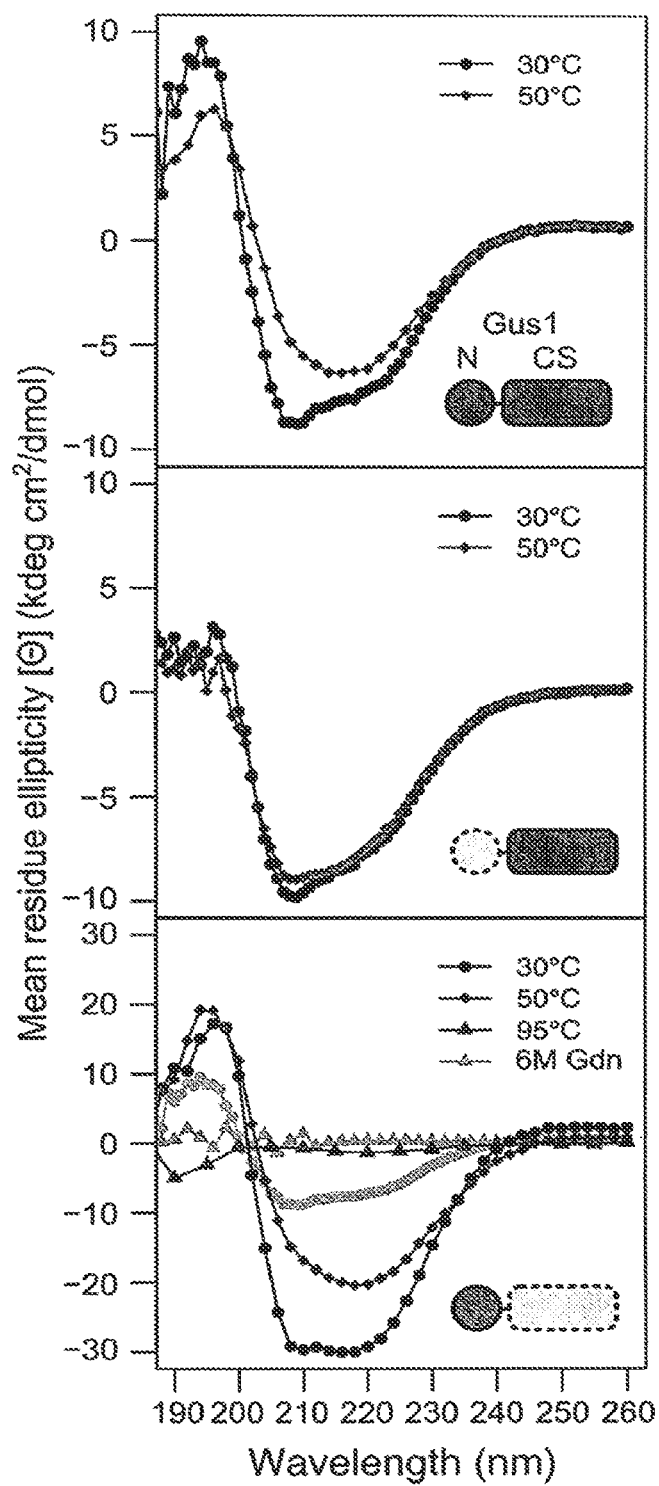
FIG. 11 shows that Gus1N (N-terminus of Gus1; also called the tsG domain) retains significant structure at assembly temperatures (50° C.). Data show circular dichroism spectra at 30° C. (lines with diamond points) and 50° C. (lines with circle points). Top, full-length Gus1 remains folded and shows a temperature-dependent conformational change. Middle: Gus1ΔN, lacking N-terminal GST-like domain, shows almost no change in response to temperature. Bottom, Gus1N, the isolated GST-like domain, is very well-structured (gray line shows full-length Gus1 for comparison), and displays a substantial temperature-dependent conformational change. Compare near-complete loss of structure with 6M Gdn (guanidinium HCl) and 95° C. heating, which denature Gus1N.

To determine the consequences of thermal shift on protein structure, Applicants collected far-ultraviolet circular dichroism (CD) spectra. The CD spectrum of full-length Gus1 at 30° C. revealed a well-folded structure; at 50° C., the protein remained well-folded while losing some helical structure (FIG. 11). The core synthetase, Gus1ΔN, showed minimal structural change in response to the temperature shift (FIG. 11). In marked contrast, Gus1N underwent a significant conformational change involving loss of helical structure, yet did so while preserving a highly ordered, largely α-helical structure (FIG. 11), whereas denaturation with 6M guanidine chloride (Gdn) disrupted Gus1N structure entirely (FIG. 11). These results closely match the in vitro assembly data, showing that at the residue and oligomer levels, the eukaryote-specific Gus1N domain is a temperature-responsive element linked to a temperature-insensitive enzyme.

Applicants speculate that the formation of large aggregates after a near-lethal heat shock results from damage to the heat-sensing system. A sensory system's necessary sensitivity to a stimulus predisposes that system to specific damage when the stimulus grows overwhelming, much as eyes are damaged by extremely bright light and ears by extremely loud sounds but not vice versa.

Repeated demonstrations that heat-shock-like responses can be generated by protein misfolding at normal growth temperatures have led to the hypothesis that heat shock is signaled and sensed by misfolded proteins. Notably, however, it has never been established that the temperature-induced misfolding of a native protein triggers the heat shock response. Applicants' results suggest the existence of an alternative channel of information provided by domain-specific thermal-shift-induced assembly of sensory proteins. These results strongly suggest that thermosensor-domain-mediated self-assembly, likely occurring in parallel in other proteins, is the first mechanistic step connecting a temperature change with stress-granule formation.

These results suggest a model in which environmental changes trigger proportionate changes in protein assembly, building up assembled proteins and reducing the population of freely diffusing proteins. Assembly may be reversible by cellular factors, or may require synthesis of new unassembled proteins. Applicants speculate that cellular chaperones, several of which are known to disaggregate misfolded proteins, also disaggregate assemblies. If so, this would suggest a remarkably simple regulatory mechanism.

Example 2

Rapid, Low-Cost Purification of Recombinant Tag-Free Proteins without Affinity Chromatography (Fenex)

A method is described for purifying a wide range of recombinant proteins employing only mild heating (<50° C.) and centrifugation (<20,000 g) achievable with standard benchtop equipment.

Purification of proteins is essential to many biological and industrial pursuits, such as characterization of protein structure and function and the development of drugs. Recombinant protein expression and purification is a common strategy, because affinity tags optimized for selective binding to columns in affinity chromatography systems can be appended to the target protein, enabling use of the same system to purify many proteins. Affinity chromatography equipment remains expensive and complex, making protein purification inaccessible to many.

Certain proteins are routinely purified without affinity chromatography. A kilogram of RNAse A was famously purified by the Armour Co. by boiling bovine pancreas and centrifuging the resulting stew; RNAse A is the only protein that remains in the supernatant after this treatment. Thermophilic proteins are often purified recombinantly from mesophilic hosts (such as E. coli) by heat-denaturing the host lysate at temperatures intolerable to the host but tolerated by the thermophile. These examples remain rare exceptions.

Purification methods including removal of affinity tags typically require two separate purification steps. Typical generic protein purification systems require purchase or production of columns, affinity resin, and liquid-handling systems to control flow, measure properties of the flowing liquid, and collect fractions. A single separation of lysate containing affinity-tagged protein on an affinity column most often yields recombinant protein with the affinity tag still attached. Digestion with an affinity-tagged protease and a second separation is required to yield tag-free protein. The present method achieves both separation and tag removal without any affinity columns, resin, or liquid-handling systems, making it far simpler, faster, easier, and cheaper than common approaches.

A method for purifying a target protein is diagrammed in FIG. 1, and is described below. The target protein is initially tagged and expressed in an arbitrary host organism; the method produces tag-free protein.

The method exploits a temperature-sensitive GST-like polypeptide ("tsG tag") fused to two proteins: a target protein of interest, and a protease. The tsG polypeptide has the property, discovered by Applicants and as yet unreported, of rapidly self-assembling in response to increases in temperature.

One embodiment comprises sequestering the target protein away from soluble host contaminants by heat-induced tsG-tag self-assembly, releasing the target protein from heat-aggregatable host contaminants by proteolysis with a tsG-tagged protease, and finally removing heat-aggregatable host contaminants, the protease, and the cleaved tag by heat-induced tsG self-assembly.

The self-assembly of tsG results in large particles which pellet readily upon centrifugation at 10,000-20,000 g, attainable on a typical benchtop microcentrifuge.

Figure 2:
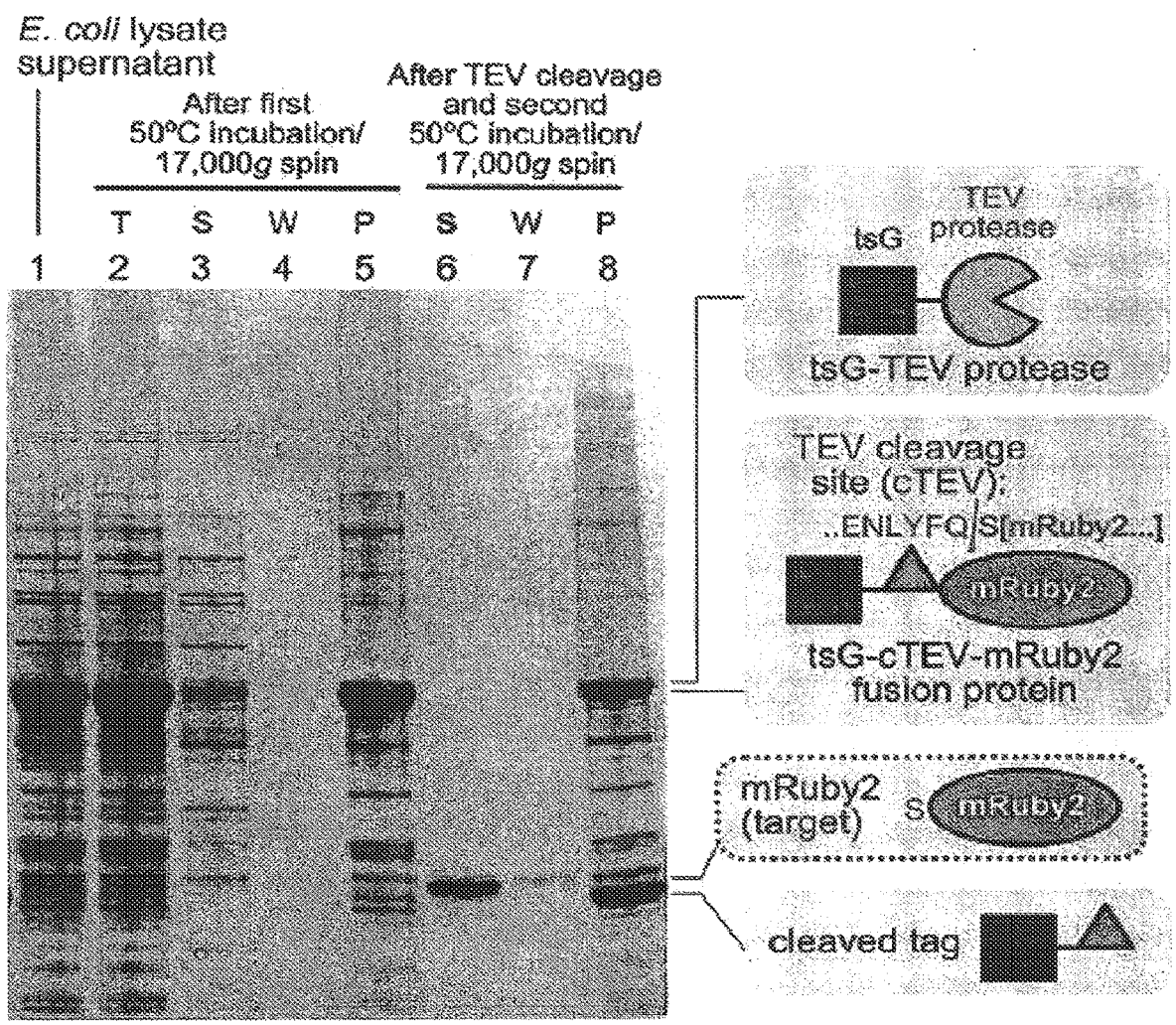
FIG. 2. Purification of target protein mRuby2 (red fluorescent protein) from crude *E. coli* lysate, illustrated on an SDS-PAGE gel developed with Coomassie stain. Here, the protease is tsG-TEV, tobacco etch virus protease, which cleaves the seven-amino-acid sequence ENLYFQS (SEQ ID NO:19) between Q and S, leaving a single serine residue attached to the target protein. The target protein is mRuby2, a red fluorescent protein variant. Lane 1, *E. coli* lysate supernatant after centrifuging out cell debris. Lanes 2-5, total (T) protein, supernatant (S), wash (W), and pellet (P) material after first 50° C./10 min treatment and centrifugation at 17,000 g for 10 minutes. Lanes 6-8: supernatant, wash, and pellet material after 2 h incubation with added tsG-TEV protease and second 50° C./10 min treatment. Lane 6 contains substantially pure mRuby2 of the expected molecular weight.
Figure 3:
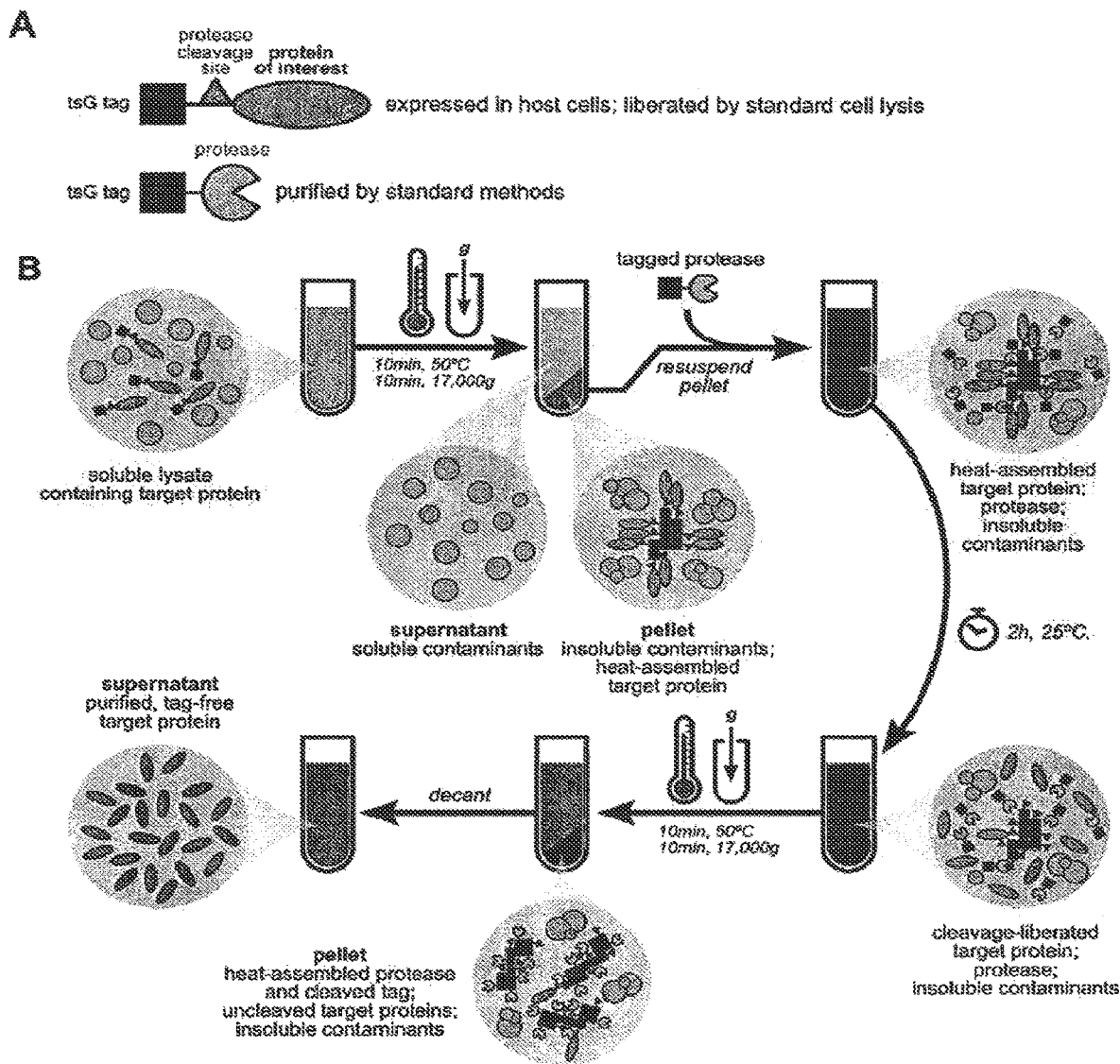
FIG. 3. Detailed description of the purification scheme described in FIG. 1. A, Protein components. The target protein is expressed as a fusion protein with a cleavable temperature-sensitive GST-like tag (tsG tag). A protease capable of cleaving the tag is purified once by standard affinity methods. B, Details of the method. Soluble lysate containing the tagged target protein is passed through a set of steps to generate soluble, tag-free target protein. No affinity chromatography is employed. The method can be completed in under three hours and requires only a benchtop centrifuge.
Figure 4A:
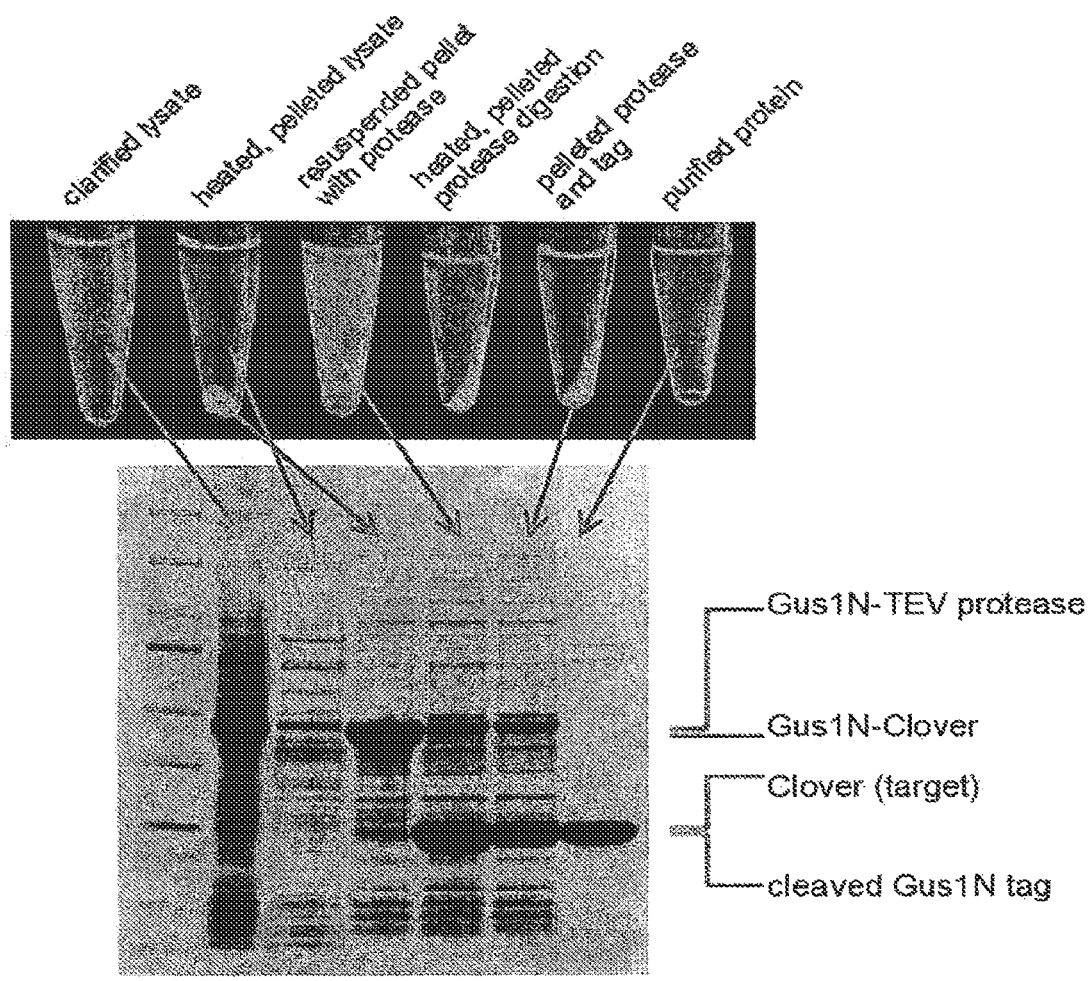
FIG. 4A-4B.
Figure 4B:
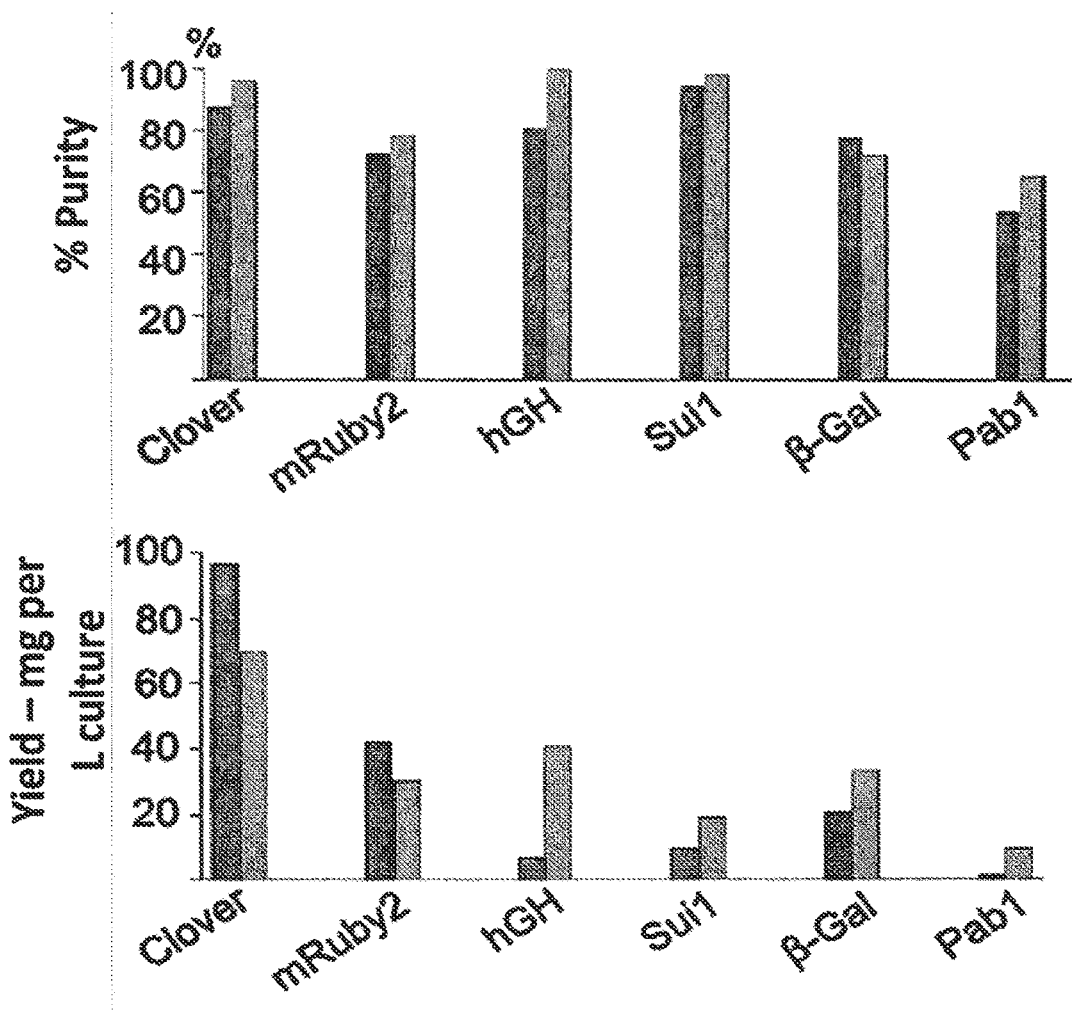

FIG. 2 demonstrates purification of a test protein, the red fluorescent protein mRuby2, from E. coli using one embodiment of the method. Briefly, E. coli were cultured and lysed using methods known to those skilled in the art, such as mechanical or chemical lysis. The soluble lysate containing the fusion protein is heated for 10 minutes at 50 degrees Celsius and then subjected to centrifugation for 2 minutes at 17,000 g. The SDS-PAGE gel represents protein profile from samples during the process of the method. Lane 1 shows the starting material after cell lysis. Lanes 2-5, total (T) protein, supernatant (S), wash (W), and pellet (P) material after first 50° C./10 min treatment and centrifugation at 17,000 g for 10 minutes. The supernatant comprising soluble contaminants was discarded. The remaining pellet comprises insoluble contaminants and the heat-assembled Gus1N-mRuby2. Next, a second fusion protein comprising Gus1N and tobacco etch virus (TEV) protease was added to the remaining pellet, which was suspended in TEV cleavage buffer. The mixture was heated at 25 degrees Celsius for 2 hours in which the TEV protease liberated the mRuby2 from the Gus1N. The mixture was then heated for 10 minutes at 50 degrees Celsius to aggregate mRuby2-free Gus1N protein. Insoluble contaminants and Gus1N were removed from mRuby2 by centrifugation for 2 minutes at 17,000 g. The soluble mRuby2 was decanted from the pellet. Lanes 6-8 of the SDS-PAGE in FIG. 2 shows the supernatant, wash, and pellet material after 2 h incubation with added tsG-TEV protease and second 50° C./10 min treatment. Lane 6 contains substantially pure mRuby2 of the expected molecular weight. FIG. 3 illustrates the steps involved at the molecular level. FIG. 4A shows the purification of the fluorescent protein, Clover, using the current embodiment. FIG. 4B compares purification of six different proteins (Clover, mRuby2, hGH, Suil, 13-Gal, Pab1) using the current embodiment with purification using the traditional His-tag method. Certain embodiments of the method described herein achieves comparable purity to the His-tag method.

Certain embodiments of this method allows protein purification more cheaply and rapidly, with less equipment and less effort, than any method of which Applicants are aware. They are applicable to purification of any soluble proteins, particularly for initial or high-throughput studies.

In addition to its simplicity, the method has proven to be unusually good at removing the protease and uncleaved fusion protein from the final purification. This is often a challenge for existing affinity purification schemes, which, even with a second round of purification, fail to completely remove the uncleaved protein.

In principle, a very wide range of proteins are amenable to purification by various embodiments of the invention.

Preferably, for certain embodiments, target proteins are stable at temperatures and durations necessary for assembly of the tsG domains. Reaction temperatures can be lowered by engineering of the tsG domain. In certain embodiments, however, such as the embodiment shown in FIG. 19, the target protein is not heated to the temperature necessary for assembly of the tsG domains.

Preferably, for certain embodiments, target proteins are tolerant of fusion to the tsG domain and protease cleavage site. Most affinity purification methods require fusions of some sort (alternatives are antibodies and affinity reagents designed to be specific to the protein of interest), and both the type of domain (GST-like) and the cleavage site employed in Applicants' proof-of-concept experiment are widely employed in protein purification experiments.

Preferably, the target protein is soluble under the conditions employed.

For some applications, subsequent purification steps may be used.

Engineering a wide range of proteases by fusing them to the tsG tag will enable utilization of a wide range of protease cleavage sites. Because the selectivity and activity of proteases vary, such a library of proteases would enable the purification of an increased number of protein targets.

Applicants have discovered a range of domains exhibiting temperature-triggered self-assembly. In principle, any of these can be used in place of the tsG tag demonstrated here.

The use of centrifugation to separate assemblies is not essential. The principle is separation by size, which can also be achieved by filtration.

Example 3

Genetically-Encoded Affinity Resin (Gear) for Purification of C-Tag Myosin V

Applicants have developed a system in which the Gus1N self-assembling polypeptide is genetically fused to the PDZ domain, which binds a short polypeptide called a C-tag. The PDZ/C-tag system has been previously described (Huang et al. 2009). Using this system, Applicants have purified myosin V in its active form. Myosin V is a molecular motor protein that is responsible for intracellular cargo transportation in cells. The protein is a dimer which possesses so-called "legs" that allow it to "walk" along the actin filaments, and cargo-binding domains that bind what the myosin actually transports, for example vesicles containing RNA. The process of "walking" is driven by ATP hydrolysis. Myosin V (MV) itself is a massive protein, around 137 kDa. These features make myosin V a very difficult protein to both purify and work on. Usually, it is purified via FLAG resin, so it binds to agarose beads coated with anti-FLAG tag antibodies and then eluted with a FLAG peptide that outcompetes bound myosins. The anti-FLAG resin is very expensive, and just 10 mL of an anti-FLAG resin can cost about $1790.

Expression of Gus1PDZ (GEAR)

Figure 16:
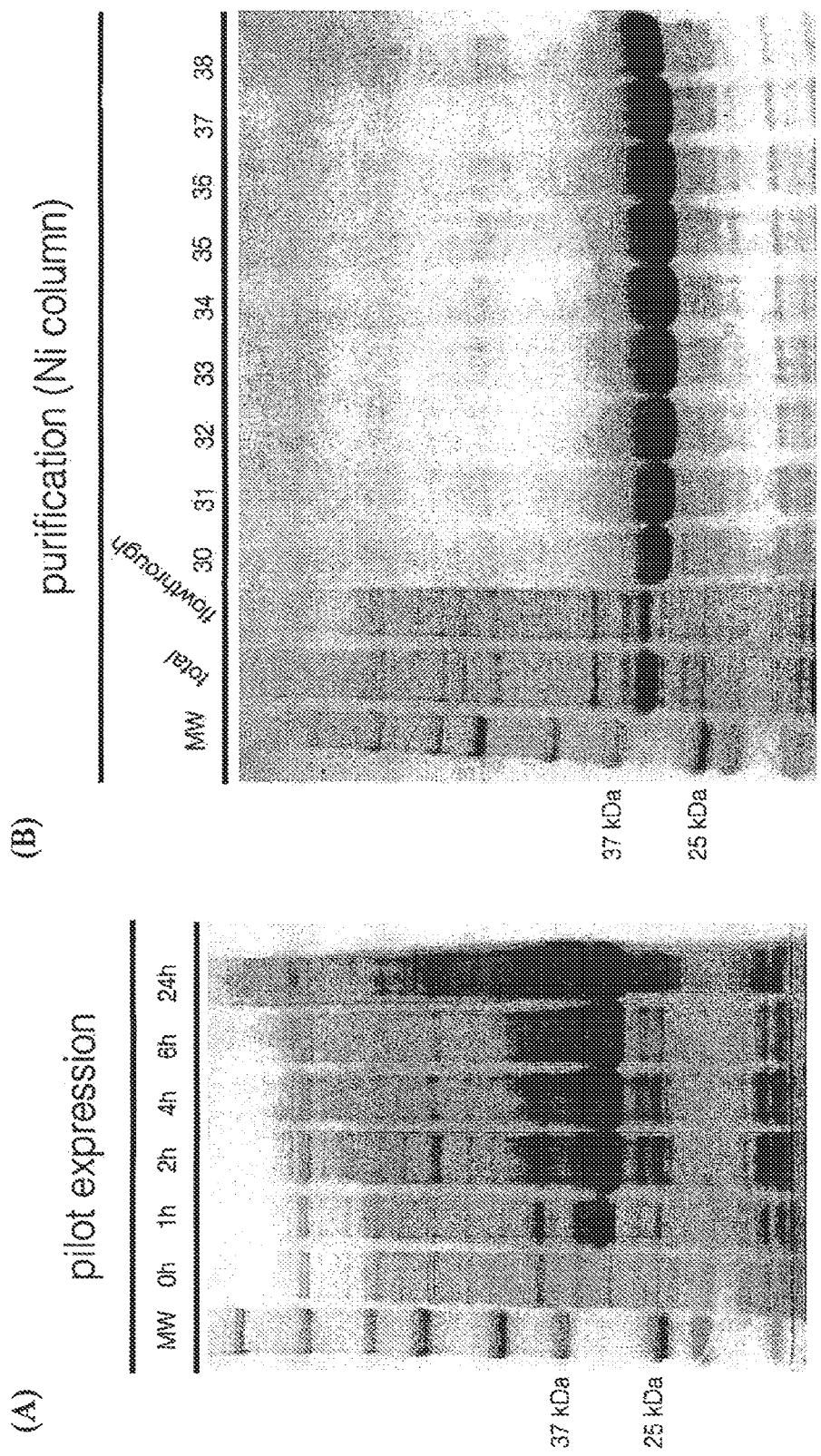
FIG. 16A-B shows Gus1N-PDZ expression (A) and purification (B) using a Ni column. Gus1N-PDZ protein expresses very well under standard conditions, namely OD=0.6, 1 mM IPTG at 30° C. and a good level of expression is achieved after about 4 hours Only one-step purification was required to purify the protein. A Ni column was used for the purification, and the average yield from two separate purifications is 17.53 mg/L of cell culture.

Gus1PDZ expresses very well under standard conditions, namely OD=0.6, 1 mM IPTG at 30° C. and satisfactory expression is achieved after about 4 hours (FIG. 16A). One advantage of the Gus1NPDZ is that only a one-step purification is required to achieve a highly purified product. In this example, Gus1NPDZ was purified using affinity chromatography with the $Ni^{2+}$ column. The average yield from two separate purifications is 17.53 mg/L of cell culture (FIG. 16B).

To make this process less expensive and totally lab made, Applicants created a fusion protein that would have a self-assembling domain as a resin-forming domain and an affinity domain having affinity to tagged Myo V. Gus1N was chosen as the resin-forming domain. Gus1N is an N-terminal domain of glutamyl-tRNA synthetase which causes either this enzyme or different proteins tagged with it to self-assemble upon a few minutes of heat shock. Once assembled, Gus1N-tagged molecules form complex meshworks. So now once Gus1N were linked to an affinity domain and heat-shocked it would provide lots of binding sites for the target. The domain we decided to choose to be fused to Gus1N to make GEAR (Genetically-Encoded Affinity Resin) is PDZ. The PDZ domain is a common structural domain of 80-90 amino-acids found in the signaling proteins of bacteria, yeast, plants, viruses, and animals. PDZ is an acronym combining the first letters of three proteins—post synaptic density protein (PSD95), *Drosophila* disc large tumor suppressor (Dlg1), and zonula occludens-1 protein (zo-1) which were first discovered to share the domain. PDZ domains have previously been referred to as DHR (Dlg homologous region) or GLGF (glycine-leucine-glycine-phenylalanine) domains. Engineering of its ligands allowed for the creation of a C-tag (SEQ ID NO:13). The major advantage of c-tag is that it's bound by PDZ quite tightly yet is easily releasable. And this release is possible by using the elution peptide (SEQ ID NO:14) which outcompetes proteins bound to PDZ tagged with c-tag.

Figure 15:
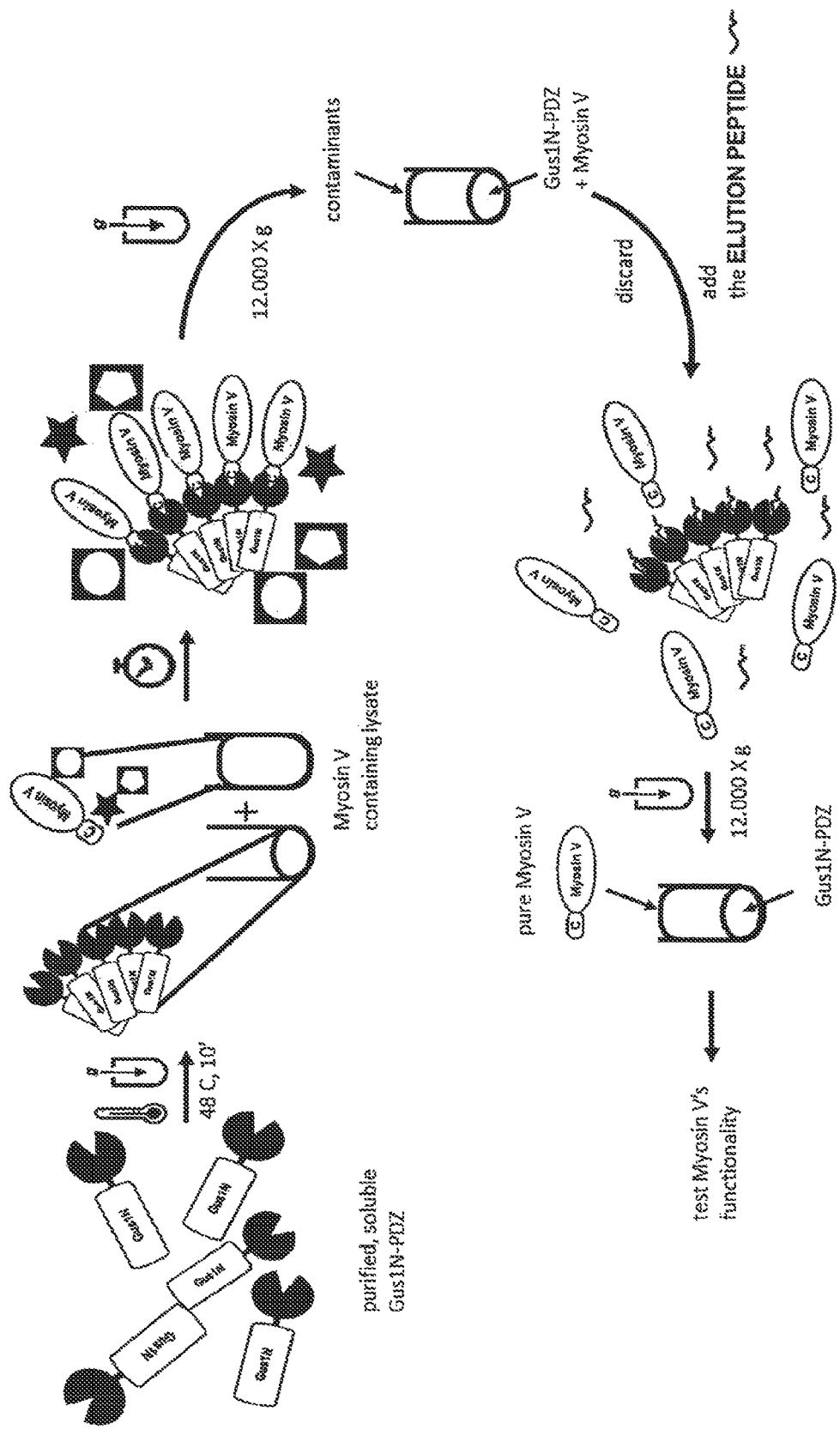
FIG. 15 depicts a purification scheme using the methods of the disclosure. This purification scheme is further described in Example 3. Briefly, the scheme depicts the steps: (1) heat-shock Gus1N-PDZ for 10 minutes at 48° C.; (2) pellet and mix with myosin V (MV)-containing lysate; (3) incubate together to let MV bind to PDZ; (4) centrifuge and discard supernatant (contaminants); (5) add the elution peptide which outcompetes c-tagged MV and releases it from PDZ; (6) centrifuge, product is purified MV in the supernatant and Gus1N-PDZ in the pellet.

The procedure for purification is depicted in FIG. 15. Briefly, the Gus1N-PDZ protein is expressed and purified from *E. coli*, then heat-shocked at 48° C. for 10 minutes to cause self-assembly, generating a solid support decorated with PDZ domains. This can be referred to as a resin. MV-Ctag is expressed in cells, which are lysed. The lysate is incubated with the resin, then centrifuged at 12,000 g for 5 minutes. The supernatant is discarded and the pellet is washed. Then elution peptide is added. This peptide has higher affinity for PDZ than does Ctag, so the bound MV-Ctag is released from the resin. Another 12,000 g spin is performed, and the supernatant is retained. The supernatant contains highly purified MV-Ctag. In this purification method, the target protein (MV; i.e. second target protein) is never exposed to a heat shock.

Expression of Gus1PDZ

Gus1PDZ expresses very well under standard conditions, namely OD=0.6, 1 mM IPTG at 30 C and satisfactory expression is achieved after about 4 hours. One advantage of the Gus1NPDZ is that only one-step purification is required to get a highly purified product. The Ni column was used for purification of Gus1NPDZ. The average yield from two separate purifications is 17.53 mg/L of cell culture (FIG. 16B).

To make this process less expensive and totally lab made, Applicants created a fusion protein that would have a self-assembling domain as a resin-forming domain and an affinity domain having affinity to tagged Myosin V. Gus1N was chosen as the resin-forming domain. Once assembled, Gus1N-tagged molecules form complex meshworks. So now once Gus1N was linked to an affinity domain and heat-shocked it would provide a lot of binding sites for the target. Applicants fused PDZ to Gus1N to make GEAR (Genetically-Encoded Affinity Resin). The PDZ domain is a common structural domain of 80-90 amino-acids found in signaling proteins of bacteria, yeast, plants, viruses, and animals. PDZ is an acronym combining the first letters of three proteins—post-synaptic density protein (PSD95), *Drosophila* disc large tumor suppressor (Dlg1), and zonula occludens-1 protein (zo-1) which were first discovered to share the domain. PDZ domains have previously been referred to as DHR (Dlg homologous region) or GLGF (glycine-leucine-glycine-phenylalanine) domains. Engineering of the PDZ domain's natural ligand allowed for the creation of a C-tag (SEQ ID NO:13). An advantage of C-tag is that the binding to PDZ, though quite tightly, is easily releasable. This release is possible by using the elution peptide (SEQ ID NO:14) which outcompetes C-tagged proteins bound to PDZ.

The procedure for purification in one embodiment is depicted in FIG. 15. Briefly, the Gus1N-PDZ protein is expressed and purified from *E. coli*, using standard methods or FENEX. The purified Gus1N-PDZ is then heat-shocked at 48° C. for 10 minutes to cause self-assembly, generating a solid support decorated with PDZ domains. This can be referred to as a resin. MV-C-tag is expressed in cells, which are then lysed. The lysate is incubated with the resin, then centrifuged at 12,000 g for 5 minutes. The supernatant is discarded and the pellet is washed in buffered solution. Then the elution peptide is added. This peptide has a higher affinity for the PDZ domain than the C-tag, so the bound MV-Ctag is released from the resin. Another 12,000 g spin is performed, and the supernatant is retained. The supernatant contains highly purified MV-C-tag. In this purification method, the target protein (MV; i.e., a second target protein) is never exposed to a heat shock.

Purification of Myosin V Using GEAR Compared to FLAG Purification Methods

Figure 20:
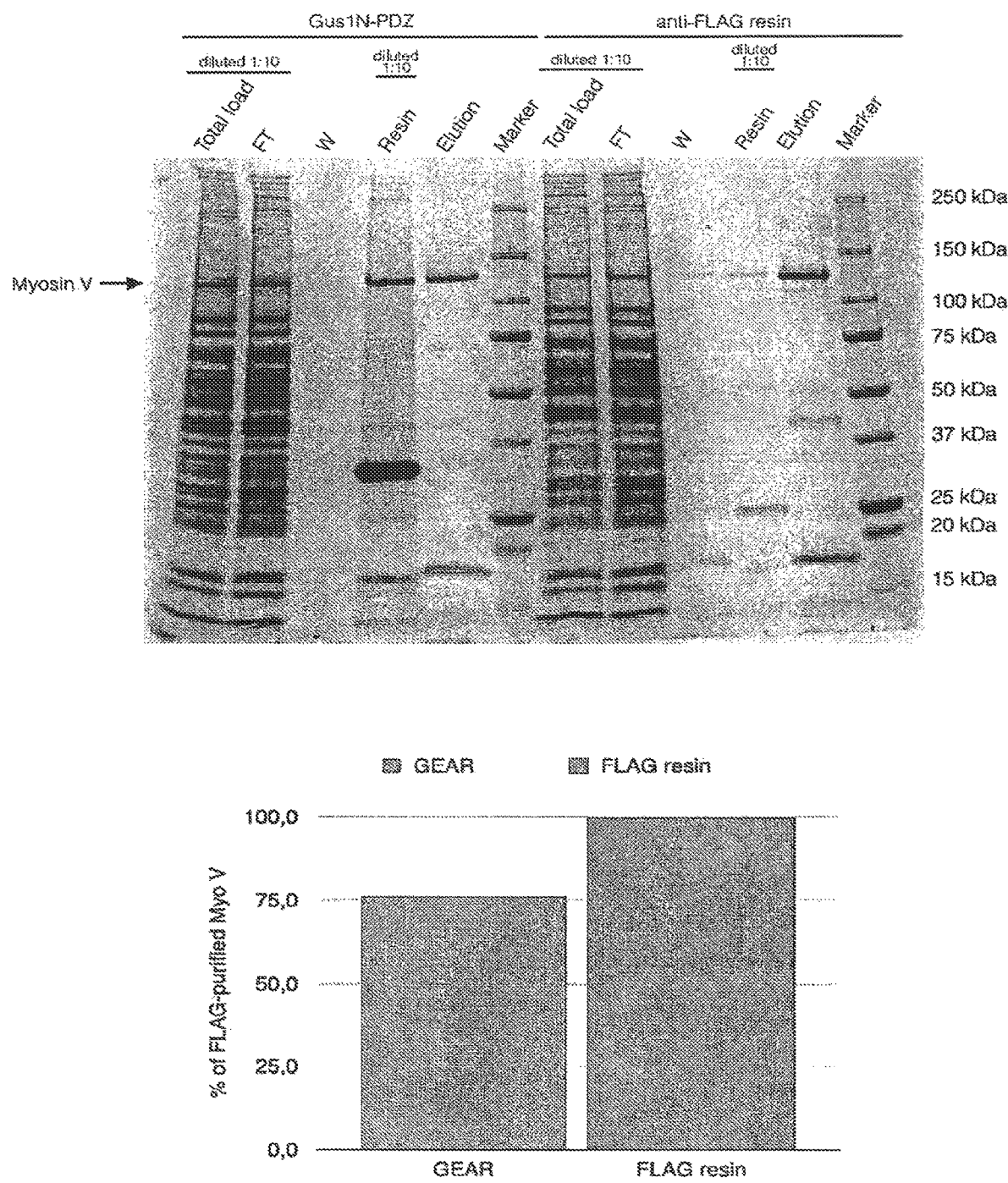
FIG. 20 depicts the purification of Myosin V using the methods described in Example 3 compared to traditional methods using anti-FLAG resin. The Gus1N-PDZ used was 13 mg for the whole preparation. 250 mL of crude extract was used. The peptide used was 600 µL of 400 µM. GEAR (Genetically-Encoded Affinity Resin) refers to the Gus1N-PDZ resin. As can be seen in the elution lanes, MV was purified in an amount that was comparable to purification using an anti-FLAG tag method. The amount of MV purified by the Gus1N-PDZ method was 25% less, however, the degree of purity was higher, and the capacity of the resin was higher, since a large portion of uneluted MV can be seen.
Figure 21:
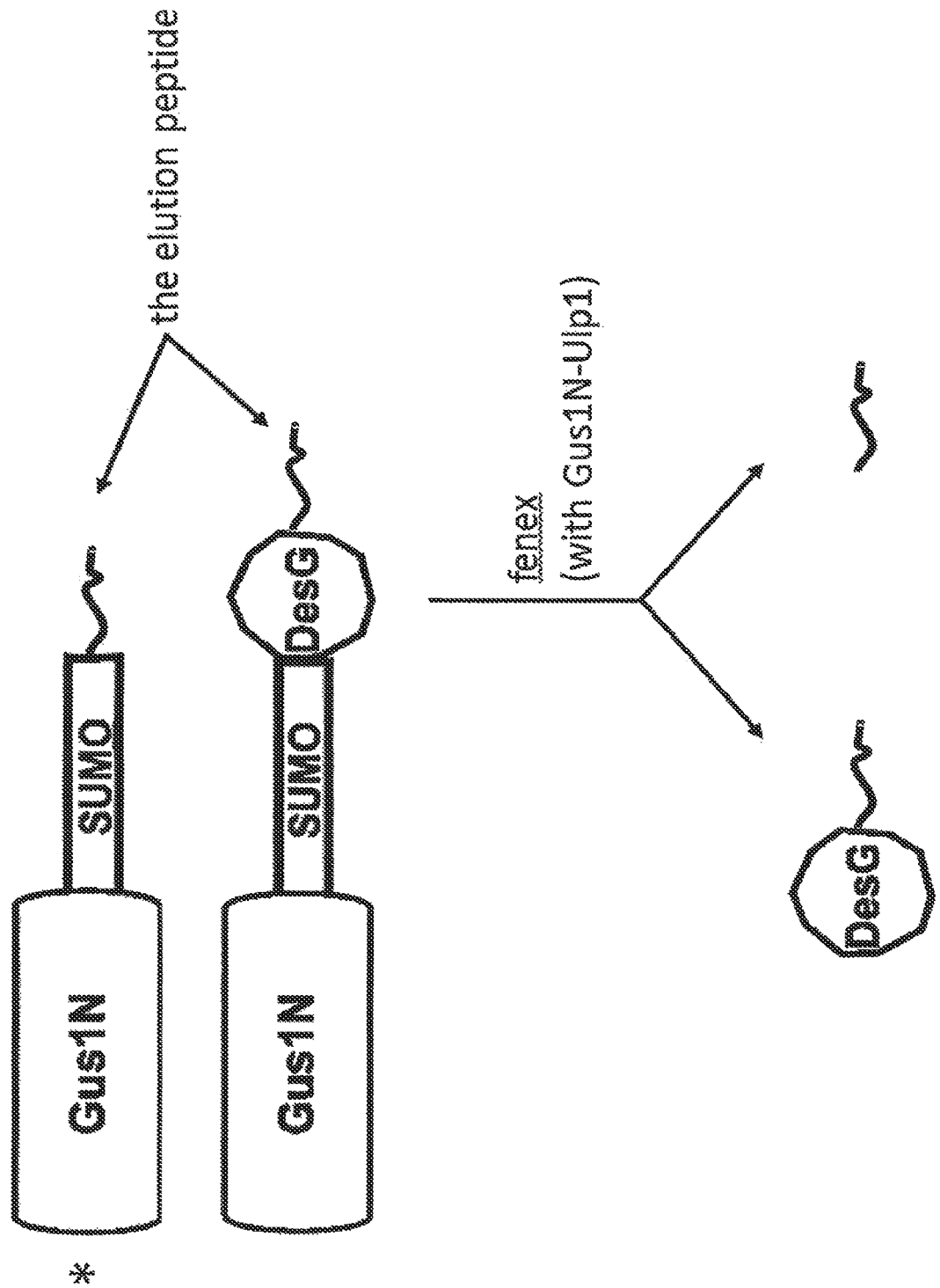
FIG. 21—The elution peptide (EP) for competing Ctag-tagged protein off of Gus1N-PDZ resin may be produced using the Gus1N system. A Gus1N-tevC-EP construct is expressed in *E. coli*, and purified using heat/centrifugation as described in Example 2. The elution peptide may then be used as in Example 3.

Next, GEAR purification was compared to anti-FLAG resin purification. As can be seen by comparing the elution lanes, MV was successfully purified using GEAR in an amount that was comparable to the anti-FLAG resin. The amount of MV purified by the Gus1NPDZ method was 25% less, however, the degree of purity was higher, and the capacity of the resin was higher, since a large portion of uneluted MV can be seen in the resin fraction compared to the resin fraction using FLAG purification (FIG. 20).

To test whether the purified MV was a functional protein, a gliding filament assay was performed. In this assay, a coverslip was coated with the GEAR-purified myosins so that the legs are exposed outward, and actin filaments that interact with the myosins were added. Next, ATP-containing buffer that triggers myosin activity was added, causing the actin filaments to glide along the immobilized myosins. Most of the actin filaments moved, indicating that the purified myosins were functional.

Purification of Clover using GEAR

Figure 17:
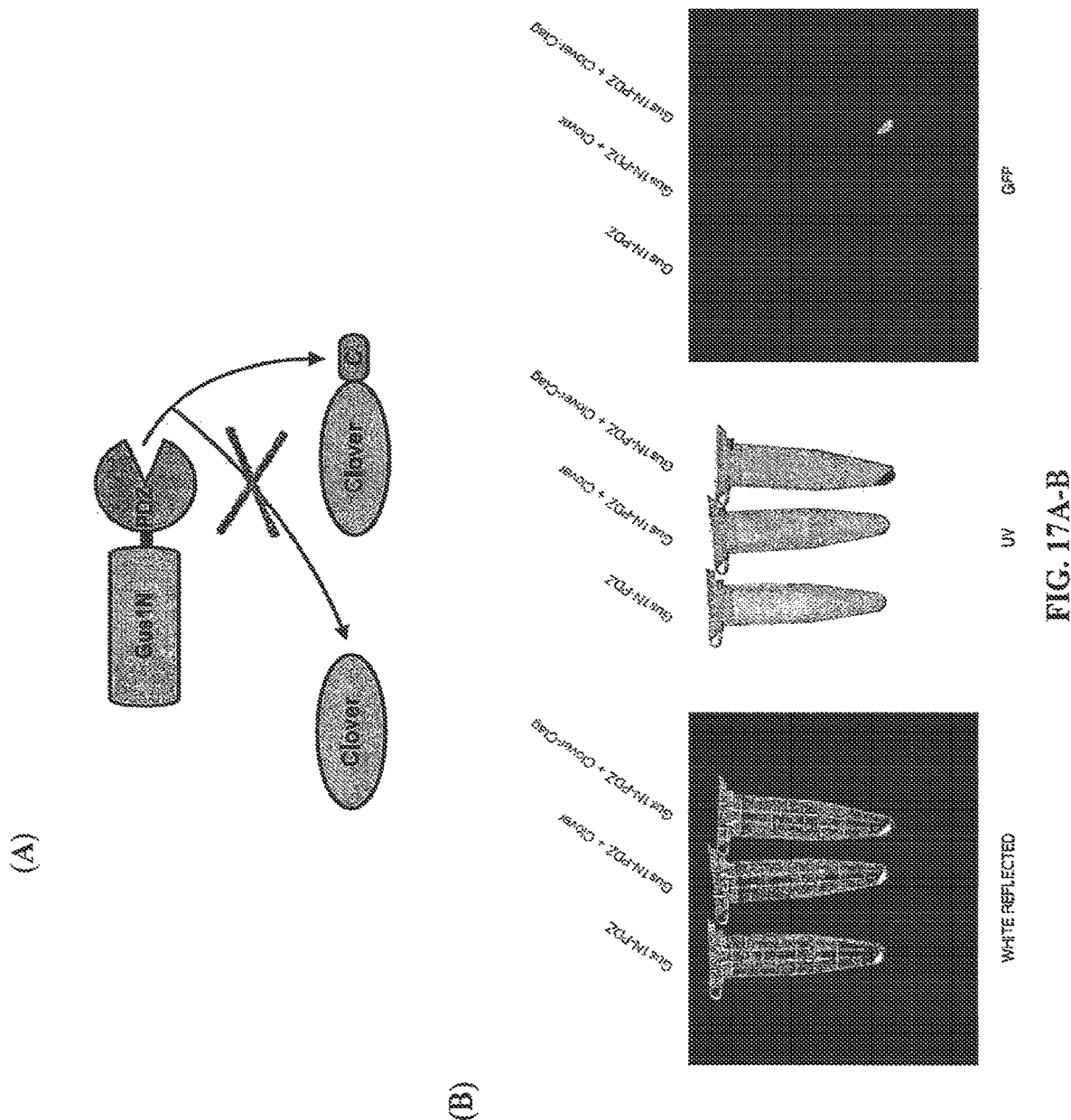
FIG. 17A-B shows the specificity of the Gus1N-PDZ for the target. Shown in A is a cartoon depiction of the specificity assay. Heat-shocked Gus1N-PDZ was incubated with either Clover-C or tagless Clover, the pellets were washed, and then the pellets were visualized by using both UV and GFP channels. Shown in B are the results that demonstrate that Gus1N-PDZ binds specifically to clover-Ctag and not untagged clover (second and third panel showing UV and GFP results). The only pellet to emit any light is the one incubated with tagged Clover.
Figure 18:
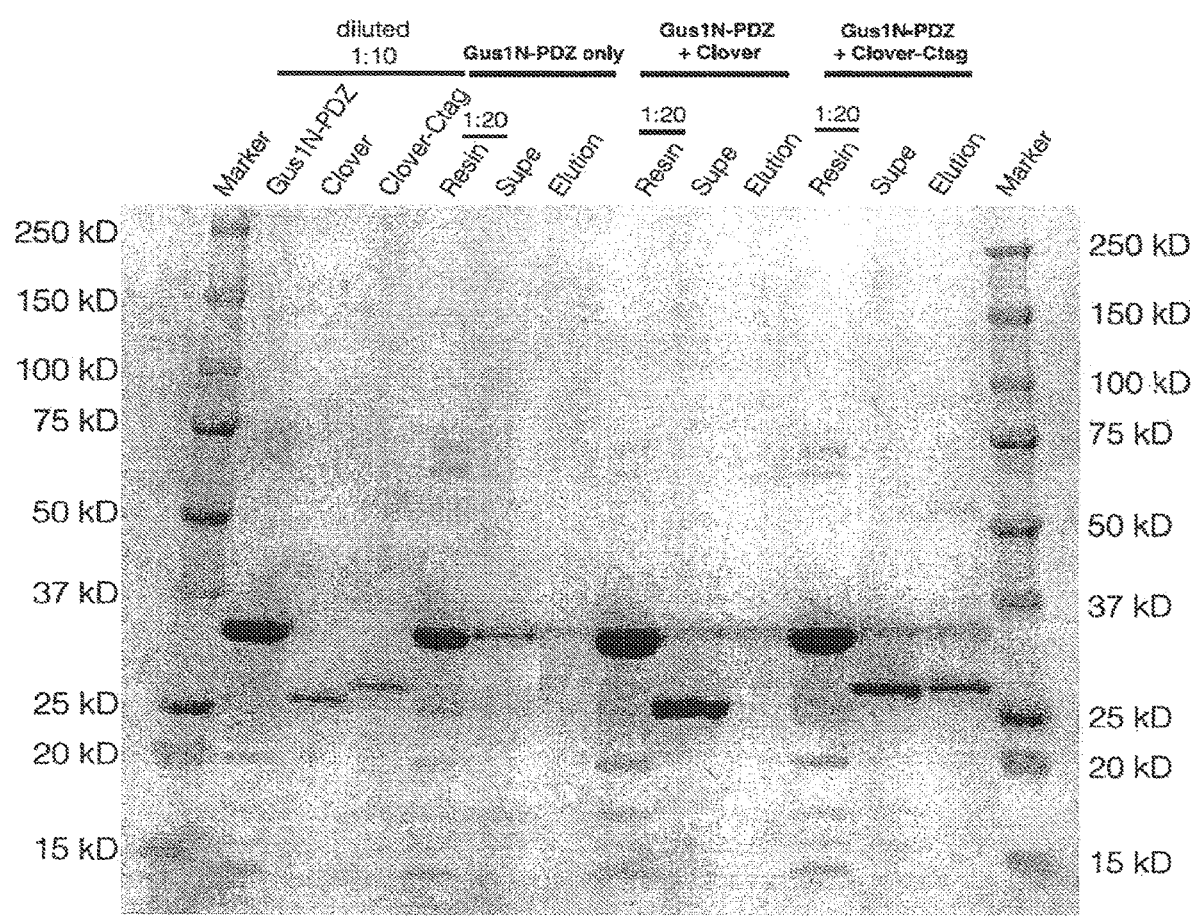
FIG. 18 demonstrates that Gus1N-PDZ binds its targets specifically. This figure is similar to FIG. 17, however, elution was performed using the elution peptide in this experiment. Each sample was split into three fractions which are resin after elution, supernatant (fraction not bound to Gus1NPDZ), and eluted fractions. As can be seen in the figure, nothing eluted in case of tagless Clover while in the case of C-tagged Clover there is got eluted Clover-C in the eluted fraction. Comparing the lanes for Gus1N-PDZ—elution, Gus1N-PDZ+Clover—elution, and Gus1N-PDZ+Clover-Ctag—elution, only the last elution lane had the Clover protein. Therefore, the Gus1N-PDZ provides for a resin with little or no background contamination. These results are consistent with previous results (e.g., FIG. 17). The Gus1N-PDZ used was 583 μg, the Clover or Clover-Ctag used was 100 μL of 30 μM. The peptide used was 100 μL of 200 μM.

The binding specificity of Gus1N-PDZ was tested in two examples. In the first example, heat-shocked Gus1N-PDZ was incubated with either Clover-C-tag (Clover-C) or tagless Clover. The mixture was pelleted by centrifugation, the pellets were washed, and then visualized with both UV and GFP channels. As shown in FIG. 17, the only pellet to emit any fluorescence is the one incubated with C-tagged Clover. In the second specificity example, a similar experimental procedure is performed, but elution was achieved using the elution peptide. In FIG. 18, each sample was split into three fractions and analyzed by SDS-PAGE: (1) resin after elution, (2) supernatant or supe (the fraction not bound to Gus1NPDZ) and (3) eluted fractions (elution). In the case of tagless Clover, Clover protein was found in the supernatant fraction and nothing was eluted. C-tagged Clover yielded Clover-C in the elution fractions. Purified components diluted 1:10 were also loaded onto the gel as a control.

These results are consistent with previous results described herein using this method.

Figure 19:
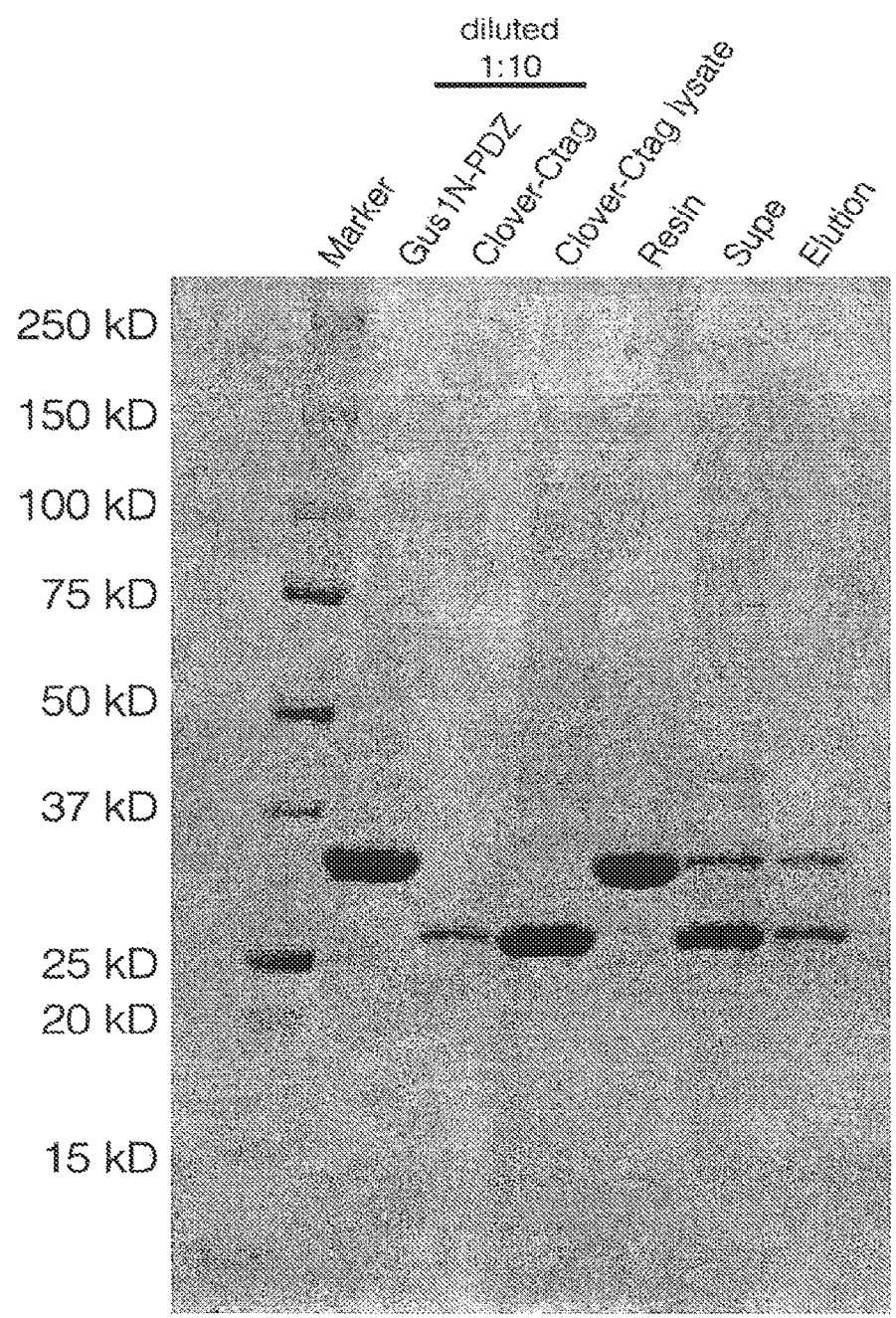
FIG. 19 shows the purification of Clover-Ctag using Gus1N-PDZ according to the methods described in Example 3. This experiment was done to determine if Gus1N-PDZ could be used to purify out a target protein from a complex lysate. Clover-C was expressed in bacteria, and the lysate was pre-shocked with Gus1N-PDZ. Following this, the elution was performed. The Gus1N-PDZ used was 583 µg, the Clover or Clover-Ctag lysate used was 100 µL. The peptide used was 100 µL of 200 µM. Clover-C was successfully purified from the lysate with just some residual Gus1N-PDZ.

It was then determined whether Gus1N-PDZ could be used to purify out a target protein from a complex lysate. To do so, Clover-C was expressed in bacteria, the lysate was incubated with pre-heat shocked Gus1NPDZ. Next, the elution was performed (FIG. 19). Clover-C was successfully purified with only a little residual Gus1N-PDZ.

This disclosure relates to variations of the above-described purification method. In one variation, the target protein X is expressed as an X[cleavage site]Ctag, where [cleavage site] represents the recognition amino acid sequence for a protease, such as TEV. Instead of an excess of elution peptide (EP), a protease-C-tag fusion protein is added at low concentrations. The target protein is released by cleavage off of the resin, and the protease is recruited to the resin. In further variations, other affinity domains and other release peptides are used. The resin concept can be used in virtually any application where beads or other solid supports are now used, such as depletion of a target protein from a mixture. In virtually all cases, the fact that beads are spherical or separate from one another is irrelevant.

Although certain embodiments have been described above with a certain degree of particularity, or with reference to one or more individual embodiments, those skilled in the art could make numerous alterations to the disclosed embodiments without departing from the scope of this invention. As such, the illustrative embodiments are not intended to be limited to the particular forms disclosed. Rather, they include all modifications and alternatives falling within the scope of the claims, and embodiments other than those shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

REFERENCES

The following references (including patent documents and non-patent literature), to the extent that they provide exemplary procedural or other details supplementary to those set forth herein, are each specifically incorporated herein by reference, each in its entirety.

Nover, L., Scharf, K. D. & Neumann, D. Formation of cytoplasmic heat shock granules in tomato cell cultures and leaves. Molecular and cellular biology 3, 1648-1655 (1983).

Grousl, T. et al. Robust heat shock induces eIF2alpha-phosphorylation-independent assembly of stress granules containing eIF3 and 40S ribosomal subunits in budding yeast, *Saccharomyces cerevisiae*. Journal of cell science 122, 2078-2088, doi:10.1242/jcs.045104 (2009).

Grousl, T. et al. Heat shock-induced accumulation of translation elongation and termination factors precedes assembly of stress granules in *S. cerevisiae*. PloS one 8, e57083, doi:10.1371/journal.pone.0057083 (2013).

Rinnerthaler, M. et al. Mmi1, the yeast homologue of Mammalian TCTP, associates with stress granules in heat-shocked cells and modulates proteasome activity. PloS one 8, e77791, doi:10.1371/journal.pone.0077791 (2013).

Kimball, S. R., Horetsky, R. L., Ron, D., Jefferson, L. S. & Harding, H. P. Mammalian stress granules represent sites of accumulation of stalled translation initiation complexes. American journal of physiology. Cell physiology 284, C273-284, doi:10.1152/ajpcell.00314.2002 (2003).

Kedersha, N. & Anderson, P. Regulation of translation by stress granules and processing bodies. Progress in molecular biology and translational science 90, 155-185, doi:10.1016/S1877-1173(09)90004-7 (2009).

Anderson, P. & Kedersha, N. Stress granules: the Tao of RNA triage. Trends in biochemical sciences 33, 141-150, doi:10.1016/j.tibs.2007.12.003 (2008).

Yao, G. et al. PAB1 self-association precludes its binding to poly(A), thereby accelerating CCR4 deadenylation in vivo. Molecular and cellular biology 27, 6243-6253, doi:10.1128/MCB.00734-07 (2007).

Simon, E. & Seraphin, B. A specific role for the C-terminal region of the Poly(A)-binding protein in mRNA decay. Nucleic acids research 35, 6017-6028, doi:10.1093/nar/gkm452 (2007).

Simader, H. et al. Structural basis of yeast aminoacyl-tRNA synthetase complex formation revealed by crystal structures of two binary sub-complexes. Nucleic acids research 34, 3968-3979, doi:10.1093/nar/gkl560 (2006).

Simader, H., Hothorn, M. & Suck, D. Structures of the interacting domains from yeast glutamyl-tRNA synthetase and tRNA-aminoacylation and nuclear-export cofactor Arc1p reveal a novel function for an old fold. Acta crystallographica. Section D, Biological crystallography 62, 1510-1519, doi:10.1107/S0907444906039850 (2006).

Graindorge, J. S., Senger, B., Tritch, D., Simos, G. & Fasiolo, F. Role of Arc1p in the modulation of yeast glutamyl-tRNA synthetase activity. Biochemistry 44, 1344-1352, doi:10.1021/bi049024z (2005).

Ananthan, J., Goldberg, A. L. & Voellmy, R. Abnormal proteins serve as eukaryotic stress signals and trigger the activation of heat shock genes. Science 232, 522-524 (1986).

Trotter, E. W. et al. Misfolded proteins are competent to mediate a subset of the responses to heat shock in *Saccharomyces cerevisiae*. The Journal of biological chemistry 277, 44817-44825 (2002).

Mitchell, S. F., Jain, S., She, M. & Parker, R. Global analysis of yeast mRNPs. Nature structural & molecular biology 20, 127-133, doi:10.1038/nsmb.2468 (2013).

Price-Carter, M., Fazzio, T. G., Vallbona, E. I. & Roth, J. R. Polyphosphate kinase protects *Salmonella enterica* from weak organic acid stress. Journal of bacteriology 187, 3088-3099, doi:10.1128/JB.187.9.3088-3099.2005 (2005).

Anderson, P. & Kedersha, N. Stressful initiations. Journal of cell science 115, 3227-3234 (2002).

Barany & Merrifield, In: *The Peptides*, Gross and Meienhofer (Eds.), Academic Press, NY, 1-284, 1979 (1979)

Huang et al., *J. Mol. Biol.* 392:1221-21 (2009)

Lee et al., *PLoS One* 8:367902 (2013)

Merrifield, *Science,* 232(4748):341-347, (1986)

Sha et al., *PNAS* 110:14924-9 (2013)

Stewart & Young, In: *Solid Phase Peptide Synthesis,* 2d. ed., Pierce Chemical Co., 1984

Tam et al., *J. Am. Chem. Soc.,* 105:6442, 1983 (1983)

Netzger et al. (2009), "Innate immune and chemically triggered oxidative stress modifies translational fidelity," *Nature* 462:522-526

U.S. Pat. No. 5,206,347

---

The invention claimed is:

1. A fusion protein comprising:
   (a) a self-assembly domain comprising SEQ ID NO: 9 and
   (b) a target protein;
   wherein the target protein is a protease,
   wherein the fusion protein is capable of forming protein aggregates under appropriate conditions.

2. The fusion protein of claim 1, wherein the appropriate conditions are temperature conditions of greater than or equal to 35° C.

3. The fusion protein of claim 1, wherein the self-assembly domain is less than 250 amino acids in length.

4. The fusion protein of claim 1, wherein the fusion protein further comprises a protease cleavage site between the target protein and the self-assembly domain.

5. A cell lysate comprising the fusion protein of claim 1.

6. A protein aggregate comprising the fusion protein of claim 1.

7. A host cell comprising the fusion protein of claim 1.

8. A method for aggregating a target protein comprising:
   (i) formulating an aqueous composition comprising the fusion protein of claim 1; and
   (ii) heating the aqueous composition to a temperature between about 25° C. and about 50° C.

9. The fusion protein of claim 1, wherein the self-assembly domain is less than 500 amino acids in length, and wherein the fusion protein consists of the self-assembly domain and the target protein.

* * * * *